(12) United States Patent
Satchi-Fainaro et al.

(10) Patent No.: US 9,283,279 B2
(45) Date of Patent: Mar. 15, 2016

(54) TARGETED POLYMERIC CONJUGATES AND USES THEREOF

(75) Inventors: Ronit Satchi-Fainaro, Tel-Aviv (IL); Gianfranco Pasut, Padua (IT)

(73) Assignees: Ramot at Tel-Aviv University Ltd., Tel-Aviv (IL); Universita degli Studi di Padova, Padua (IT)

( * ) Notice: Subject to any disclaimer, the term of this patent is extended or adjusted under 35 U.S.C. 154(b) by 155 days.

(21) Appl. No.: 14/117,043

(22) PCT Filed: May 10, 2012

(86) PCT No.: PCT/IB2012/052338
§ 371 (c)(1),
(2), (4) Date: Nov. 12, 2013

(87) PCT Pub. No.: WO2012/153297
PCT Pub. Date: Nov. 15, 2012

(65) Prior Publication Data
US 2014/0271483 A1    Sep. 18, 2014

Related U.S. Application Data

(60) Provisional application No. 61/484,991, filed on May 11, 2011.

(51) Int. Cl.
| A61K 9/00 | (2006.01) |
| A61K 47/24 | (2006.01) |
| A61K 49/00 | (2006.01) |
| G01N 33/50 | (2006.01) |
| G01N 33/574 | (2006.01) |
| A61K 47/48 | (2006.01) |

(52) U.S. Cl.
CPC ........... *A61K 47/24* (2013.01); *A61K 47/48084* (2013.01); *A61K 47/48215* (2013.01); *A61K 49/0008* (2013.01); *G01N 33/5091* (2013.01); *G01N 33/574* (2013.01); *A61K 47/48169* (2013.01); *A61K 47/48253* (2013.01)

(58) Field of Classification Search
None
See application file for complete search history.

(56) References Cited

U.S. PATENT DOCUMENTS

| 5,714,166 | A | 2/1998 | Tomalia et al. |
| 6,417,339 | B1 | 7/2002 | Wiessler et al. |
| 6,632,889 | B1 | 10/2003 | Yin et al. |
| 6,884,817 | B2 | 4/2005 | Li et al. |
| 2003/0023968 | A1 | 1/2003 | Nishi et al. |
| 2003/0064050 | A1 | 4/2003 | Malik et al. |
| 2004/0192769 | A1 | 9/2004 | Greenwald et al. |

FOREIGN PATENT DOCUMENTS

| CN | 101835496 | 9/2010 |
| WO | WO 2004/089420 | 10/2004 |
| WO | WO 2009/055014 | 4/2009 |
| WO | WO 2009/141823 | 11/2009 |
| WO | WO 2010/143218 | 12/2010 |
| WO | WO 2012/153297 | 11/2012 |

OTHER PUBLICATIONS

Notification of Office Action and Search Report Dated Dec. 11, 2014 From The State Intellectual Property Office of the People's Republic of China Re. Application No. 201280034478.5.
Translation Dated Jan. 4, 2015 of Office Action and Search Report Dated Dec. 11, 2014 From The State Intellectual Property Office of the People's Republic of China Re. Application No. 201280034478.5.
International Search Report and the Written Opinion Dated Jul. 31, 2012 From the International Searching Authority Re. Application No. PCT/IB2012/052338.
Allen "Ligand-Targeted Therapeutics in Anticancer Therapy", Nture Reviews Cancer, 2: 750-763, Oct. 2002.
Andersson et al. "Poly(Ethylene Glycol)-Poly(Ester-Carbonate) Block Copolymers Carrying PEG-Peptidyl-Doxorubicin Pendant Side Chains: Synthesis and Evaluation as Anticancer Conjugates", Biomacromolecules, 6: 914-926, 2005.
Berna et al. "Novel Monodisperse PEG-Dendrons as New Tools for Targetes Drug Delivery: Synthesis, Characterization and Cellular Uptake", Biomacromolecules, 7: 146-153, 2006.
Canal et al. "Relevance of Folic Acid/Polymer Ration in Targeted PEG-Epirubicin Conjugates", Journal of Controlled Release, XP027260371, 146(3): 388-399, Sep. 15, 2010. Abstract, Scheme 1, Compounds 7, 8, 9.
Choe et al. "Anticancer Drug Delivery Systems: Multi-Loaded N4-Acyl Poly(Ethylene Glycol) Prodrugs of Ara-C. I. Efficacy in Solid Tumors", Journal of Controlled Release, 79: 41-53, 2002.
Choe et al. "Anticancer Drug Delivery Systems: Multi-Loaded N4-Acyl Poly(Ethylene Glycol) Prodrugs of Ara-C. II. Efficacy in Ascites and Solid Tumors", Journal of Controlled Release, 79: 55-70, 2002.
Clementi et al. "Dendritic Poly(Ethylene Glycol) Bearing Paclitaxel and Alendronate for Targeting Bone Neoplasms", Molecular Pharmaceutics, XP002680272, 8: 1063-1072, May 24, 2011.
Duncan "Development of HPMA Copolymer-Anticancer Conjugates: Clinical Experience and Lesson Learnt", Advanced Drug Delivery Reviews, 61: 1131-1148, 2009.
Duncan "Polymer Conjugates as Anticancer Nanomedicines", Nature Reviews Cancer, 6: 688-701, 2006.

(Continued)

*Primary Examiner* — James Rogers

(57) ABSTRACT

Polymeric conjugates comprising a polymeric backbone having attached thereto a bone targeting moiety and a therapeutically active agent, wherein the bone targeting moiety is attached to one end of the polymeric backbone via a branching unit such that a molar ratio of the bone targeting moiety to the polymer is at least 2:1, are disclosed. Pharmaceutical compositions containing these conjugates and uses thereof in the treatment of bone related disorders are also disclosed.

8 Claims, 25 Drawing Sheets
(4 of 25 Drawing Sheet(s) Filed in Color)

(56) References Cited

OTHER PUBLICATIONS

Duncan et al. "A Polymer-Triton X-100 Conjugate Capable of PH-Dependent Red Blood Cell Lysis: A Model System Illustrating the Possibility of Drug Delivery Within Acidic Intracellular Compartments", Journal of Drug Targeting, 2: 341-347, 1994.

Greco et al. "Combination Therapy: Opportunities and Challenges for Polymer-Drug Conjugates as Anticancer Nanomedicines", Advanced Drug Delivery Reviews, 61: 1203-1213, 2009.

Hrubý et al. "Hydroxybisphosphonate-Containing Polymeric Drug-Delivery Systems Designed for Targeting Into Bone Tissue", Journal of Applied Polymer Science, 101: 3192-3201, 2006.

Katsumi et al. "Development of Polyethylene Glycol-Conjugated Alendronate, A Novel Nitrogen-Containing Bisphosphonate Derivative: Evbaluation of Absorption, Safety, and Effects After Intrapulmonary Administration in Rats", Journal of Pharmaceutical Sciences, 100: 3783-3792, 2011.

Meerum Terwogt et al. "Phase I Clinical and Pharmacokinetic Study of PNU166945, A Novel Water-Soluble Polymer-Conjugated Prodrug of Paclitaxel", Anti-Cancer Drug, 12: 315-323, 2001.

Miller et al. "Targeting Bone Metastases With a Bispecific Anticancer and Antiangiogenic Polyme-Alendronate-Taxane Conjugate", Angewandte Chemie International Edition, XP002680271, 48: 2949-2954, Jan. 1, 2009.

Moses et al. "Advancing the Field of Drug Delivery: Taking Aim at Cancer", Cancer Cell, 4: 337-341, 2003.

Ofek et al. "In Vivo Delivery of Small Interfering RNA to Tumors and Their Vasculature by Novel Dendritic Nanocarriers", The FASEB Journal, 24: 3122-3134, 2010.

Pasut et al. "Antitumoral Activity of PEG-Gemcitabine Prodrugs Targeted by Folic Acid", Journal of Controlled Release, 127: 239-248, 2008.

Pasut et al. "PEG-Epirubicin Conjugates With High Drug Loading", Journal of Bioactive and Compatible Polymers, 20: 213-230, May 2005.

Pasut et al. "Polymer—Drug Conjugates for Combination Anticancer Therapy: Investigating the Mechanism of Action", Journal of Medicinal Chemistry, 52: 6499-6502, 2009.

Satchi et al. "PDEPT: Polymer-Directed Enzyme Prodrug Therapy. I. HPMA Copolymer—Cathepsin B and PK1 as a Model Combination", British Journal of Cancer, 85(7): 1070-1076, 2001.

Satchi-Fainaro et al. "Targeting Angiogenesis With a Conjugate of HPMA Copolymer and TNP-470", Nature Medicine, 10(3): 255-261, Mar. 2004.

Segal et al. "Targeting Angiogenesis-Dependent Calcified Neoplasms Using Combined Polymer Therapeutics", PLoS ONE, 4(4): e5233-1-e5233-15, Apr. 2009.

Uludag "Biphosphonates as a Foundation of Drug Delivery to Bone", Current Pharmaceutical Design, 8: 1929-1944, 2002.

Vasey et al. "Phase I Clinical and Pharmacokinetic Study of PK1 [N-(2-Hydroxypropyl)Methacrylamide Copolymer Doxorubicin]: First Member of a New Class of Chemotherapeutic Agents—Drug Polymer Conjugates", Clinical Cancer Research, 5: 83-94, Jan. 1, 1999.

Veronese et al. "PEG-Doxorubicin Conjugates: Influence of Polymer Structure on Drug Release, In Vitro Cytotoxicity, Biodistribution, and Antitumor Acitivity", Bioconjugate Chemistry, 16: 775-784, 2005.

Vicent "Polymer Therapeutics Designed for a Combination Therapy of Hormone-Dependent Cancer", Angewandte Chemie International Edition, 44: 4061-4066, 2005.

Wang et al. "Pharmacokinetic and Biodistribution Studies of a Bone-Targeting Drug Delivery System Based on N-(2-Hydroxypropyl)Methacrylamide Copolymers", Molecular Pharmaceutics, 3(6): 717-725, 2006.

Wang et al. "Synthesis and Evaluation of Water-Soluble Polymeric Bone-Targeted Drug Delivery Systems", Bioconjugate Chemistry, XP002290582, 14: 853-859, Jan. 1, 2003. Abstract.

Yamaoka et al. "Distribution and Tissue Uptake of Poly(Ethylene Glycol) With Different Molecular Weights After Intravenous Administration to Mice", Journal of Pharmaceutical Sciences, 83(4): 601-606, Apr. 1994.

Zhao et al. "Novel Prodrugs of SN38 Using Multiarm Poly(Ethylene Glycol) Linkers", Bioconjugate Chemistry, 19: 849-859, 2008.

PEG-ALN (Compound 1)

PTX-PEG (Compound 2)

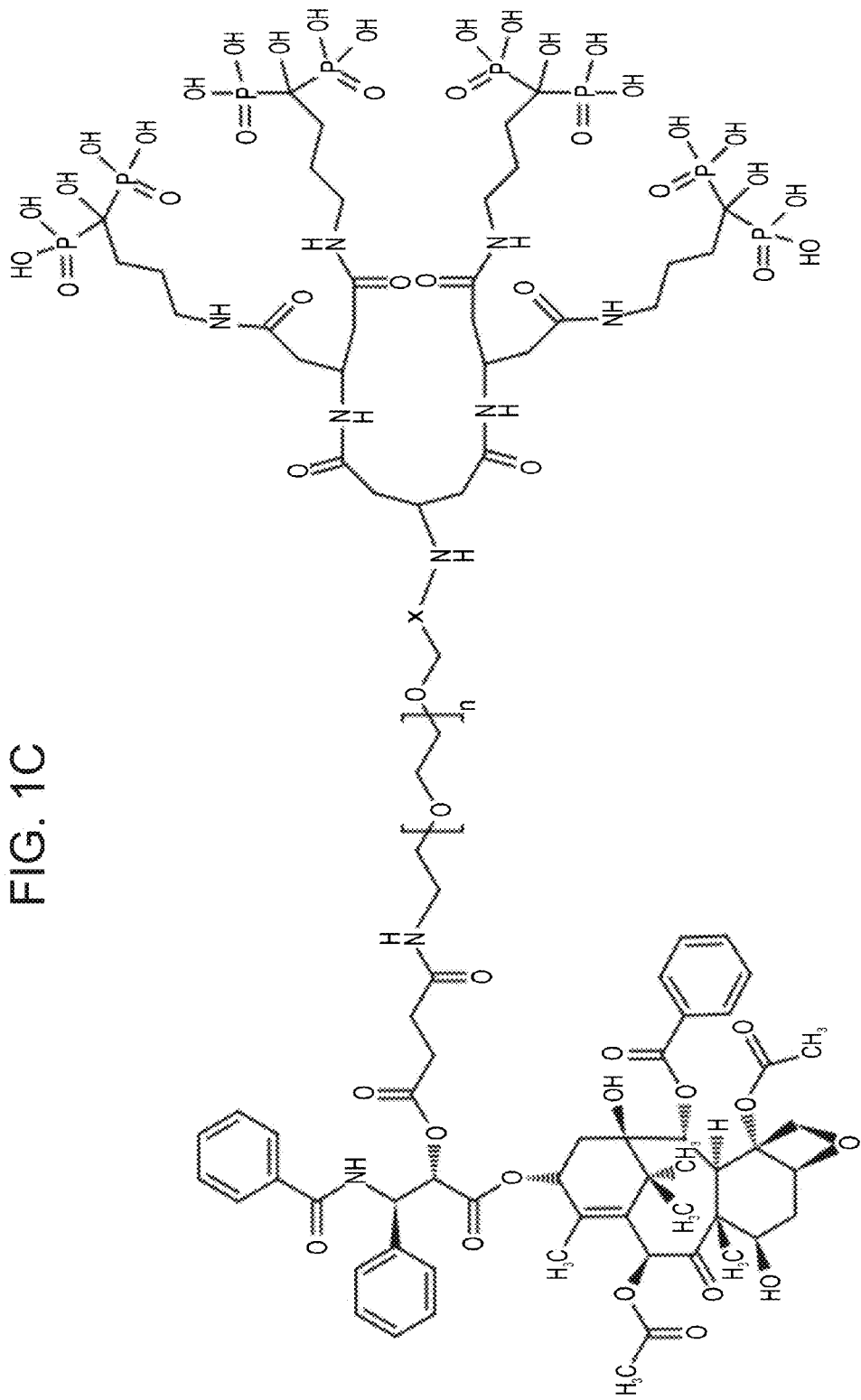
FIG. 1C  PTX-PEG-ALN (Compound 3)

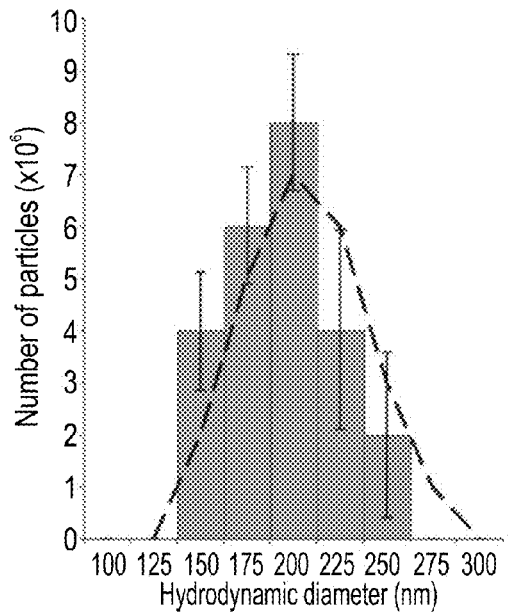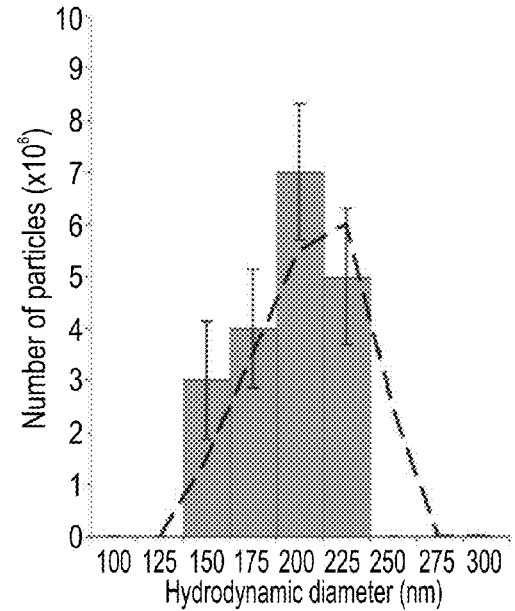
FIG. 4A    FIG. 4B
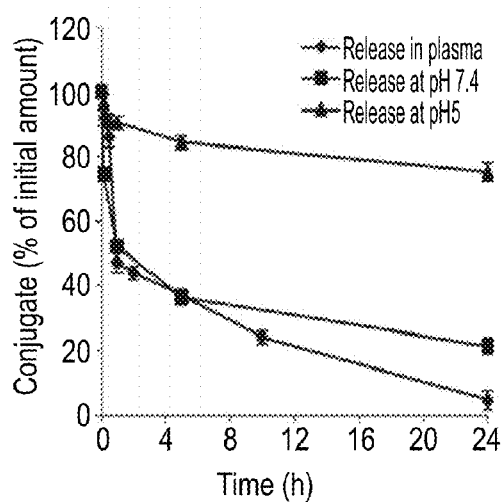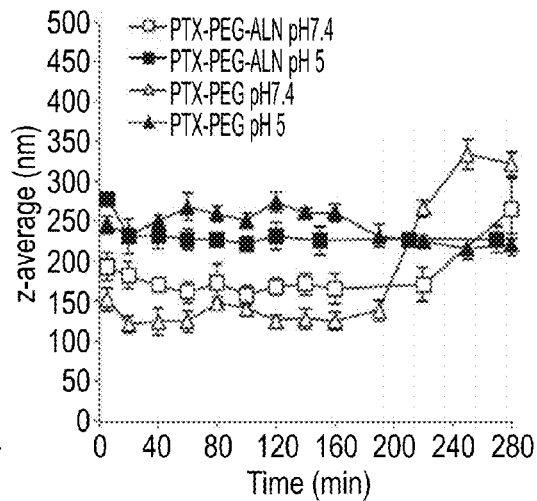
FIG. 5A    FIG. 5B

FIG. 8B
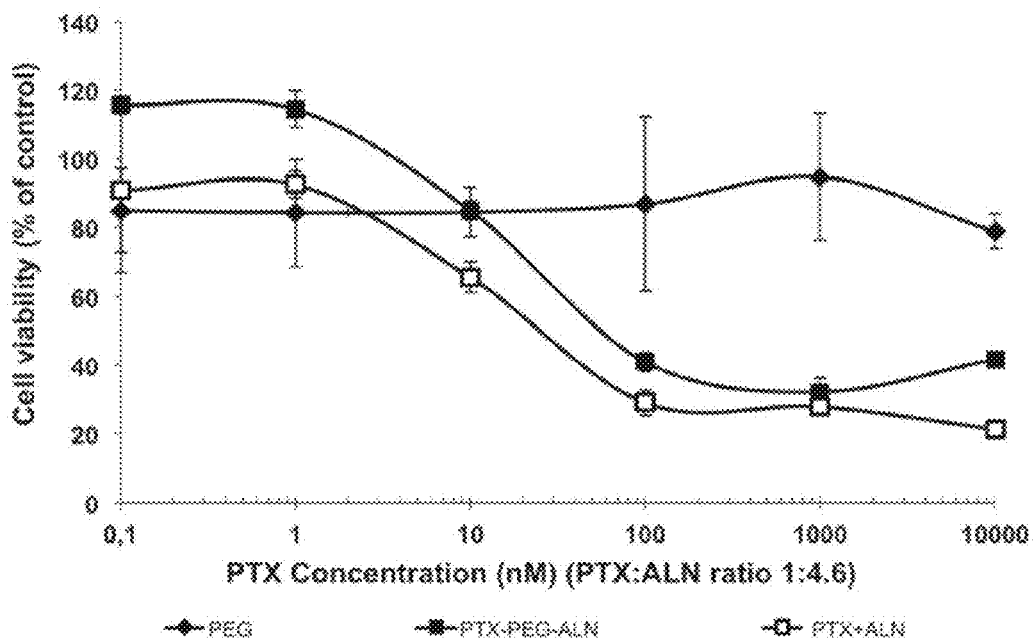
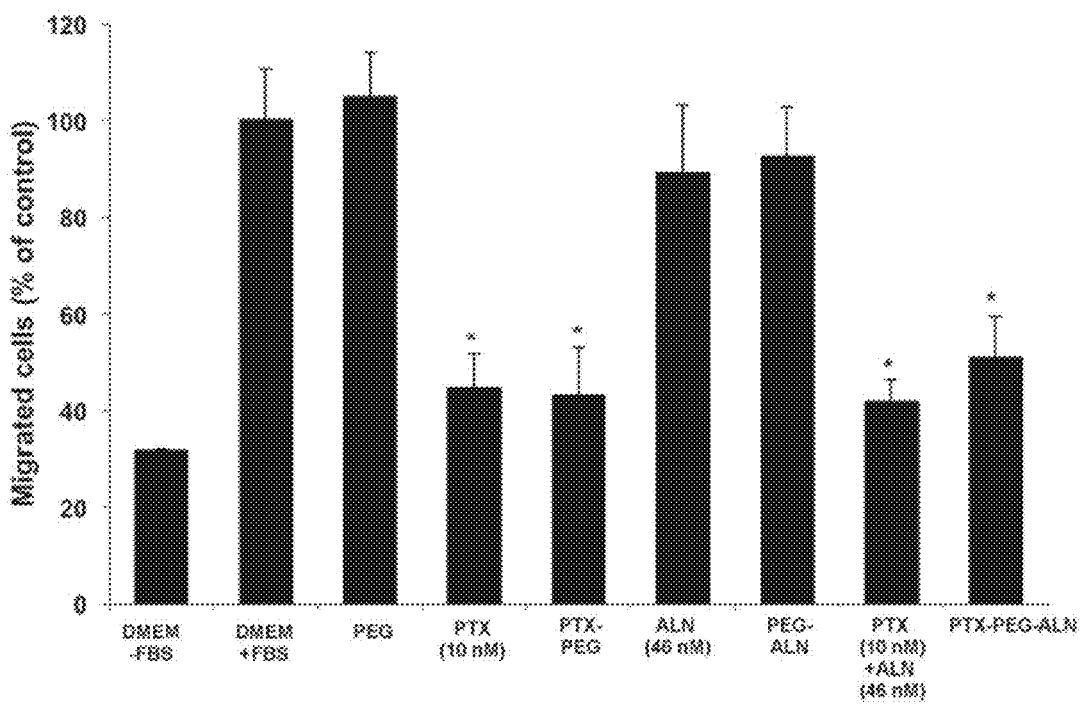
FIG. 9

SEQUENCE LISTING

```
<160> NUMBER OF SEQ ID NOS: 19

<210> SEQ ID NO 1
<211> LENGTH: 3
<212> TYPE: PRT
<213> ORGANISM: Artificial sequence
<220> FEATURE:
<223> OTHER INFORMATION: Exemplary pH-sensitive linking moiety

<400> SEQUENCE: 1

Gly Phe Gly
1

<210> SEQ ID NO 2
<211> LENGTH: 4
<212> TYPE: PRT
<213> ORGANISM: Artificial sequence
<220> FEATURE:
<223> OTHER INFORMATION: An example of a linker having a Cathepsin K
      cleavable site
<220> FEATURE:
<221> NAME/KEY: misc_feature
<222> LOCATION: (4)..(4)
<223> OTHER INFORMATION: Norleucine

<400> SEQUENCE: 2

Gly Gly Pro Xaa
1

<210> SEQ ID NO 3
<211> LENGTH: 5
<212> TYPE: PRT
<213> ORGANISM: Artificial sequence
```

```
<220> FEATURE:
<223> OTHER INFORMATION: An example of a linker having a Cathepsin D
      cleavable site

<400> SEQUENCE: 3

Gly Thr Gln Phe Phe
1               5

<210> SEQ ID NO 4
<211> LENGTH: 5
<212> TYPE: PRT
<213> ORGANISM: Artificial sequence
<220> FEATURE:
<223> OTHER INFORMATION: An example of a linker having a Cathepsin D
      cleavable site

<400> SEQUENCE: 4

Gly Ser Thr Phe Phe
1               5

<210> SEQ ID NO 5
<211> LENGTH: 2
<212> TYPE: PRT
<213> ORGANISM: Artificial sequence
<220> FEATURE:
<223> OTHER INFORMATION: An example of a linker having a Cathepsin H
      cleavable site

<400> SEQUENCE: 5

Leu Gly
1

<210> SEQ ID NO 6
<211> LENGTH: 7
<212> TYPE: PRT
<213> ORGANISM: Artificial sequence
<220> FEATURE:
<223> OTHER INFORMATION: An example of a linker having a Cathepsin L
      cleavable site

<400> SEQUENCE: 6

Ala Phe Arg Ser Ala Ala Gln
1               5

<210> SEQ ID NO 7
<211> LENGTH: 3
<212> TYPE: PRT
<213> ORGANISM: Artificial sequence
<220> FEATURE:
<223> OTHER INFORMATION: An example of a linker having a legumain
      cleavable site

<400> SEQUENCE: 7

Ala Ala Asn
1

<210> SEQ ID NO 8
<211> LENGTH: 8
<212> TYPE: PRT
<213> ORGANISM: Artificial sequence
<220> FEATURE:
<223> OTHER INFORMATION: An example of a linker having an MMP-2 and an
      MMP-9 cleavable site

<400> SEQUENCE: 8

His Pro Val Gly Leu Leu Ala Arg
1               5
```

```
<210> SEQ ID NO 9
<211> LENGTH: 6
<212> TYPE: PRT
<213> ORGANISM: Artificial sequence
<220> FEATURE:
<223> OTHER INFORMATION: An example of a linker having an MMP-2 and an
      MMP-9 cleavable site

<400> SEQUENCE: 9

Pro Val Ser Leu Ser Tyr
1               5

<210> SEQ ID NO 10
<211> LENGTH: 8
<212> TYPE: PRT
<213> ORGANISM: Artificial sequence
<220> FEATURE:
<223> OTHER INFORMATION: An example of a linker having an MMP-2 and an
      MMP-9 cleavable site

<400> SEQUENCE: 10

Gly Pro Val Gly Leu Ile Gly Lys
1               5

<210> SEQ ID NO 11
<211> LENGTH: 2
<212> TYPE: PRT
<213> ORGANISM: Artificial sequence
<220> FEATURE:
<223> OTHER INFORMATION: An example of a linker having a Cathepsin B
      cleavable site
<220> FEATURE:
<221> NAME/KEY: misc_feature
<222> LOCATION: (1)..(1)
<223> OTHER INFORMATION: Citrulline

<400> SEQUENCE: 11

Xaa Val
1

<210> SEQ ID NO 12
<211> LENGTH: 2
<212> TYPE: PRT
<213> ORGANISM: Artificial sequence
<220> FEATURE:
<223> OTHER INFORMATION: An example of a linker having a Cathepsin B
      cleavable site

<400> SEQUENCE: 12

Arg Arg
1

<210> SEQ ID NO 13
<211> LENGTH: 2
<212> TYPE: PRT
<213> ORGANISM: Artificial sequence
<220> FEATURE:
<223> OTHER INFORMATION: An example of a linker having a Cathepsin B
      cleavable site

<400> SEQUENCE: 13

Phe Lys
1

<210> SEQ ID NO 14
<211> LENGTH: 4
```

```
<212> TYPE: PRT
<213> ORGANISM: Artificial sequence
<220> FEATURE:
<223> OTHER INFORMATION: An example of a linker having a Cathepsin B
      cleavable site

<400> SEQUENCE: 14

Gly Phe Leu Gly
1

<210> SEQ ID NO 15
<211> LENGTH: 4
<212> TYPE: PRT
<213> ORGANISM: Artificial sequence
<220> FEATURE:
<223> OTHER INFORMATION: An example of a linker having a Cathepsin B
      cleavable site

<400> SEQUENCE: 15

Gly Phe Ala Leu
1

<210> SEQ ID NO 16
<211> LENGTH: 4
<212> TYPE: PRT
<213> ORGANISM: Artificial sequence
<220> FEATURE:
<223> OTHER INFORMATION: An example of a linker having a Cathepsin B
      cleavable site

<400> SEQUENCE: 16

Ala Leu Ala Leu
1

<210> SEQ ID NO 17
<211> LENGTH: 3
<212> TYPE: PRT
<213> ORGANISM: Artificial sequence
<220> FEATURE:
<223> OTHER INFORMATION: An example of a linker having a Cathepsin B
      cleavable site

<400> SEQUENCE: 17

Gly Leu Gly
1

<210> SEQ ID NO 18
<211> LENGTH: 3
<212> TYPE: PRT
<213> ORGANISM: Artificial sequence
<220> FEATURE:
<223> OTHER INFORMATION: An example of a linker having a Cathepsin B
      cleavable site

<400> SEQUENCE: 18

Gly Phe Gly
1

<210> SEQ ID NO 19
<211> LENGTH: 6
<212> TYPE: PRT
<213> ORGANISM: Artificial sequence
<220> FEATURE:
<223> OTHER INFORMATION: An example of a linker having a Cathepsin B
      cleavable site
```

<400> SEQUENCE: 19
Gly Phe Leu Gly Phe Lys
1               5

TARGETED POLYMERIC CONJUGATES AND USES THEREOF

RELATED APPLICATIONS

This application is a National Phase of PCT Patent Application No. PCT/IB2012/052338 having International filing date of May 10, 2012, which claims the benefit of priority under 35 USC §119(e) of U.S. Provisional Patent Application No. 61/484,991 filed on May 11, 2011. The contents of the above applications are all incorporated by reference as if fully set forth herein in their entirety.

SEQUENCE LISTING STATEMENT

The ASCII file, entitled 57687 SequenceListing.txt, created on Oct. 20, 2013, comprising 4,185 bytes, submitted concurrently with the filing of this application is incorporated herein by reference.

FIELD AND BACKGROUND OF THE INVENTION

The present invention, in some embodiments thereof, relates to polymeric conjugates and their use in therapy and/or diagnosis and, more particularly, but not exclusively, to bone-targeted polymeric conjugates and to uses thereof in treating and/or monitoring bone-related diseases and disorders.

A limiting factor for the success of cancer chemotherapy lies in the accumulation of the therapeutic agents in tumors. Difficulties are encountered in the administration of sufficient quantities of chemotherapeutic agents which provide the in vivo concentration of the chemotherapeutic agent required to afford an effective killing of cancer cells.

The accumulation of chemotherapeutic agents in tumors depend on several factors including the size, surface characteristics and circulation half-life of the chemotherapeutic agents, as well as the degree of angiogenesis in the tumors.

Polymer-anticancer drug conjugates have been investigated, as therapies against cancer aimed at addressing the relevant limitations of current protocols using low molecular weight drugs. The coupling of anti-cancer agents with water-soluble polymers has been demonstrated to improve both the safety profile and antitumor efficacy due to, for example, possible avoidance of toxic formulations; and to contribute to improved biodistribution and pharmacokinetics, which results from their restricted distribution and the enhanced permeability and retention (EPR) effect, which promotes passive targeting to solid tumors.

An example of the increased activity yet reduced toxicity obtained by conjugation of anti-tumor drugs to water-soluble polymers is presented in U.S. Pat. No. 6,884,817.

Recent studies have been directed to either synthesizing targeted conjugates [Allen, T. M. *Nat. Rev. Cancer* 2002; 2: 750-763; Brumlik et al. *Expert Opin. Drug Delivery* 2008; 5: 87-103; Segal et al. *PLoS ONE* 2009; 4: e5233; Canal et al. *J. Controlled Release* 2010, 146: 388-399] or polymers bearing two anticancer drugs for combination therapy [Vicent et al. *Angew. Chem., Int. Ed. Engl.* 2005; 44 (26); 4061-4066; Pasut, et al. *J. Med. Chem.* 2009; 52; 6499-6502. Greco, F.; Vicent et al. *J. Adv. Drug Delivery Rev.* 2009; 61: 1203-1213.]. Satchi-Fainaro et al. disclose targeted conjugates, in which paclitaxel (PTX) and alendronate (ALN) are coupled to HPMA copolymer [Miller et al. *Angew. Chem., Int. Ed. Engl.* 2009; 48: 2949-2954.]. An exemplary such conjugate was shown to exhibit increased anticancer and anti-angiogenic activity with respect to the free drugs and, remarkably, reduced toxicity. Other studies in this regard are described in Segal et al. [*PLoS ONE* 2009; 4: e5233]; and Wang et al. [*Mol. Pharmaceutics* 2006; 3: 717-25].

WO 2004/062588 teaches water soluble polymeric conjugate for bone targeted drug delivery. The polymeric drug delivery systems taught in this application are based on hydroxypropyl methacrylate (HPMA) conjugates of bone-targeting agents, such as alendronate and D-Asp$_8$, together with a chemotherapeutic agent (e.g., tetracycline).

WO 2009/141823 teaches polymeric conjugates comprising a plurality of polymeric backbones (e.g., derived from HPMA) having attached thereto a bone-targeting moiety such as alendronate and an anti-angiogenesis agent such as paclitaxel or TNP-470.

WO 2009/141826 teaches conjugates of a polymer (e.g., PGA) having attached thereto an angiogenesis targeting moiety and a therapeutically-active agent such as an anti-cancer agent or anti-angiogenesis agent.

WO 2009/141827 teaches conjugates of hydroxypropyl methacrylamide (HPMA)-derived copolymers having attached thereto anti-angiogenesis agents such as TNP-470 and a high load of a bone-targeting moiety such as alendronate (ALN).

PTX is a potent anticancer drug, used for the treatment of several cancers, however, it is associated with severe side effects due to both its scarce tumor selectivity and the formulation in Cremophor EL. In recent years, it has become evident that paclitaxel at low doses has antiangiogenic properties (Wang, et al. *Anticancer Drugs* 2003; 14: 13-19).

A HPMA copolymer conjugate of paclitaxel has been described by Meerum Terwogt et al. [PNU166945; *Anticancer drugs* 2001; 12: 315-323]. This conjugate was aimed at improving drug solubility and providing controlled release of paclitaxel.

Bisphosphonates, such as alendronate (ALN), are molecules used to treat osteoporosis, bone metastases and to prevent bone fractures. These compounds exhibit an exceptionally high affinity to the bone-mineral hydroxyapatite, and therefore are known to be used also as a targeting moiety [Uludag, H. *Curr Pharm Des* 2002; 8: 1929-1944].

Alendronate is considered potent for the treatment of bone related diseases and cancer-associated hypercalcemia. It was shown to have antitumor effect in several in vivo cancer models through several different mechanisms [Tuomela et al. 2008, *BMC Cancer* 8:81; Molinuevo et al. 2007, *Eur J Pharmacol* 562:28-33; Hashimoto et al. 2005, *Cancer Res* 65: 540-545]. In addition, alendronate was found to have anti-angiogenic activity through (i) suppression of VEGF-induced Rho activation in an ovarian cancer model [Hashimoto et al. 2007, *Biochem Biphys Res Commun* 354: 478-484], (ii) inhibition of farnesyl pyrophosphate synthase, in the mevalonate pathway [Russell R G 2007, *Pediatrics* 119 Suppl 2: S150-162]; and (iii) regulation of cellular level of MMP-2 expression in osteosarcoma cell lines [Cheng et al. 2004, *Pediatr Blood Cancer* 42; 410-415].

Poly(ethylene glycol) (PEG) is a polymer approved for human use. While it is known to be non-biodegradable, it is readily excretable after administration into living organisms. High excretion is typically observed for polymers having a molecular weight lower than 40 kDa or for polymers having a hydrodynamic diameter of less than 100 nm. In vitro studies showed that its presence in aqueous solutions has shown no deleterious effect on protein conformation or activities of enzymes. Covalent attachment of PEG to biologically active compounds is described, for example, in Yamaoka et al. [1994, *J Pharm Sci* 83; 601-606].

However, the potential of PEG as a carrier of low molecular weight drugs (small molecules) has been limited by its intrinsic low loading, owing to the polymer's chemical structure. In fact, only the end chain groups (at the termini) of PEG can be modified and exploited for drug coupling.

Wang et al. [in *Bioconj. Chem.*, 2003, 14, 853-859] teach bone-targeted drug delivery systems based on water-soluble polymers such as PEG and HPMA, have attached thereto bone targeting moieties such as alendronate and $Asp_8$, and FITC as a model drug for detection purposes.

Katsumi et al. [in J. Pharma. Sci., 2011, 100, 3783-3792] also teach PEG-conjugated alendronate, and its effect in treating osteoporosis.

Pasut et al. [in *J. Bioactive and Comp. Polym.*, 2005, 20, 213] discloses PEG-epirubicin conjugates with high drug loading, having dendrimeric (dendritic) structures based on adipic acid or beta-glutamic acid branching units.

Pasut et al. [in *J. Med. Chem.* 2009; 52 (20), 6499-6502] reported on the synthesis, characterization, and biological performance of PEG conjugates carrying epirubicin (EPI) and one or more nitric oxide (NO) molecules per PEG.

Bioconjugates of poly(ethylene glycol), gemcitabine (an antitumor agent), and a targeting moiety, differing in the drug loading, have also been reported [Pasut et al, *J. Control Release.* 2008; 127(3): 239-48].

Canal et al. [in *J. Controlled Release* 2010; 146: 388-399] disclosed a series of PEG-epirubicin conjugates with different folic acid contents per polymeric chain. A dendron structure was synthesized at one end of the PEG chain with the aim of increasing the number of folic acid molecules.

Choe et al. [in *J. Controlled Release* 2002; 79: 41-53] reported on a study of various N-amino PEG-prodrugs of ara-C. In an LX-1 solid lung tumor model, some of the PEG prodrugs exhibited superior activity to ara-C when compared on a molar basis. However, the degree of loading ara-C onto PEG was limited by the high viscosity of the obtained solutions.

Choe et al. [in *J. Controlled Release* 2002; 79: 55-70] described the synthesis of branched PEG (40,000) acids which had been achieved using aspartic acid (Asp) and AspAsp dendrons. Conjugation of these dendritic acids with cytosine arabinoside (ara-C) was achieved by the use of spacers that allowed a greater separation of the branches to accommodate several large ara-C molecules in proximity to each other.

Berna et al. [in *Biomacromolecules* 2006, 7:146-153] synthesized novel monodisperse PEG-dendrons with amino or carboxylic terminal groups. The PEG-based dendrons were prepared using monodisperse Fmoc-amino PEG propionic acid as a monomer, and cadaverine, tris(2-aminoethyl)amine or lysine as the branching moieties.

Other combinations of dendritic structures and drugs, or other biologically active molecules, are disclosed, for example, in U.S. Pat. Nos. 5,714,166, 6,417,339 and 6,632,889; and in U.S. patent applications having Publication Nos. 2003/064050 and 2003/023968.

Bone metastases are one of the most common complications related to advanced malignancies, particularly in the three leading cancers; breast cancer, prostate cancer and lung cancer. Bone metastases from breast cancer are typically osteolytic, involving the mobilization of osteoclasts that cause pathological bone resorption, with intense pain, bone fractures, nerve compression, and hypercalcemia. The development and osteolytic nature of these lesions are based on complex interactions between cancer cells and bone marrow stroma in a cycle of bone destruction and tumor expansion. The complexity of cellular interactions and molecular components implicated in bone metastasis has hindered a mechanistic elucidation of key biological features of this process, in particular the basis for long-term survival of metastatic cells in the bone marrow.

Chemotherapeutic agents, hormonal deprivation and bisphosphonates are the common treatments for advanced metastatic disease. However, with time, the disease progresses to a phase when the standard therapy fails to control the malignancy and further progresses to a highly chemotherapy-resistant state.

SUMMARY OF THE INVENTION

According to an aspect of some embodiments of the present invention there is provided a conjugate comprising a polymeric backbone having attached thereto a therapeutically active agent and a bone targeting moiety, the therapeutically active agent being attached to one end of the polymeric backbone and the bone targeting moiety being attached to another end of the polymeric backbone via a branching unit, wherein a molar ratio of the bone targeting moiety to the polymer and is at least 2:1.

According to some embodiments of the present invention, the branching unit has a dendritic structure.

According to some embodiments of the present invention, the branching unit comprises at least one trifunctional moiety which comprises at least 3 functional groups, each of the functional groups being independently selected from the group consisting of an amine, a carboxylate, a thiocarboxylate, hydroxy, thiol, carbamate, thiocarbamate, sulfonate, sulfinate, sulfonamide, phosphonate, phosphinate, phosphoryl, urea and thiourea.

According to some embodiments of the present invention, the trifunctional moiety is selected from the group consisting of glutamic acid, beta-glutamic acid, amino adipic acid aspartic acid, lysine, and 3-hydroxy-2-amine propanol.

According to some embodiments of the present invention, the branching unit has a dendritic structure and the conjugate is represented by the general Formula I:

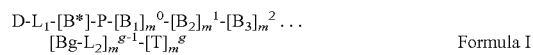

Formula I wherein:

D is the therapeutically active agent;

P is the polymeric backbone;

T is the bone targeting moiety;

B* is a branching unit or is absent;

$L_1$ is a linking moiety, linking the therapeutically active agent to the one end of the polymeric backbone;

$L_2$ is a second linking moiety, linking the targeting moiety to the another end of the polymer, via the branching unit, or is absent;

$B_1$, $B_2$, $B_3$ . . . Bg are each independently a branching moiety, wherein $B_1$, $B_2$, $B_3$ . . . Bg together form the branching unit having the dendritic structure;

m is an integer that equals 2, 3, 4, 5 or 6, representing the ramification number of the dendritic structure; and g is an integer that ranges from 1 to 20, representing the number of generations of the dendritic structure.

According to some embodiments of the present invention, the therapeutically active agent is selected from the group consisting of an anti-angiogenesis agent and an anti-cancer agent.

According to some embodiments of the present invention, the therapeutically active agent is useful in treating a bone-related disease or disorder.

According to some embodiments of the present invention, the therapeutically active agent is selected from the group consisting of paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, a matrix metalloproteinase, penicillamine, PTK787/ZK 222584, RPI.4610, squalamine lactate, SU5416, thalidomide, TNP-470, combretastatin, tamoxifen, COL-3, neovastat, BMS-275291, SU6668, anti-VEGF antibody, Medi-522 (Vitaxin II), CAI, Interleukin-12, IM862, Amilloride, Angiostatin® Protein, Angiostatin K1-3, Angiostatin K1-5, Captopril, DL-alpha-Difluoromethylornithine, DL-alpha-Difluoromethylornithine HCl, His-Tag® Endostatin™ Protein, Fumagillin, Herbimycin A, 4-Hydroxyphenylretinamide, Juglone, Laminin, Laminin Hexapeptide, Laminin Pentapeptide, Lavendustin A, Medroxyprogesterone, Medroxyprogesterone Acetate, Minocycline, Minocycline HCl, Placental Ribonuclease Inhibitor, Suramin, Sodium Salt Suramin, Human Platelet Thrombospondin, Neutrophil Granulocyte, a monoclonal antibodies directed against specific proangiogenic factors and/or their receptors, a tyrosine kinase inhibitor of multiple proangiogenic growth factor receptors, an inhibitor of mTOR, an interferon, IL-12, EMD121974 (Cilengitide), Vitaxin; Squalamin, a COX-2 inhibitor, a PDGFR inhibitor, NM3 and 2-ME2.

According to some embodiments of the present invention, the therapeutically active agent is paclitaxel (PTX).

According to some embodiments of the present invention, the therapeutically active agent is attached to the polymeric backbone via a biocleavable linking moiety.

According to some embodiments of the present invention, the biocleavable linking moiety is selected from the group consisting of a hydrolytically-cleavable linking moiety, a pH-sensitive linking moiety and an enzymatically-cleavable linking moiety.

According to some embodiments of the present invention, the biocleavable moiety is a hydrolytically-cleavable linking moiety.

According to some embodiments of the present invention, the hydrolytically-cleavable linking moiety comprises an ester bond.

According to some embodiments of the present invention, hydrolytically-cleavable linking moiety is derived from succinic acid.

According to some embodiments of the present invention, the enzymatically-cleavable linking moiety is cleaved by an enzyme that is overexpressed in a diseased bone tissue.

According to some embodiments of the present invention, the enzyme is an extracellular enzyme.

According to some embodiments of the present invention, the enzymatically-cleavable linking moiety is cleaved by an enzyme selected from the group consisting of Cathepsin K, Cathepsin D, Cathepsin H, Cathepsin L, legumain, MMP-2 and MMP-9.

According to some embodiments of the present invention, the polymeric backbone is derived from a polymer selected from the group consisting of a poly(alkylene glycol), a poly(2-alkyl-2-oxazoline), and a copolymer comprising a poly(alkylene glycol) and/or a poly(2-alkyl-2-oxazoline).

According to some embodiments of the present invention, the polymeric backbone is derived from a poly(alkylene glycol).

According to some embodiments of the present invention, the polymeric backbone is derived from poly(ethylene glycol) (PEG).

According to some embodiments of the present invention, the bone targeting moiety is a bisphosphonate moiety.

According to some embodiments of the present invention, the bisphosphonate moiety is selected from a group consisting of alendronate, cimadronate, clodronate, tiludronate, etidronate, ibandronate, neridronate, olpadronate, risedonate, piridronate, pamidronate and zoledronate.

According to some embodiments of the present invention, the bisphosphonate is alendronate.

According to some embodiments of the present invention, the polymer is a poly(ethylene glycol), the bone targeting moiety is alendronate, and the therapeutically active agent is paclitaxel.

According to some of these embodiments of the present invention, the branching unit has a dendritic structure and comprises at least 3 beta-glutamic acid moieties arranged in the dendritic structure.

According to some embodiments of the present invention, the paclitaxel is attached to the terminus backbone unit via a hydrolytically-cleavable linking moiety.

According to some embodiments of the present invention, the hydrolytically-cleavable linking moiety comprises an ester bond.

According to some embodiments of the present invention, the conjugate further comprises a labeling agent attached thereto.

According to some embodiments of the present invention, the labeling agent is selected from the group consisting of a fluorescent agent, a radioactive agent, a magnetic agent, a chromophore, a bioluminescent agent, a chemiluminescent agent, a phosphorescent agent and a heavy metal cluster.

According to an aspect of some embodiments of the present invention there is provided a pharmaceutical composition comprising, as an active ingredient, any of the conjugates as described herein and a pharmaceutically acceptable carrier.

According to some embodiments of the present invention, the pharmaceutical composition is packaged in a packaging material and identified in print, in or on the packaging material, for use in the treatment of a bone related disease or disorder.

According to some embodiments of the present invention, the conjugate comprises a labeling agent, and the composition is packaged in a packaging material and identified in print, in or on the packaging material, for use in monitoring a bone related disease or disorder.

According to an aspect of some embodiments of the present invention there is provided a method of treating a bone related disease or disorder in a subject in need thereof, the method comprising administering to the subject a therapeutically effective amount of the conjugate as described herein.

According to an aspect of some embodiments of the present invention there is provided a method of monitoring a bone related disease or disorder in a subject, the method comprising:

administering to the subject a conjugate as described herein, which further comprises a labeling agent; and employing an imaging technique for monitoring a distribution of the conjugate within the body or a portion thereof.

According to an aspect of some embodiments of the present invention there is provided a use of the conjugate as described herein as a medicament.

According to an aspect of some embodiments of the present invention there is provided a use of the conjugate as described herein in the manufacture of a medicament for treating a bone-related disease or disorder.

According to an aspect of some embodiments of the present invention there is provided a use of the conjugate as described herein, which further comprises a labeling agent, as a diagnostic agent.

According to an aspect of some embodiments of the present invention there is provided a use of the conjugate as described herein, which further comprises a labeling agent, in the manufacture of a diagnostic agent for monitoring a bone related disease or disorder.

According to an aspect of some embodiments of the present invention there is provided a conjugate as described herein, identified for use in the treatment of a bone related disease or disorder.

According to an aspect of some embodiments of the present invention there is provided a conjugate as described herein, which further comprises a labeling agent, identified for use in monitoring of a bone related disease or disorder.

According to some embodiments of the present invention, the disease or disorder is associated with angiogenesis.

According to some embodiments of the present invention, the disease or disorder is selected from the group consisting of bone metastases and bone cancer.

According to an aspect of some embodiments of the present invention there is provided a conjugate comprising a polymeric backbone having attached to one end thereof a bisphosphonate moiety, the bisphosphonate being attached to the polymeric backbone via a branching unit, wherein a mol ratio of the bisphosphonate to the polymer is at least 2:1.

According to some embodiments of the present invention, the polymeric backbone is derived from a poly(alkylene glycol).

According to an aspect of some embodiments of the present invention there is provided a conjugate comprising polymeric backbone having attached thereto a therapeutically active agent, the therapeutically active agent being attached to one end of the polymeric backbone, wherein the polymeric backbone further comprises a reactive group attached to another end of the polymeric backbone via a branching unit, wherein a molar ratio of the functional group to the polymer and is at least 2:1.

According to some embodiments of the present invention, the reactive group is useful for attaching to the conjugate a targeting moiety.

According to an aspect of some embodiments of the present invention there is provided a process of preparing a conjugate as described herein, the process comprising:

providing a conjugate comprising a polymeric backbone having attached to one end thereof a bisphosphonate moiety, wherein the bisphosphonate is being attached to the polymeric backbone via a branching unit, as described herein;

providing the therapeutically active agent; and attaching the therapeutically active agent to the conjugate comprising a bisphosphonate moiety described immediately hereinabove, thereby preparing the conjugate.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
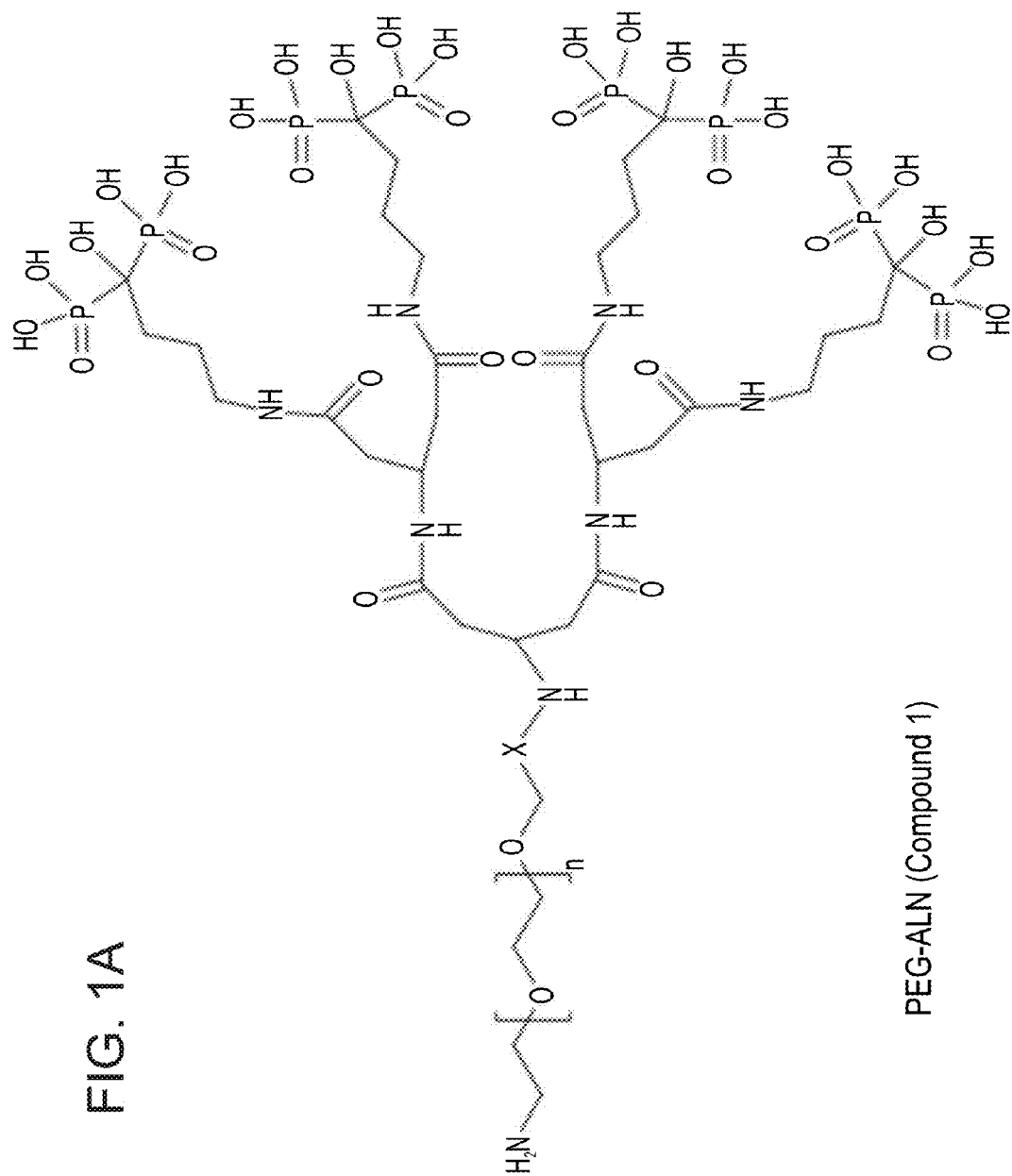
Figure 1B:
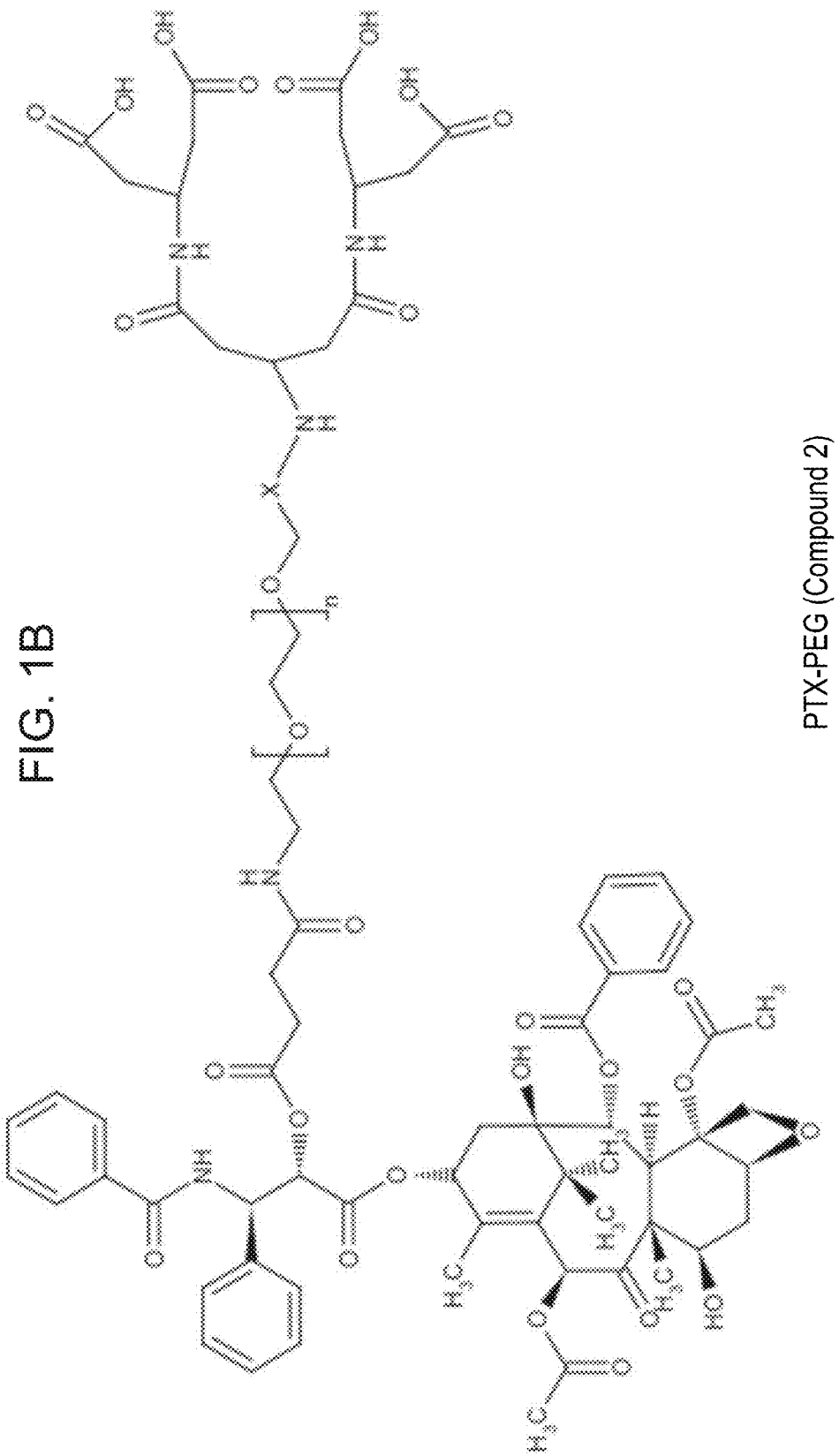
Figure 1C:
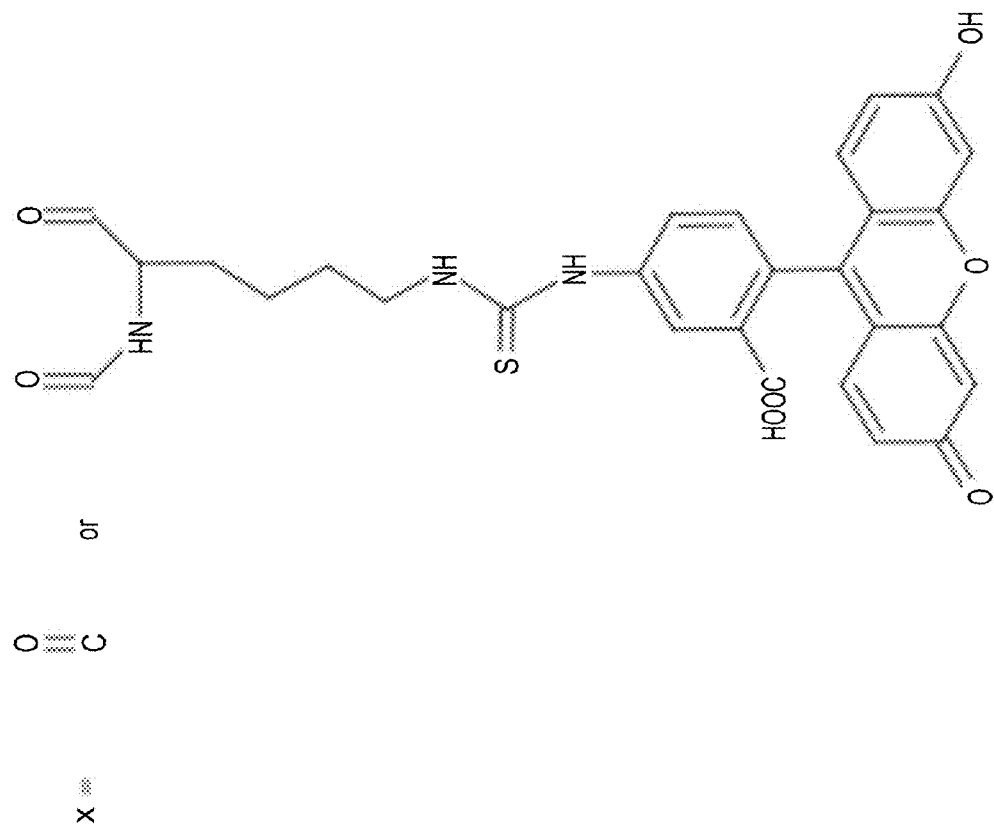

FIGS. 1A-C present the chemical structures of the exemplary conjugates, according to some embodiments of the present invention, PEG-ALN (Compound 1, FIG. 1A), PTX-PEG (Compound 2, FIG. 1B), and PEG-PTX-ALN (Compound 3, FIG. 1C); Non-labeled conjugates are represented by chemical structures in which X is —C(=O)— and FITC-labeled conjugates are represented by chemical structures in which X is a lysine residue coupled to FITC.

Figure 2:
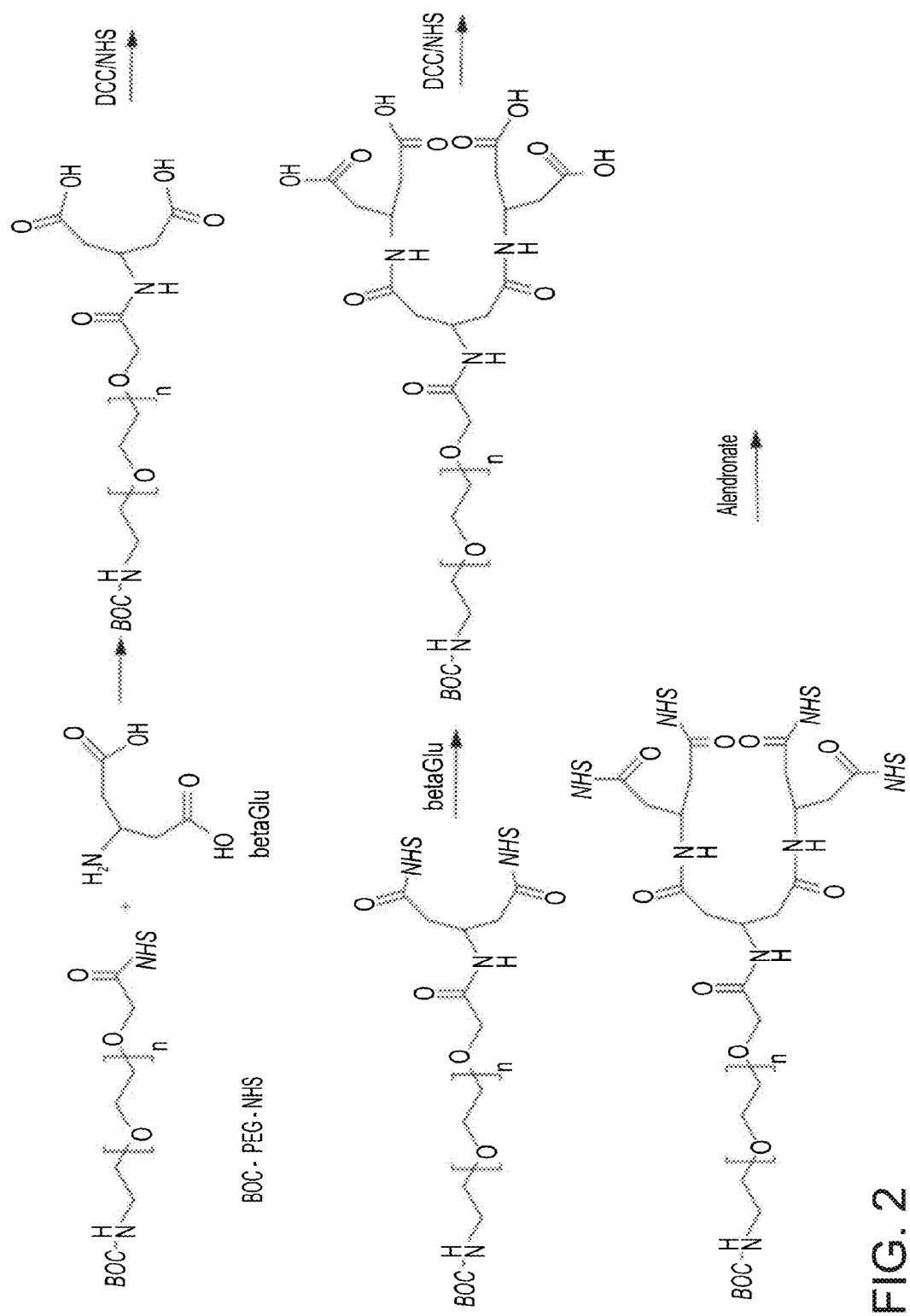
Figure 2:
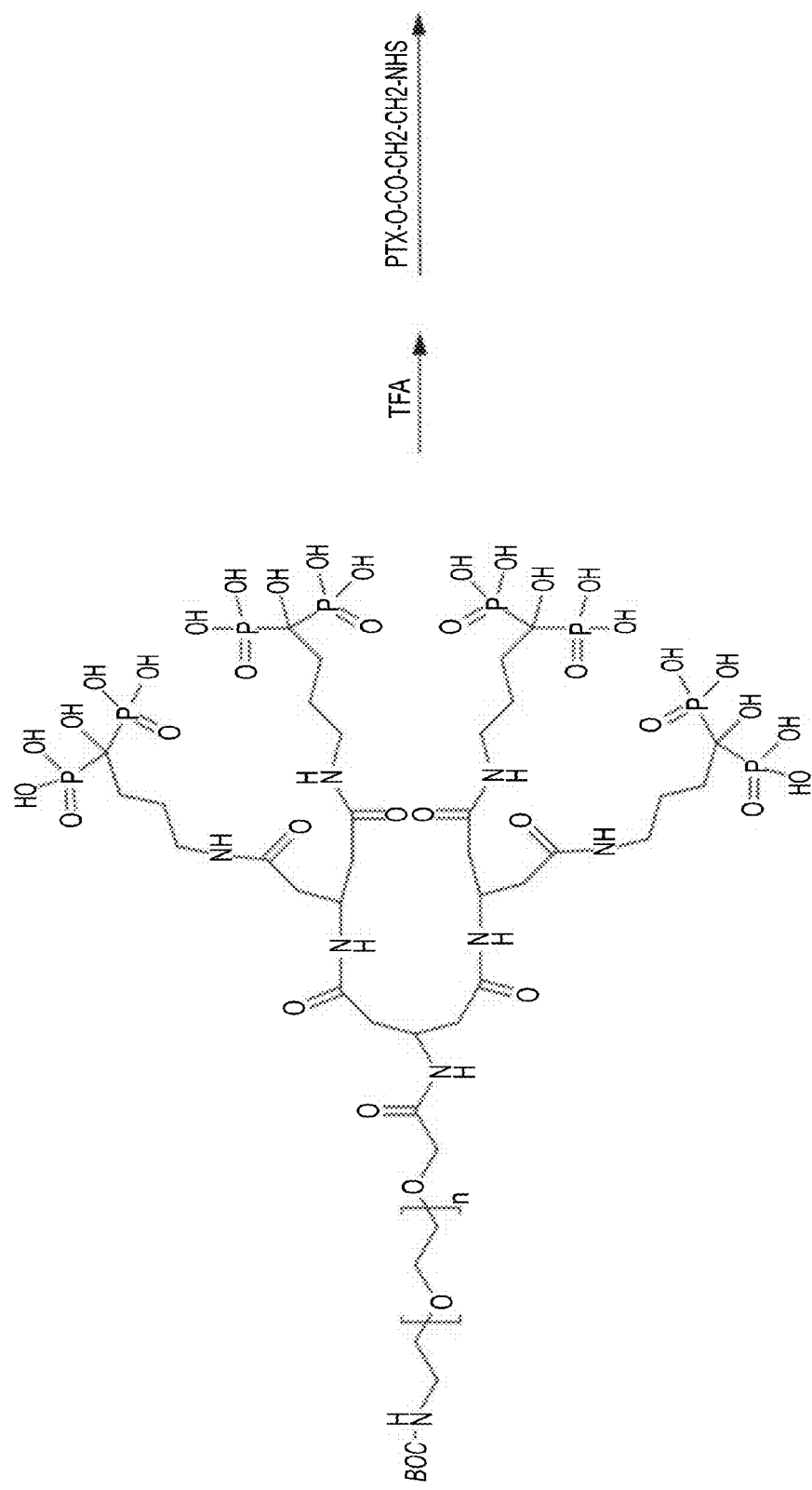
Figure 2:
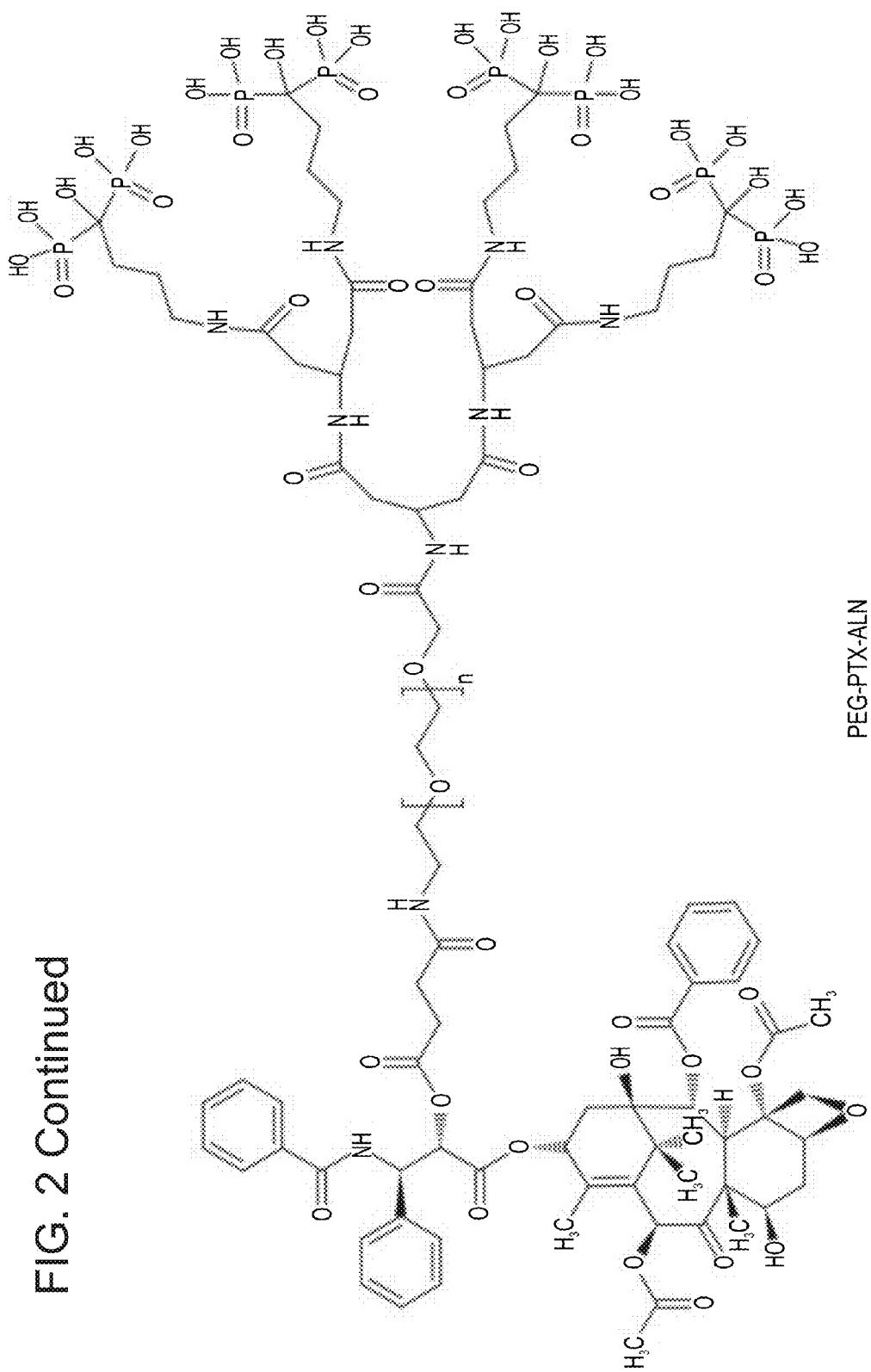

FIG. 2 presents a schematic illustration of an exemplary synthetic pathway for preparing PTX-PEG-ALN conjugate (Compound 3) according to some embodiments of the present invention.

Figure 3:
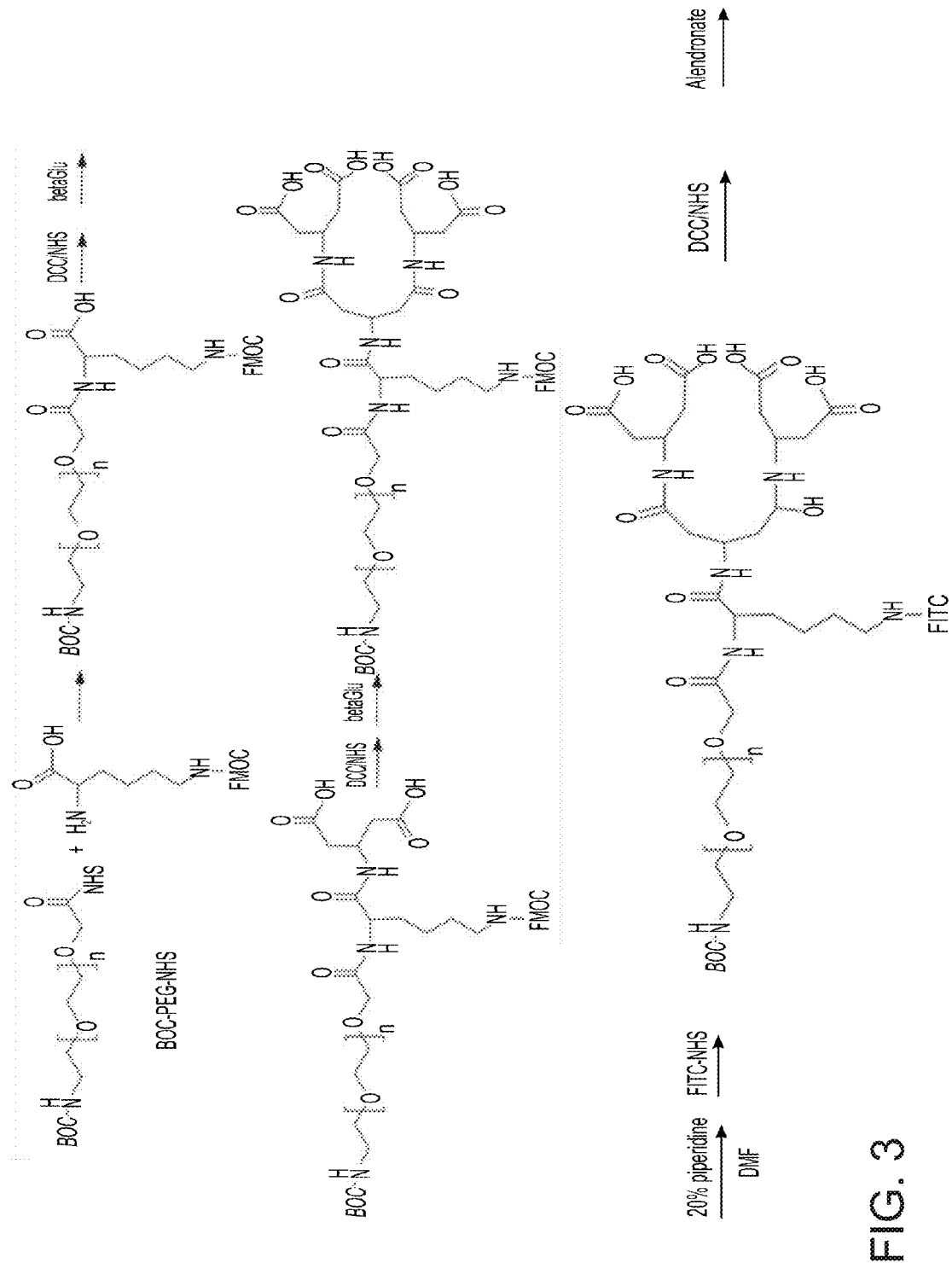
Figure 3:
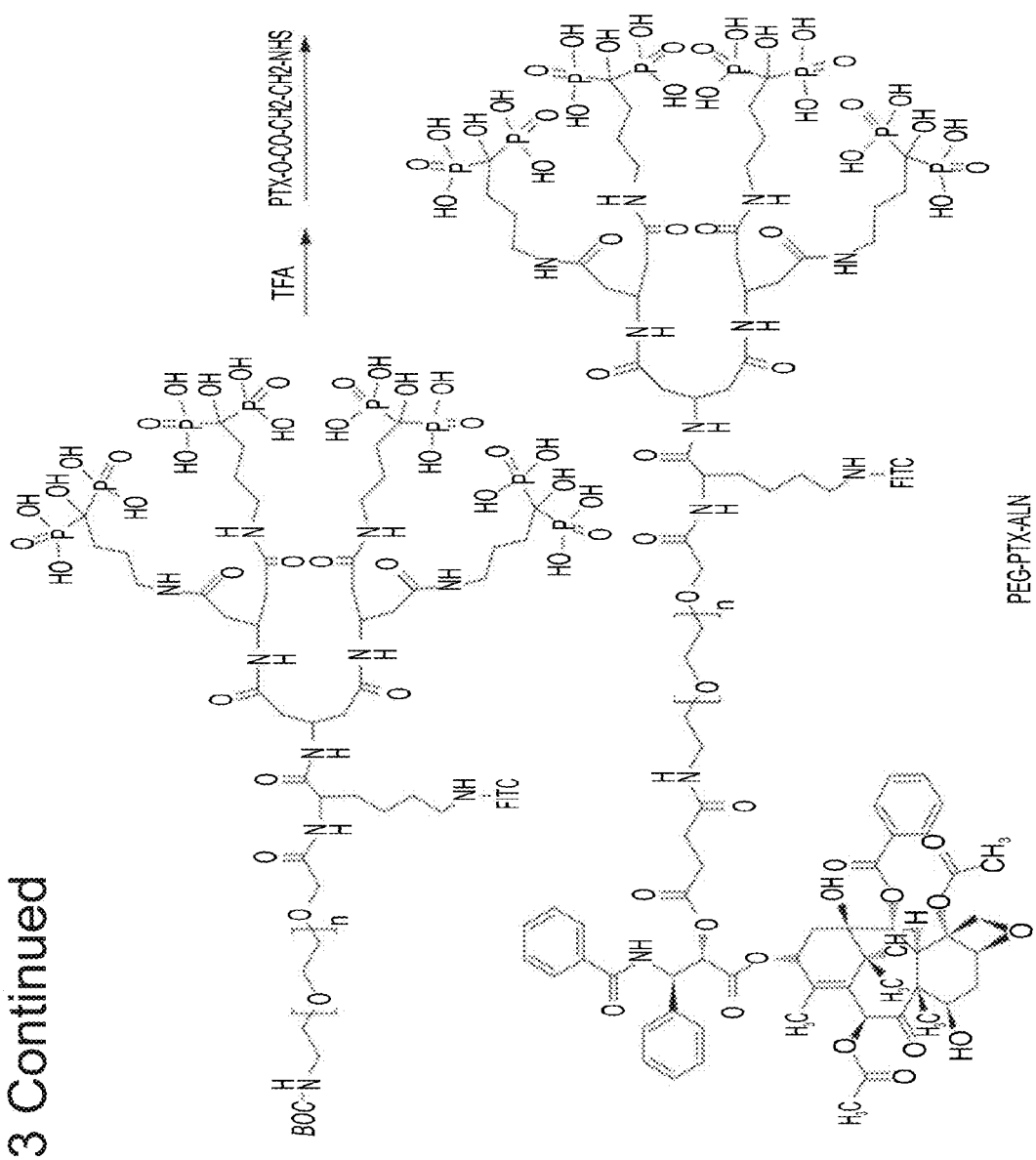

FIG. 3 presents a schematic illustration of an exemplary synthetic pathway for preparing FITC labeled-PTX-PEG-ALN conjugate (FITC labeled-Compound 3) according to some embodiments of the present invention.

FIGS. 4A-B are bar graphs presenting the mean hydrodynamic diameter of PTX-PEG (Compound 2; FIG. 3A) and PTX-PEG-ALN (Compound 3; FIG. 3B), as determined by a real time particle analyzer (NanoSight LM20™).

FIGS. 5A-B present comparative plots demonstrating the stability of the exemplary PTX-PEG-ALN conjugate, expressed as % of the conjugate out of the initial amount of the conjugate, following incubation in plasma (diamonds), at pH 7.4 (squares) and at pH 5 (triangles), as monitored by RP-HPLC, at the indicated time points (FIG. 5A); and the stability of the exemplary PTX-PEG-ALN conjugate following incubation at pH 7.4 (blank squares) and at pH 5 (black squares) and of the exemplary PTX-PEG conjugate following incubation at pH 7.4 (blank triangles) and at pH 5 (black triangles), expressed by the average micelles' size, as monitored by dynamic light scattering (Malvern Nano-S) (FIG. 5B).

Figure 6:
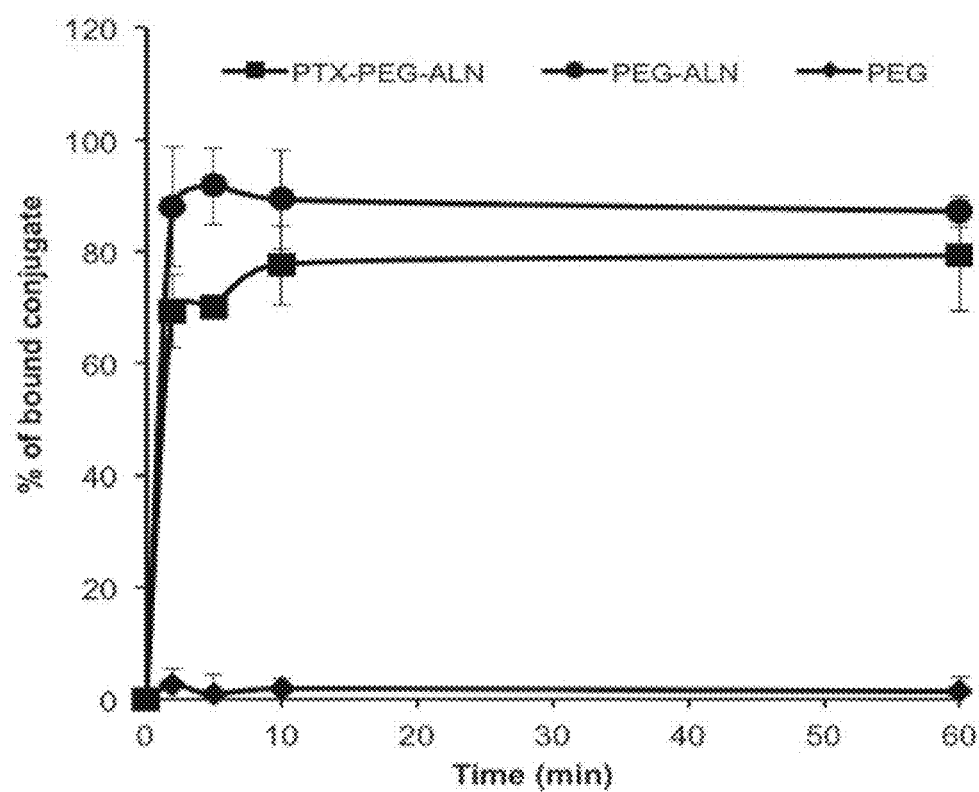

FIG. 6 presents plots demonstrating the binding kinetics of the exemplary conjugates PEG-ALN and PTX-PEG-ALN to the bone mineral HA, following incubation for 0, 2, 5, 10, and 60 minutes, as analyzed by FPLC.

Figure 7:
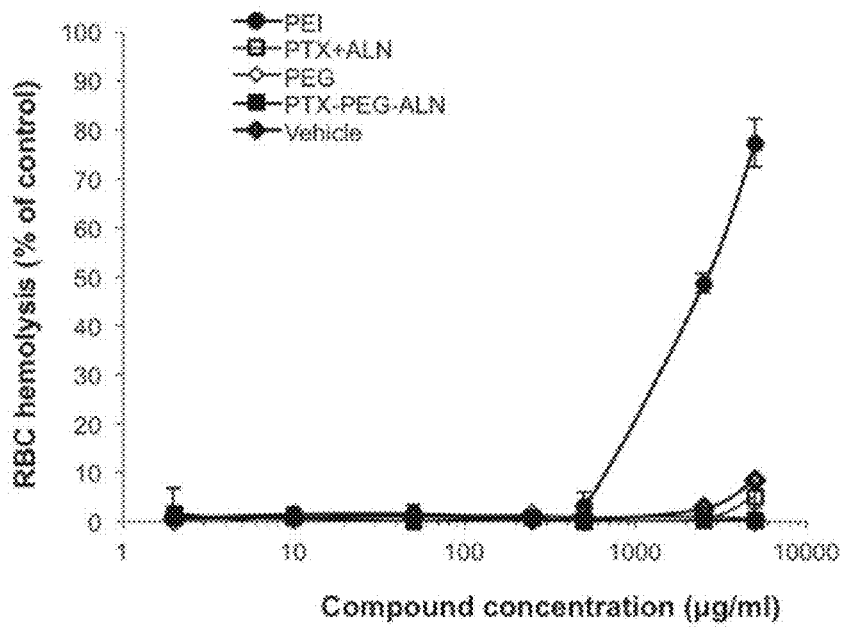

FIG. 7 presents plots demonstrating the effect of PTX-PEG-ALN (black squares), PEG (black diamonds), PEI (black circles), PTX vehicle (1:1:8 ethanol/Cremophor EL/saline, black diamonds), and a combination of PTX plus ALN as free drugs (blank squares) on hemolysis of rat red blood cells upon incubation for 1 hours at serial concentrations. Results are presented as % of hemoglobin release. Due to similar values, some symbols overlap.

Figure 8A:
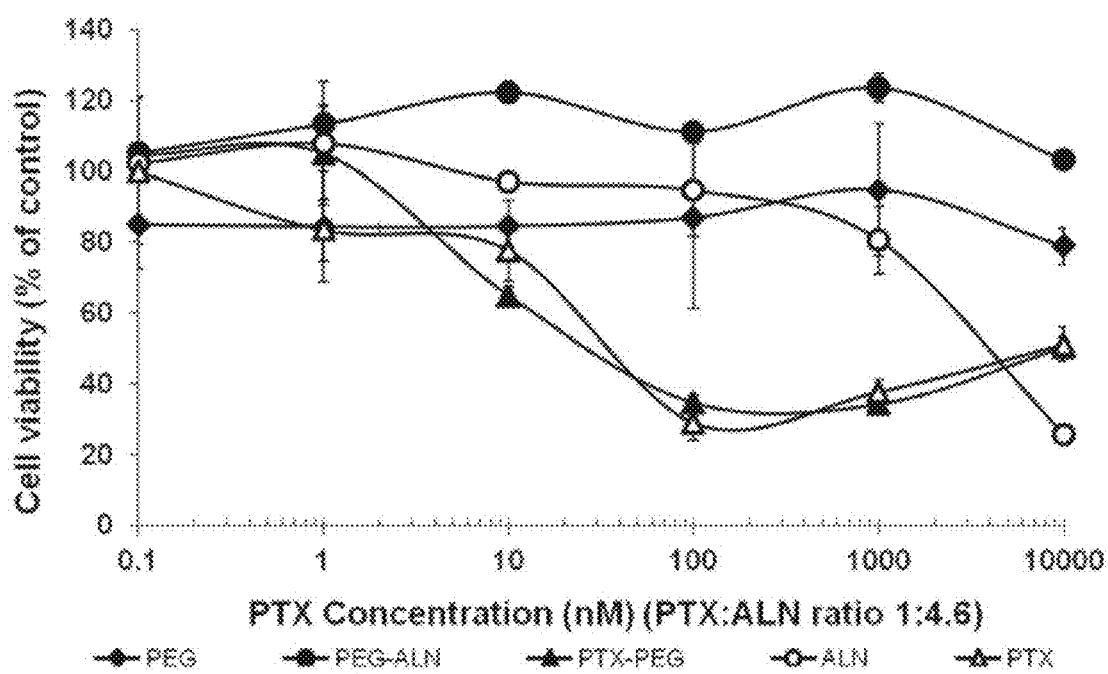

FIGS. 8A-B present comparative plots demonstrating the effect of various concentrations of PEG (black diamonds), the PEG-ALN conjugate as described herein (black circles), the PTX-PEG conjugate as described herein (black triangles), free PTX (blank triangles) and free ALN (blank circles) at equivalent concentrations (FIG. 8A) and of PEG (black diamonds), the PTX-PEG-ALN conjugate as described herein (black squares) and a combination of PTX and ALN as free drugs at equivalent concentrations (FIG. 8B), on PC3 cells, upon incubation for 72 hours. Data represent mean±s.d. X-axis is presented at a logarithmic scale.

FIG. 9 is a bar graph demonstrating a quantitative analysis of the effect of a combination of PTX and ALN as free drugs, free PTX, free ALN, PEG, a PTX-PEG-ALN conjugate as described herein, a PTX-PEG conjugate as described herein and a PEG-ALN conjugate as described herein, on the migration of PC3 cells, presented as % of migrated cells compared with control, untreated cells, following 2 hours incubation. Data represent mean±s.d.

Figure 10A:
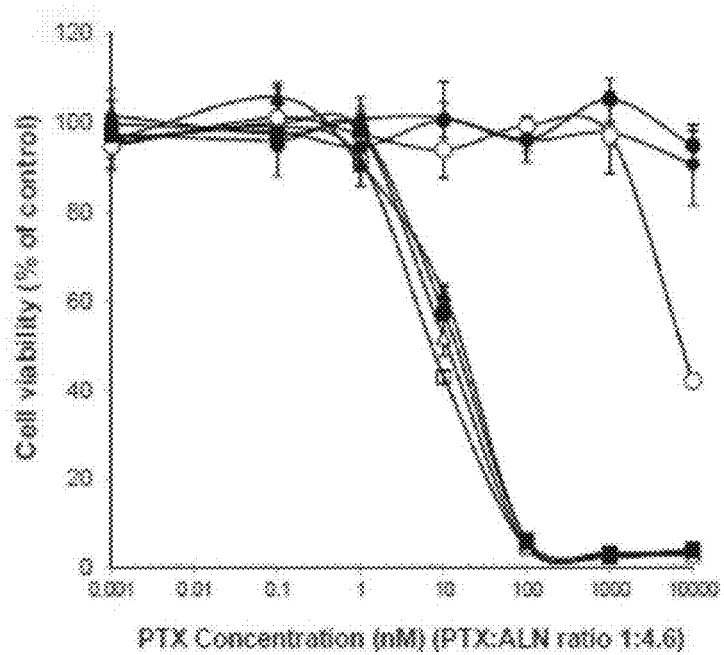
Figure 10B:
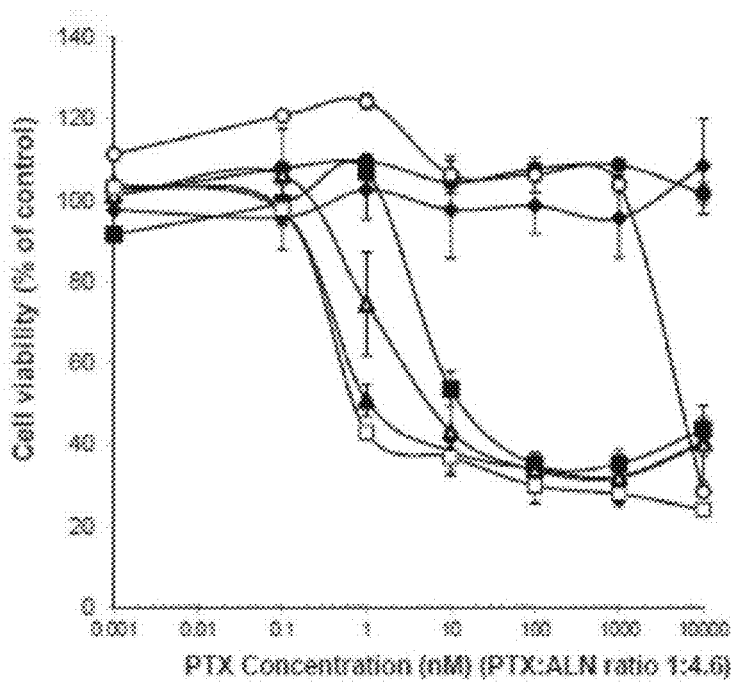

FIGS. 10A-B present comparative plots demonstrating the effect of various concentrations of a combination of PTX and ALN as free drugs (blank squares), free PTX (blank triangles), free ALN (blank circles), and equivalent concentrations of PEG (black diamonds), PTX-PEG-ALN (black squares), PTX-PEG (black triangles) and PEG-ALN (black circles) conjugates on the proliferation of murine 4T1 (FIG. 10A) and human MDA-MB-231 (FIG. 10B) mammary adenocarcinoma cell lines, following incubation for 72 hours. Data represent mean±s.d. X-axis is presented at a logarithmic scale.

Figure 11A:
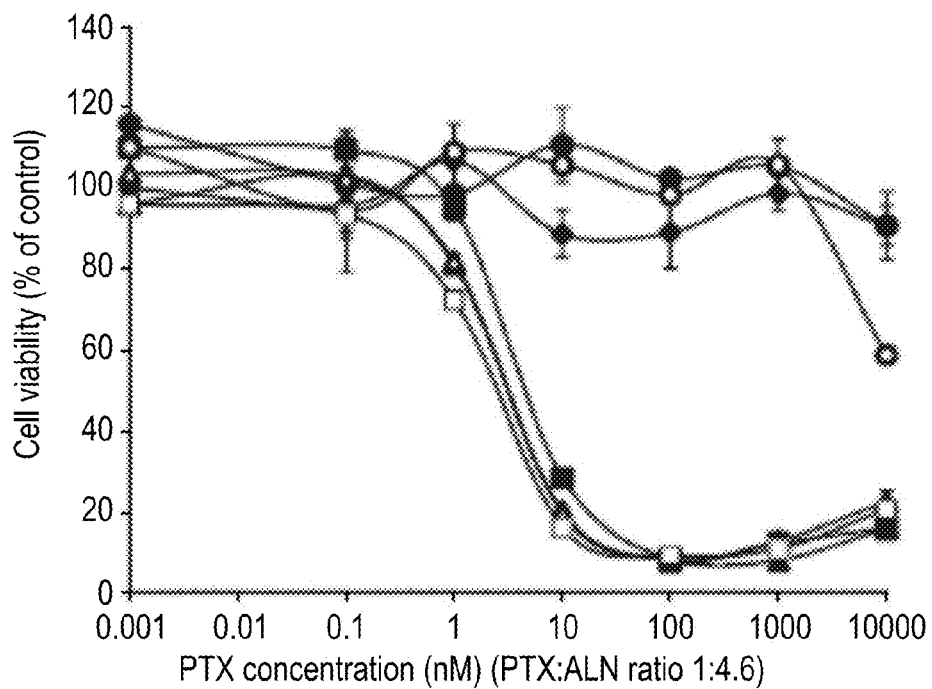
Figure 11B:
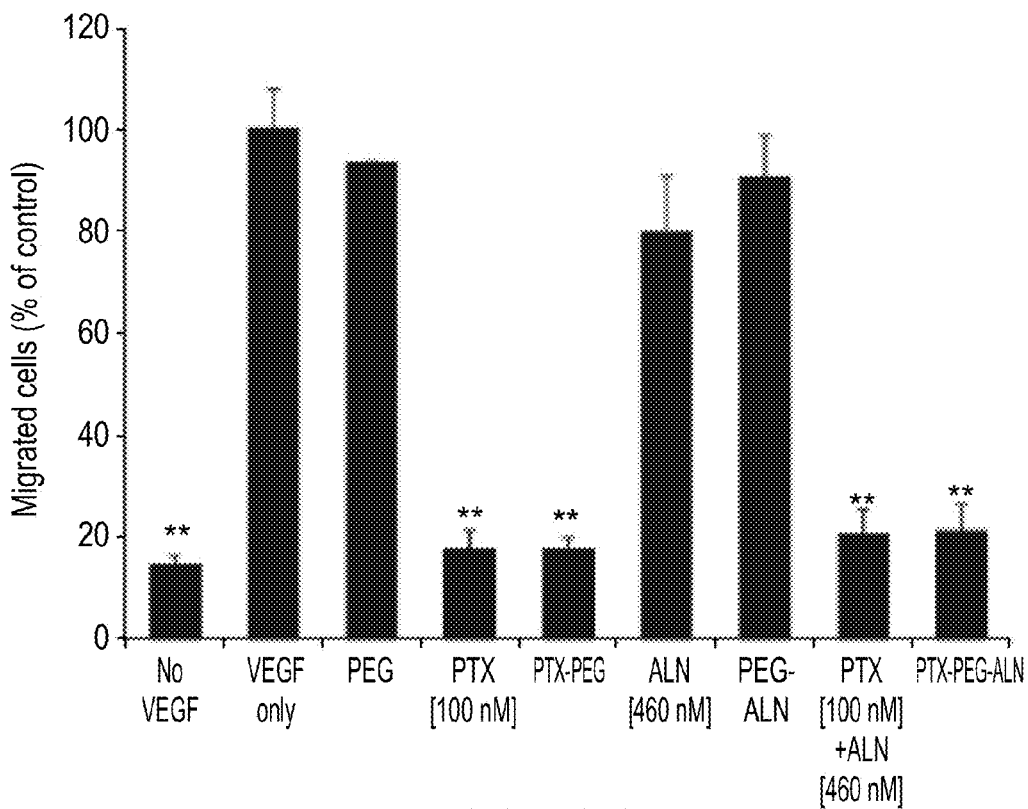

FIGS. 11A-B present comparative plots demonstrating the effect of various concentrations of a combination of PTX and ALN as free drugs (blank squares), free PTX (blank triangles), free ALN (blank circles), and equivalent concentrations of PEG (black diamonds), PTX-PEG-ALN (black squares), PTX-PEG (black triangles) and PEG-ALN (black circles) conjugates on the proliferation of HUVEC (FIG. 11A), wherein the X-axis is presented at a logarithmic scale (FIG. 11A); and the effect of these treatments on the migration of HUVEC towards the chemoattractant VEGF, wherein migration was normalized to percent migration with 100% representing migration to VEGF alone (FIG. 11B). The quantitative analysis of the number of migrated cells is presented.

Figure 12A:
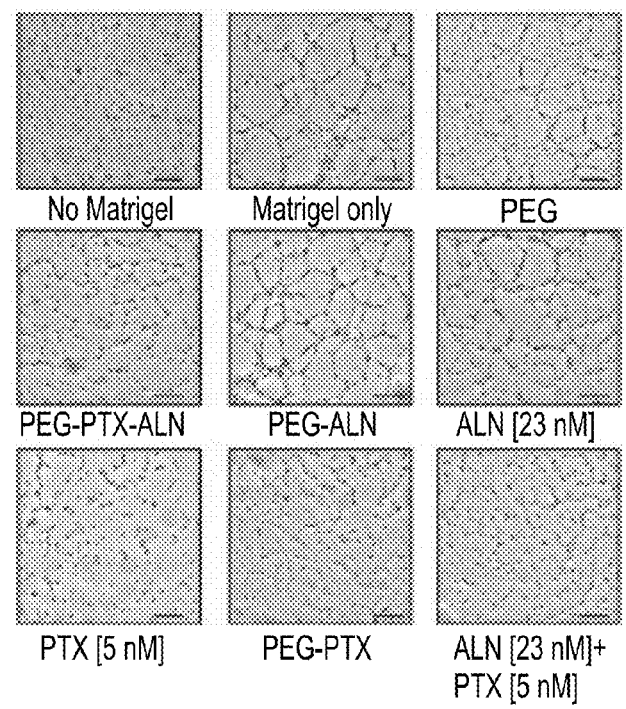
Figure 12B:
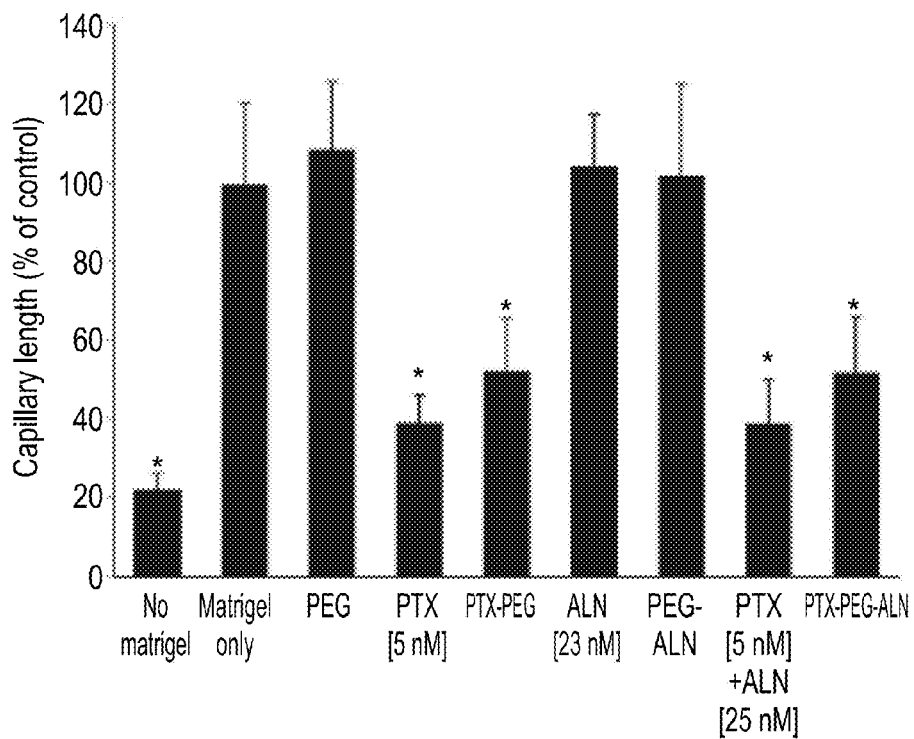

FIGS. 12A-B present representative images of capillary-like tube structures of HUVEC seeded on Matrigel® following treatment with a combination of PTX and ALN as free drugs, free PTX, free ALN, and equivalent concentrations of PEG, PTX-PEG-ALN, PTX-PEG and PEG-ALN conjugates (FIG. 12A; scale bar represents 100 µm); and a bar graph showing the effect of these treatments on the ability of HUVEC to form capillary-like tube structures as a quantitative analysis of the mean length of the tubes (FIG. 12B). Data represents mean±s.d. * $P<0.05$, ** $P<0.01$.

Figure 13A:
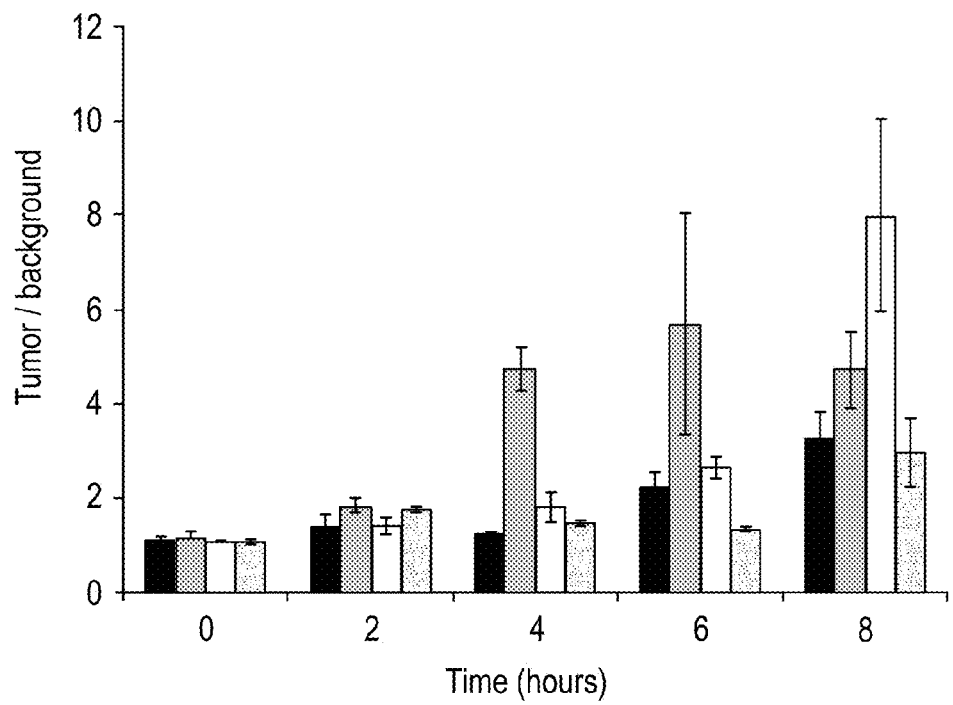
Figure 13B:
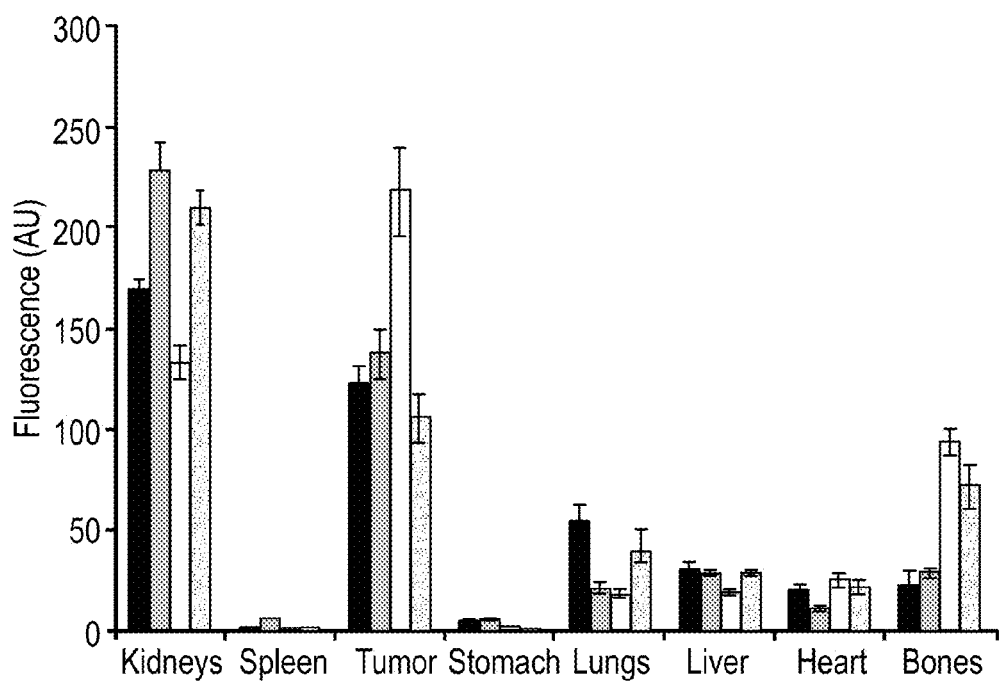

FIGS. 13A-B are bar graphs showing the biodistribution of FITC labeled-PEG (PEG Dendron; black), PTX-PEG (grey), PTX-PEG-ALN (white), and PEG-ALN (strips) conjugates, following intravenous injection to SCID mice bearing MDA-MB-231 human mammary tumors in the tibia, measured using the fluorescence non-invasive imaging system (CRI™ Maestro), and presenting semi-quantitative time dependent tumor accumulation profile of FITC-labeled conjugates in vivo, assessed as tumor/background (normal skin) ratios of florescence intensities of representative regions of interest (FIG. 13A), and ex vivo fluorescence intensities of tumors and organs resected 8 hours post treatment (FIG. 13B). Data represent mean±s.e.m.

Figure 14:
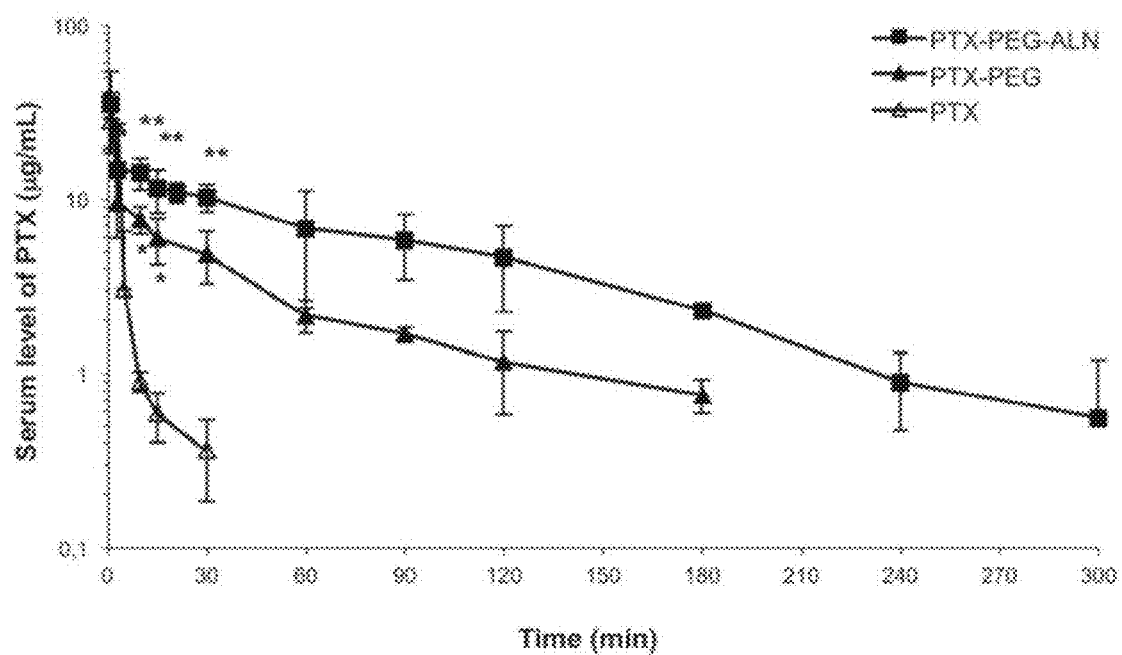

FIG. 14 presents comparative plots showing the pharmacokinetic profile of PTX in 1:1:8 Ethanol:Cremophor EL:Saline (blank triangles), of PTX-PEG conjugate in PBS pH=6 (black triangles), and of PTX-PEG-ALN conjugate in PBS pH=6 (black squares) (dose: 10 mg/Kg PTX equiv., n=10 animals per group) in female Balb/C mice. Each point is the mean of PTX serum level in animals (*=p<0.05 of PTX-PEG vs PTX; **=p<0.05 of PTX-PEG-ALN vs PTX). Y-axis is presented at a logarithmic scale.

FIGS. 15A-D present comparative plots showing the effect of intravenous administration of 15 mg/kg free PTX (blank triangles), 35 mg/kg free ALN (blank circles), a combination of ALN and PTX as free drugs (blank squares), of the PTX-PEG (black triangles), PEG-ALN (black circles), PTX-PEG-ALN (black squares) conjugates at equivalent concentrations and of saline (black diamonds) or PTX-vehicle (blank diamonds) as controls, every other day, to mice bearing 4T1-mCherry tumors in the tibia, as measured by intravital non-invasive fluorescence imaging of the tumors (FIG. 15A; scale bar represents 15 mm); the corresponding fluorescence images of 4T1-mCherry tumors in the tibia (FIG. 15B); comparative plots showing the percent body weight change from initial weight in mice following the indicated treatments at equivalent dose of the free drugs (FIG. 15C); and images showing the H&E histology staining of tumor sections of the saline control and the various treatment groups (FIG. 15D). * $P<0.05$ value of mice treated with PEG conjugates was analyzed against saline treated mice, P value of free PTX was analyzed against control mice treated with PTX-vehicle. Data represent mean±s.e.m. (n=6 mice per group).

Figures 16A, 16B:
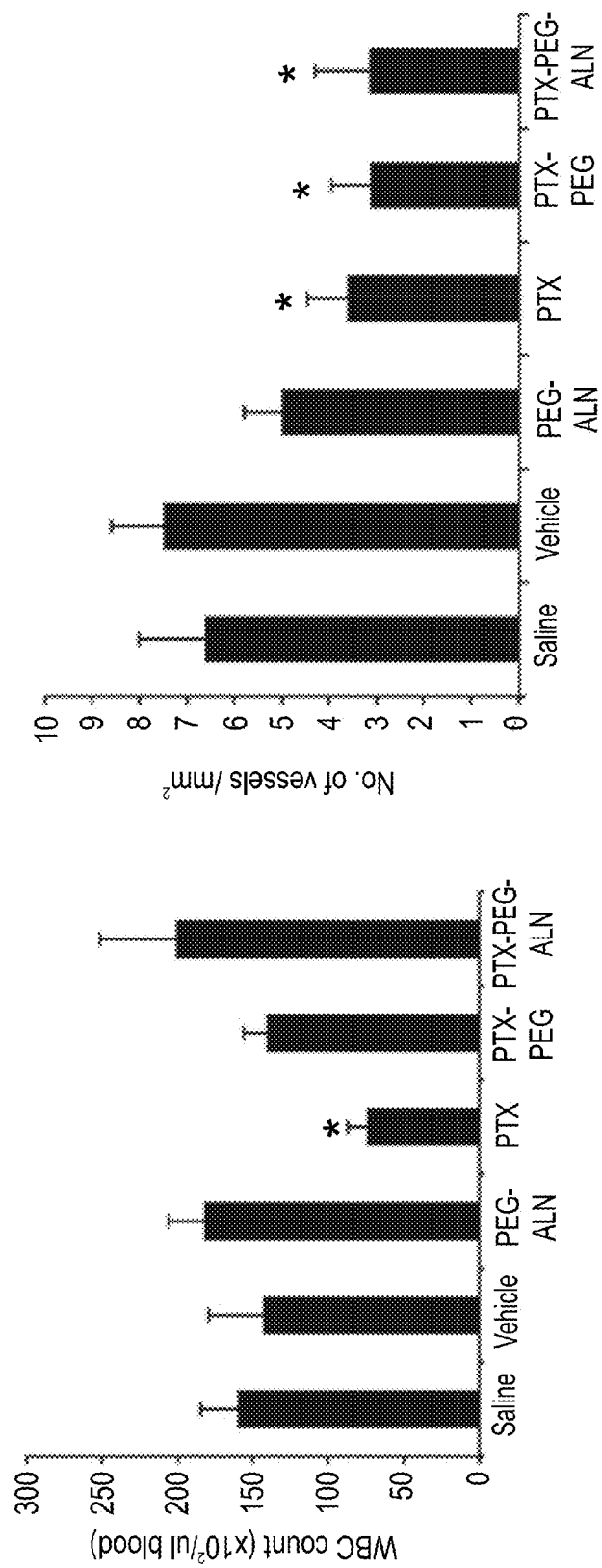

FIGS. 16A-B are bar graphs presenting WBC counts from blood samples collected on day 11 (FIG. 16A) and Micro Vessels Density (MVD) analysis assessed by vascular marker CD34 staining (FIG. 16B) in mice bearing 4T1-mCherry adenocarcinoma of the mammary in the tibia and treated by intravenous administration every other day of 15 mg/kg free PTX, and the conjugates PTX-PEG, PEG-ALN, PTX-PEG-ALN at equivalent concentrations and with saline or PTX-vehicle as controls. * $P<0.05$ value of mice treated with PEG conjugates was analyzed against saline treated mice, P value of free PTX was analyzed against control mice treated with PTX-vehicle. Data represent mean±s.e.m. (n=6 mice per group).

Figure 17A:
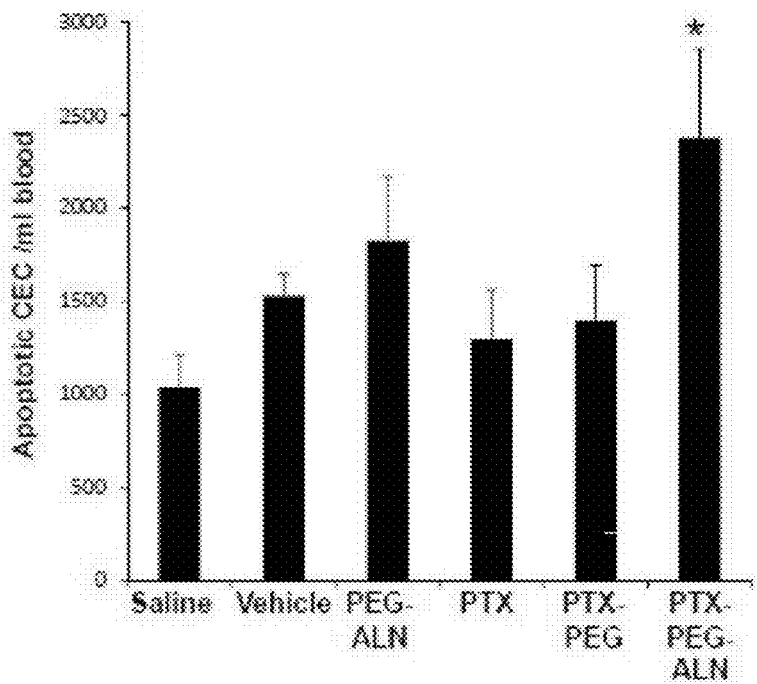
Figure 17B:
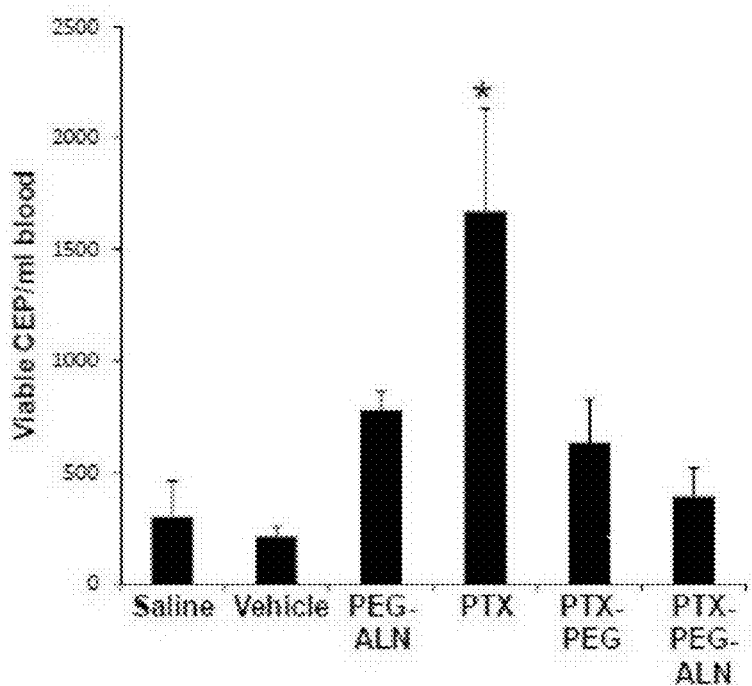

FIGS. 17A-B are bar graphs presenting the effect of intravenous administration, every other day, of 15 mg/kg free PTX, and of the PTX-PEG, PEG-ALN, PTX-PEG-ALN conjugates at equivalent PTX concentrations and of saline or PTX-vehicle controls, on the apoptotic CEC counts (FIG. 17A) and viable CEP levels (FIG. 17B) in mice bearing 4T1-mCherry tumors in the tibia, as measured using flow cytometry analysis performed on blood samples taken on day 11 of treatment. The calculation of the number of apoptotic CEC and viable CEP in peripheral blood was based on the WBC of each mouse. *$P<0.05$ value of mice treated with PEG-PTX-ALN conjugate was analyzed against saline control mice. Data represent mean±s.e.m. (n=6 mice per group).

Figure 18A:
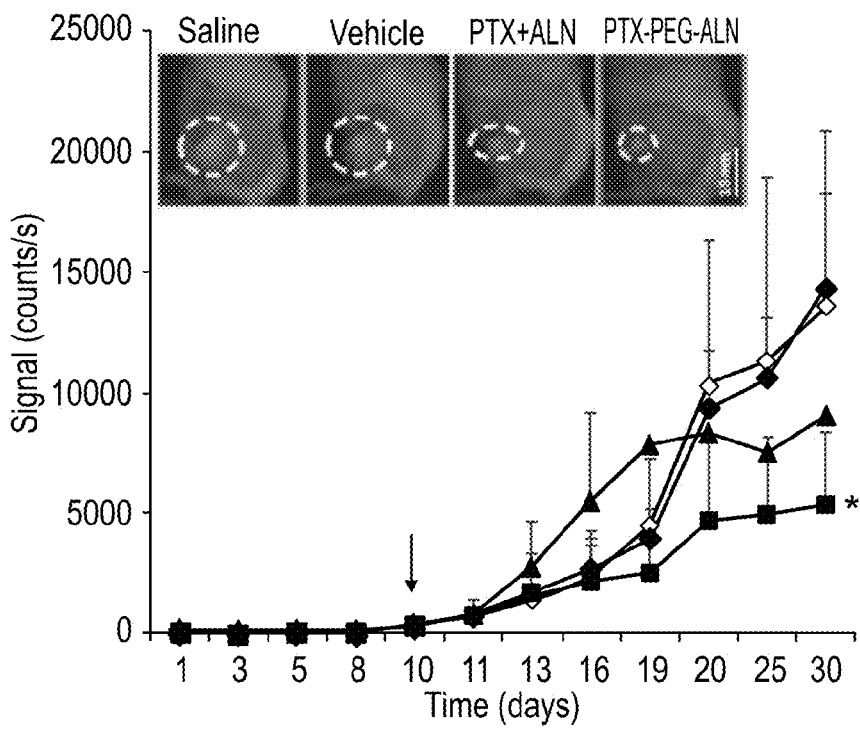
Figure 18B:
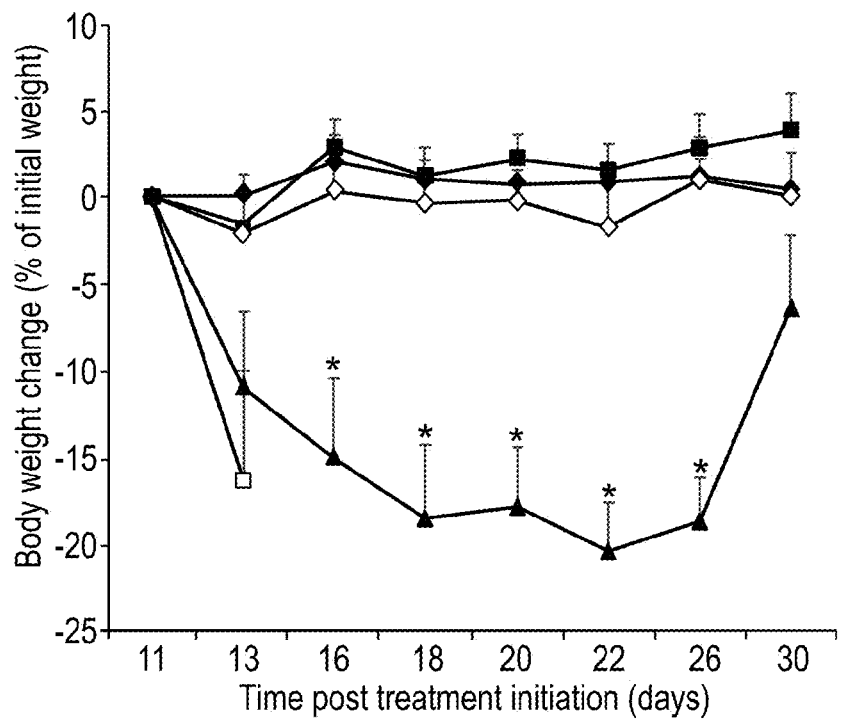
Figure 18D:
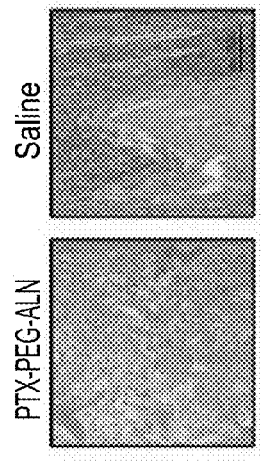

FIGS. 18A-D present comparative plots demonstrating the anti-tumor effect of intravenous administration, every other day, of a combination of 35 mg/kg free ALN and 15 mg/kg free PTX (blank squares), a combination of 17.5 mg/kg free ALN and 7.5 mg/kg free PTX (black triangles), and of the PTX-PEG-ALN conjugate (black squares) (dose: 15 mg/kg PTX and 35 mg/kg ALN equiv.), and of saline (black diamonds) or PTX-vehicle (blank diamonds) controls, as measured by intravital non-invasive fluorescence imaging of MDA-MB-231-mCherry tumors in the tibia (FIG. 18A), with the inset showing the obtained fluorescence images of the MDA-MB-231-mCherry tumors in the tibia on a scale bar of 15 mm; comparative plots showing the percent body weight change from initial weight in each of the tested groups (FIG. 18B); images showing H&E staining of tumor sections of the MDA-MB-231-mCherry-labeled tumors in the tibia in each of the tested groups (FIG. 18C); and images showing H&E staining of ossea medulla tumor sections of the saline control and PTX-PEG-ALN-treated mice (FIG. 18D). Data represent mean±s.e.m. (n=6 mice per group). *$P<0.05$ value of mice treated with PTX-PEG-ALN conjugate was analyzed against saline treated mice, P value of combination of free PTX plus ALN was analyzed against control mice treated with PTX-vehicle.

Figure 19B:
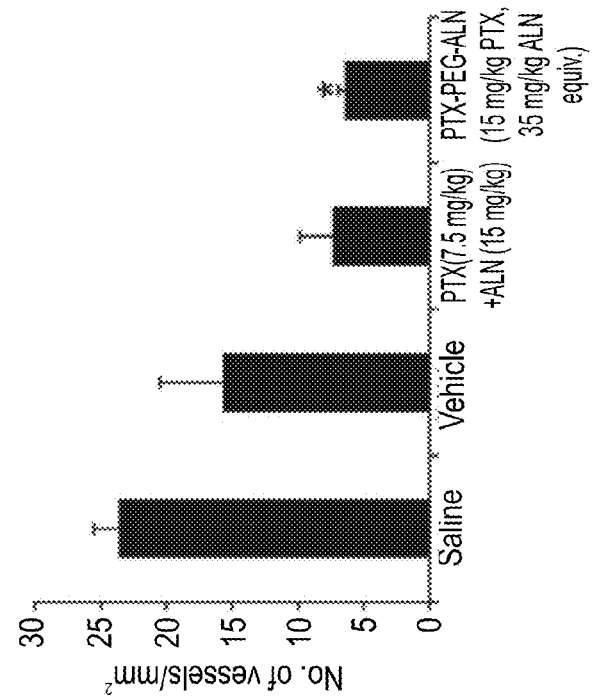
Figure 19A:
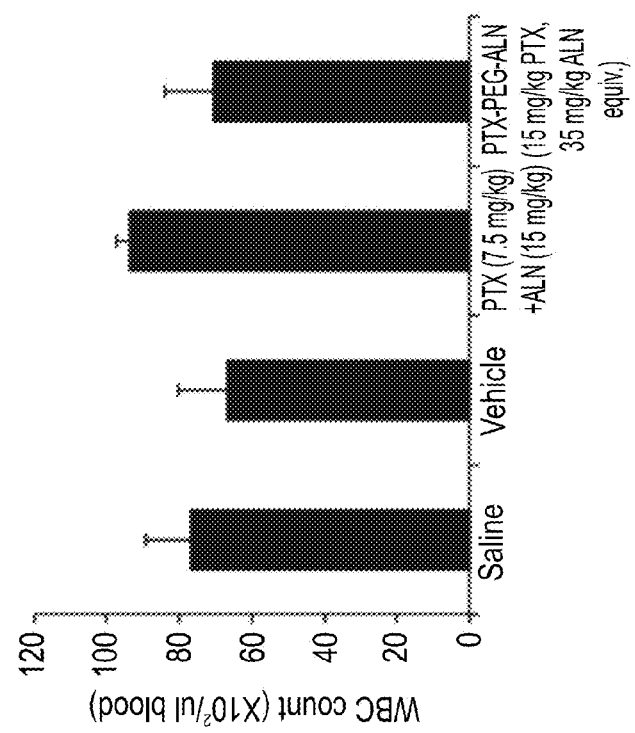

FIGS. 19A-B are bar graphs presenting WBC counts from blood samples collected on day 20 (FIG. 16A) and Micro Vessels Density (MVD) analysis assessed by vascular marker CD34 staining (FIG. 16B) in mice bearing MDA-MB-231-mCherry-labeled in the tibia and treated by intravenous administration every other day with a combination of 15 mg/kg free PTX and 35 mg/kg free ALN, a combination of 17.5 mg/kg free ALN and 7.5 mg/kg free PTX as free drugs, the PTX-PEG-ALN conjugate at equivalent concentrations and with saline or PTX-vehicle as controls. *$P<0.05$ value of mice treated with PTX-PEG-ALN conjugate was analyzed against saline treated mice, P value of a combination of free PTX and free ALN was analyzed against control mice treated with PTX-vehicle. Data represent mean±s.e.m. (n=6 mice per group).

Figures 20A, 20B:
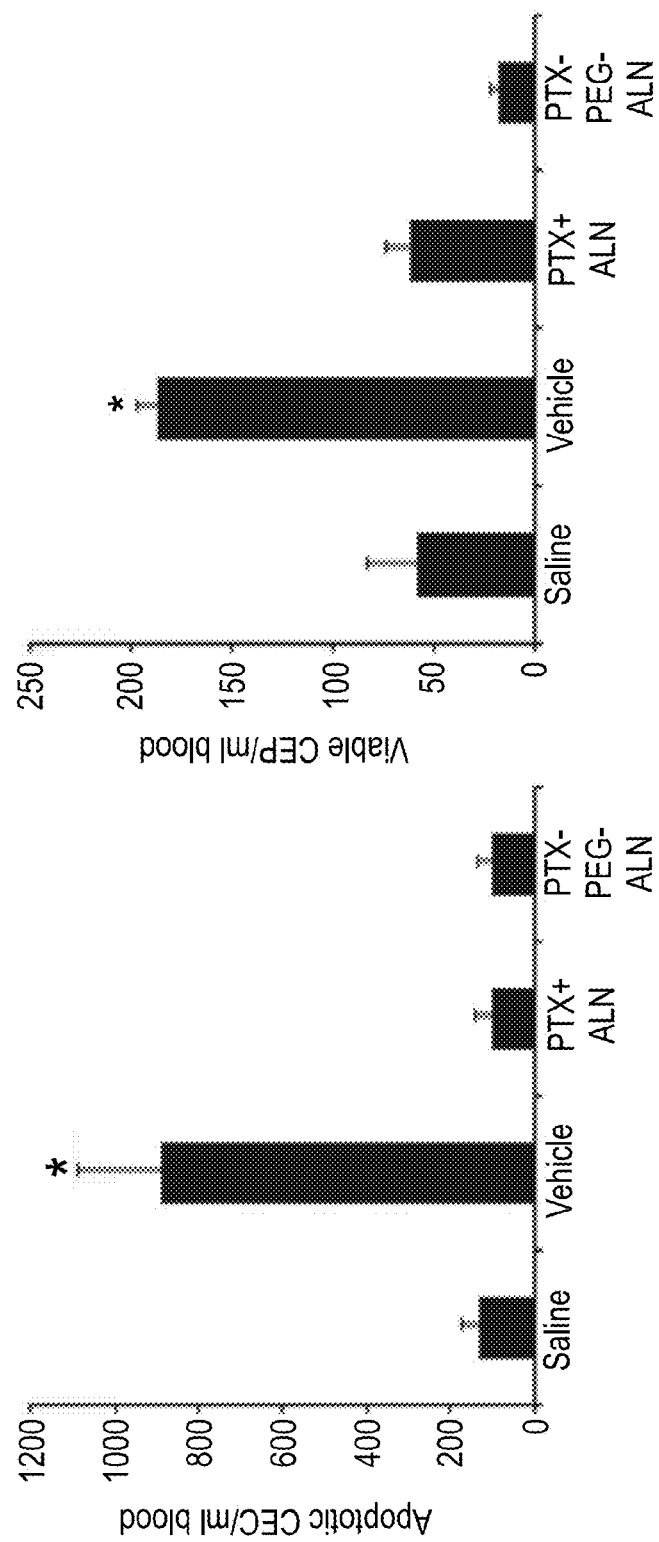

FIGS. 20A-B are bar graphs presenting the effect of intravenous administration, every other day, of a combination of 15 mg/kg free PTX and 35 mg/kg free ALN, of the PTX-PEG-ALN conjugate (dose: 15 mg/kg PTX and 35 mg/kg ALN equiv.), and of saline as control, on the apoptotic CEC counts (FIG. 20A) and viable CEP levels (FIG. 20B) in mice bearing MDA-MB-231-mCherry tumors in the tibia, as measured using flow cytometry analysis performed on blood sample taken on day 20 of treatment. The calculation of the number of apoptotic CEC and viable CEP in peripheral blood was based on the WBC of each mouse. *$P<0.05$ value of mice treated with PEG-PTX-ALN conjugate was analyzed against saline control mice. Data represent mean±s.e.m. (n=6 mice per group).

DESCRIPTION OF SPECIFIC EMBODIMENTS OF THE INVENTION

The present invention, in some embodiments thereof, relates to chemical conjugates and their use in therapy and/or diagnosis and, more particularly, but not exclusively, to bone-targeted polymeric conjugates and to uses thereof in monitoring and/or treating bone-related diseases and disorders.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, currently known agents for treating bone related cancer and other angiogenesis-related bone conditions, at doses where therapeutic activity is achieved, are characterized by high toxicity, which limits their use.

While reducing the present invention to practice, the present inventors have devised and successfully prepared and practiced novel conjugates, based on a heterobifunctional PEG-dendrimer (also referred to herein as PEG-dendron) such as, for example, $NH_2$—PEG-βGlu-(βGlu)$_2$-(COOH)$_4$, having attached thereto a bone targeting moiety and a therapeutically active agent. The present inventors have demonstrated that such conjugates can be obtained with a high degree of homogeneity, and a great control over the active agents' ratio, which can be pre-determined by defining the dendritic structure of the polymer.

The devised heterobifunctional PEG-dendrimer allows the subdivision of targeting and therapeutic functions by linking the therapeutic agent and the targeting agent at the two different end chains of the polymer. This design may lead to the obtainment of amphiphillic conjugates, in cases of a hydrophobic therapeutically active agent and a hydrophilic targeting moiety. The spatial separation of the active agents (therapeutically active agent and targeting moiety), besides offering the possibility to form self-assembled micelles, maintains all of the molecules of a hydrophilic targeting moiety exposed to the water, and thereby promptly available for binding to the desired target (e.g., a bone mineral).

The devised heterobifunctional PEG-dendrimer further allows obtaining a conjugate with a high degree of homogeneity, as it offers a great control over the ratio of the conjugated moieties and on the chemical structure of the conjugate. The optimal therapeutically active moiety/targeting moiety ratio can be selected by controllably growing the dendrimer structure. In addition, a high loading of a bone targeting moiety such as ALN, which has been reported to account for both rapid and elevated targeting to bone tumors and enhanced anti-angiogenic activity (see, for example, WO 2009/141827, can be achieved.

As demonstrated in the Examples section that follows, an exemplary PTX-PEG-ALN conjugate (see, FIG. 1, Compound 3) has been successfully synthesized and was shown to target bone neoplasms, possible by dual-targeting; through ALN (active mechanism), and by exploiting the EPR effect (passive mechanism). The building blocks of the conjugate (succinic acid, PEG and β-Glutamic acid) are all non-toxic, and no hemolytic activity was found to be exhibited by the conjugate (as opposed to the commercial solubilizing vehicle for PTX that contains Cremophor EL).

While devising exemplary polymeric conjugates, the present inventors have considered the high affinity of the conjugates to extracellular bone matrix, which can affect the conjugate internalization into cancer cells and consequently slow the rate of PTX release, in cases where such a release is designed to be lysosomotropic drug release (e.g., by using cathepsin-cleavable linking moieties which are susceptible to intracellular cathepsins). To this effect, exemplary conjugates were designed so as to exhibit a faster drug release and/or drug release in the surroundings of bone metastasis, where the conjugate will fast accumulate. This can be achieved either by linking the drug to the polymer through an ester or other hydrolytically-cleavable linkage, which releases the drug at physiological pH by simple hydrolysis, or via a linker that is cleavable by extracellular enzymes (e.g., enzymes which are present in extracellular matrix surrounding the bone).

Indeed, as demonstrated in the Examples section that follows, it has been shown for exemplary conjugates that the drug (PTX) is released by a hydrolytically-based mechanism without a significant contribution of esterases.

It has further been demonstrated the fast drug release at physiological pH affected also the stability of conjugate's micelles, which at such pH were stable up to about three hours. The pharmacokinetic profiles of exemplary conjugates in mice models showed marked half-lives increase with respect to free PTX solubilized in Cremophor EL (about 5 and 6 times longer, respectively), whereby the cytotoxicity of PTX was comparable to that of free PTX, thereby indicating that conjugating the drug does not reduce its therapeutic activity, yet results in reduced side effects compared to known PTX formulations.

As further demonstrated in the Examples section that follows, the effect of exemplary conjugates in inhibiting proliferation, capillary-like tube formation, and migration of endothelial cells suggested that these conjugates possess anti-angiogenic properties.

Biodistribution analysis demonstrated preferred accumulation in tumors in all FITC-labeled conjugates tested following 8 hours of injection, possibly as a result of the EPR effect. Exemplary conjugates were found to explicitly accumulate in the kidneys, due to renal excretion.

Exemplary conjugates according to some embodiments of the present invention showed substantial antitumor effects in both murine syngeneic and human xenograft mouse models tested. Additionally, the superiority of such conjugates was further evidenced by enhanced safety compared to the free drugs, without hindering bone-targeting affinity.

According to an aspect of some embodiments of the present invention there is provided a conjugate comprising a polymeric backbone having attached thereto a therapeutically active agent and a bone targeting moiety. In some embodiments, the therapeutically active agent and the bone targeting moiety are spatially separated by the polymeric backbone. In some embodiments, the therapeutically active agent is attached to one end of the polymeric backbone (e.g., to a terminus backbone unit at one end of the polymeric backbone) and the bone targeting moiety is attached to another end of the polymeric backbone (e.g., to a terminus backbone unit at another end of the polymeric backbone). In some embodiments, the bone targeting moiety is attached to the polymeric backbone (e.g., to a terminus backbone unit of the polymeric backbone) via a branching unit, such that a mol ratio of the bone targeting moiety to said polymer and is at least 2:1.

The conjugates described herein can also be referred to as polymeric conjugates.

The Polymeric Backbone:

As used herein, the phrase "polymeric backbone" describes a plurality of backbone units that are covalently linked to one another. The backbone units and hence the polymeric backbone are those present in a polymer from which the conjugate is derived from.

By "derived from" it is meant that the polymeric backbone is the same as the polymer from which it is derived, except for having the moieties as described herein conjugated thereto (optionally via the branching unit, linking moiety and/or spacer, as described herein).

As used herein, the term "polymer" describes a substance, preferably an organic substance, but alternatively an inorganic substance, composed of a plurality of repeating structural units (referred to interchangeably as backbone units or monomeric units) covalently connected to one another and forming the polymeric backbone of the polymer. The term "polymer" as used herein encompasses organic and inorganic polymers and further encompasses one or more of a homopolymer, a copolymer or a mixture thereof (a blend). The term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone units can differ from one another by the pendant groups thereof.

For the sake of simplicity, the terms "polymer" and "polymeric backbone" as used hereinthoroughout interchangeably, relate to both homopolymers, copolymers and mixtures thereof.

In some embodiments, the polymeric conjugates described herein are composed of a polymeric backbone, formed from a plurality of backbone units that are covalently linked to one another. The therapeutically active agent and the bone targeting moiety are each attached, directly or indirectly, to a different end of the polymeric backbone, e.g., to a different terminus backbone unit of the polymeric backbone. Thus, in some embodiments, the therapeutically active agent and the bone targeting moiety are spatially separated from one another by the polymeric backbone.

By "terminus backbone unit" it is meant a backbone unit at the end of the polymeric chain, which is attached only to one other backbone unit of the polymer (and not to two backbone units, as do all other backbone units in the polymeric backbone). In some embodiments, the targeting moiety and the therapeutically active agent are each attached to the terminus backbone unit either directly or indirectly, while utilizing a functional group that forms a part of the terminus backbone unit, or which is generated within, or attached to, the terminus backbone unit, in order to facilitate the attachment.

A polymeric conjugate as described herein therefore comprises, in some embodiments, a polymeric backbone which comprises a plurality of backbone units being the same (in case of a homopolymer) or different (in case of a copolymer), wherein all of these backbone units, except for the terminus backbone units at each end of the backbone, are non-functionalized, namely, do not have any of a therapeutically active agent, a labeling agent and/or a targeting moiety attached thereto and do not bear any functional group that can be utilizing for attaching a therapeutically active agent, a labeling agent and/or a targeting moiety, either directly or indirectly, thereto.

Polymers which are suitable for use in the context of the present embodiments are biocompatible, non-immunogenic and non-toxic. The polymers serve as carriers that enable specific delivery into tumor tissue, possibly due to the EPR effect discussed herein.

The polymer may be a biostable polymer, a biodegradable polymer or a combination thereof (in case of a copolymer).

The term "biostable", as used in this context of embodiments of the invention, describes a compound or a polymer that remains intact under physiological conditions (e.g., is not degraded in vivo, and hence is non-biodegradable or non-biocleavable).

The term "biodegradable" describes a substance which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

In some embodiments, the polymer is a biostable polymer, as defined herein. Such polymers may allow designing the polymeric conjugate so as to selectively release the therapeutically active agent at the desired bodily site (e.g., a bone tissue), as biodegradation of the polymer before it reaches the desired site is avoided.

The polymers can be water-soluble or water-insoluble. In some embodiments, the polymers are water soluble at room temperature.

In some embodiments, the polymer is an amphiphillic polymer.

The polymers can further be charged polymers or non-charged polymers. Charged polymers can be cationic polymers, having positively charged groups and a positive net charge at a physiological pH; or anionic polymers, having negatively charged groups and a negative net charge at a physiological pH. Non-charged polymers can have positively charged and negatively charged group with a neutral net charge at physiological pH, or can be no charge at all.

In some embodiments, the polymer has an average molecular weight in the range of 100 Da to 800 kDa. In some embodiments, the polymer has an average molecular weight lower than 60 kDa. In some embodiments, the polymer's average molecular weight range is 10 to 60 kDa, or 15 to 60 kDa, or 10 to 40 kDa or 15 to 40 kDa. Any intermediate range or value is also contemplated.

Polymeric substances that have a molecular weight higher than 10 kDa typically exhibit an EPR effect, as described herein, while polymeric substances that have a molecular weight of 100 kDa and higher have relatively long half-lives in plasma and an inefficient renal clearance. Accordingly, a molecular weight of a polymeric conjugate can be determined while considering the half-life in plasma, the renal clearance, and the accumulation in the tumor of the conjugate.

The molecular weight of the polymer can be controlled, at least to some extent, by the degree of polymerization (or co-polymerization). Optionally, commercially available polymers, which have a desired molecular weight, are utilized.

The polymer used in the context of embodiments of the invention can be a synthetic polymer or a naturally-occurring polymer. In some embodiments, the polymer is a synthetic polymer.

Exemplary polymers which are suitable for use in the context of the present embodiments include, but are not limited to, poly(alkylene glycol)s, poly(2-alkyl-2-oxazoline)s, dextran, water soluble polyamino acids, a polyglutamic acid (PGA), a polylactic acid (PLA), a polylactic-co-glycolic acid (PLGA), a poly(D,L-lactide-co-glycolide) (PLA/PLGA), a poly(hydroxyalkylmethaacrylamide), a polyglycerol, a polyamidoamine (PAMAM), and a polyethylenimine (PEI).

In some embodiments, the polymer is an amphiphilic, biostable, biocompatible and immunogenic polymer. Exemplary such polymers include, but are not limited to, a poly(alkylene glycol), a poly(2-alkyl-2-oxazoline), and a copolymer comprising a poly(alkylene glycol) and/or a poly(2-alkyl-2-oxazoline).

In some embodiments, a suitable polymer for use in the context of the present embodiments can be represented by the following general Formula:

$$ZWx\text{-}\{[(CRxRy)k]\text{-}W\}n\text{-}[(CRxRy)k]\text{-}WyL$$

wherein:

k is an integer from 1 to 6, preferably from 2 to 4, more preferably being 2 or 3, representing the number of carbon atoms (the length) in each backbone unit;

n is an integer from 100 to 1000, representing the number of backbone units in the polymer, and is preferably selected or determined in accordance with a desired molecular weight of the polymer, as outlined hereinabove;

Z and L are each independently a group at an end of the polymer, and can be hydrogen, alkyl, cycloalkyl, aryl, alkoxy, thioalkoxy, aryloxy, thioaryloxy, carbonyl, thiocarbonyl, and can also be selected from the group consisting of carbamate, thiocarbamate, guanyl, guanidine, hydrazine, hydrazide, and the like;

W, Wx and Wy are each independently a heteroatom-containing group selected from the group consisting of oxygen, sulfur, NRw, PRw, and SiRwRz, and is preferably selected from the group consisting of oxygen, sulfur or NRw; and Rz, Ry, Rw and Rz are each independently selected from the group consisting of hydrogen, alkyl, cycloalkyl, aryl, alkoxy, thioalkoxy, aryloxy, thioaryloxy, carbonyl, thiocarbonyl, and can also be selected from the group consisting of oxo, carbamate, thiocarbamate, guanyl, guanidine, hydrazine, hydrazide, as long as the substituent(s) do not interfere with the binding of, and/or are reactive with, the bone targeting moiety and/or the therapeutically active moiety.

The group [(CRxRy)k]-W represents the repeating backbone unit in the polymer. In some embodiments, all of the backbone units are the same. Optionally, the backbone units are different from one another by the heteroatom W, the RxRy substituents, the value k, or both.

In exemplary embodiments, at least 50% of the backbone units are identical, e.g., they comprise the same heteroatoms and the same k values as one another, and may further by identically substituted. Optionally, at least 70%, optionally at least 90%, and optionally 100% of the backbone units are identical.

The group WxZ and WyL represent the functional groups at the ends of the polymer. In cases where W, Wx and WY are the same and Z and L are each hydrogen, the polymer is considered as being functionalized by the intrinsic functionalities of the repeating units (e.g., it terminated by groups such as —OH, NHR, and the like. In some embodiments, the polymer can be modified so as to include groups that are not derived from the repeating units, for example, by replacing an and functional hydroxy group which is present when each of W, Wx and Wy is hydrogen, by an amine or any other group.

In some embodiments, in any of the above-described embodiments of a polymer, W is O, such that the polymer is a poly(alkylene glycol).

The phrase "poly(alkylene glycol)", as used herein, encompasses a family of polyether polymers which share the following general formula: 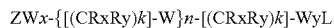, wherein k represents the number of methylene groups present in each alkylene glycol unit, and n represents the number of repeating units, and therefore represents the size or length of the polymer. Optionally, k varies among the units of the poly(alkylene glycol) chain. For example, a poly(alkylene glycol) chain may comprise both ethylene glycol (k=2) and propylene glycol (k=3) units linked together.

When Rx and Ry are each hydrogen and m is 2, the polymer is a poly(ethylene glycol) (PEG).

The WxZ and WyL groups can each be hydroxy (OH) groups, or can be modified such that the PEG is modified so as to include other functional groups at one or both ends thereof.

In some embodiments, W in NRw, and Rw is a carbonyl, as defined herein, such that the polymer is a poly(2-alkyl-2-oxazoline) or an analog thereof. By "analog" of a poly(2-alkyl-2-oxazoline), it is meant that the carbonyl can be replaced by a thiocarbonyl and/or the alkyl can be replaced by a cycloalkyl or aryl.

The WxZ and WyL groups can each be NHRw groups, as defined herein for these embodiments, or can be modified such that the poly(2-alkyl-2-oxazoline) is modified so as to include other functional groups at one or both ends thereof.

These polymers can be of any molecular weight, as described herein.

These polymers can also form a part of a copolymer, which further comprise backbone units of another polymer. The backbone units of another polymer can be interdispersed between the backbone units as described herein, or a chain of backbone units of one type of a polymer can be linked at one or both ends to a chain of backbone units of another polymer.

An exemplary suitable copolymer of a poly(alkylene glycol) is a copolymer of PEG and PGA.

It is to be noted that the description provided herein for the term "polymer" refers to those polymers from which the polymeric backbone unit in the conjugates described herein is derived. However, in the herein described conjugates, the terminus backbone units in each end of the polymeric backbone is utilized for attaching thereto the bone targeting moiety and the therapeutically active agent, and thus these terminus backbone units are derivatized so as to have these moieties attached thereto, either directly or indirectly, and hence possess at least some different structural properties.

In some embodiments, the WxZ and WyL groups is the Formula described hereinabove, or any other reactive group at the polymer's ends, is utilized for attaching, either directly or indirectly, the therapeutically active moiety or the bone targeting moiety.

In some embodiments, a functional group at one end of the polymeric backbone is used per se for attaching the bone targeting moiety and/or the group at the other end of the polymer is used per se for attaching the therapeutically active agent.

In some embodiments, one or both end groups are modified so as to facilitate the attachment of the therapeutically active moiety and/or the bone targeting moiety, and/or to include a desirable linking moiety, as is further detailed herein.

The Therapeutically Active Agent:

As used herein, a "therapeutically active agent" encompasses any agent that is capable of exhibiting a beneficial therapeutic effect, such as treating or preventing a medical condition, a disease or a disorder, as defined herein. The terms "therapeutically active agent" and "drug" are used herein interchangeably.

In some embodiments, the therapeutically active agent attached to one end of the polymeric backbone (e.g., one of the terminus backbone units), is such that exhibits a therapeutic effect in the environment of a bone tissue. Thus, in some embodiments, the therapeutically active agent is such that is suitable for treating a bone-related disease or disorder, as defined hereinafter.

In some embodiments, the therapeutically active agent is an anti-angiogenesis agent.

The phrase "anti-angiogenesis agent", which is also referred to herein, interchangeably as "anti-angiogenic agent" or "angiogenesis inhibitor", describes an agent having the ability to (a) inhibit endothelial cell proliferation or migration, (b) kill proliferating endothelial cells, and/or (c) inhibit the formation of new blood vessels in a tissue (e.g., a tumor tissue).

Exemplary anti-angiogenesis agents that are suitable for use in the context of embodiments of the invention include, but are not limited to, paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, a matrix metalloproteinase, penicillamine, PTK787/ZK 222584, RPI.4610, squalamine lactate, SU5416, thalidomide, TNP-470, combretastatin, tamoxifen, COL-3, neovastat, BMS-275291, SU6668, anti-VEGF antibody, Medi-522 (Vitaxin II), CAI, Interleukin-12, IM862, Amilloride, Angiostatin® Protein, Angiostatin K1-3, Angiostatin K1-5, Captopril, DL-alpha-Difluoromethylornithine, DL-alpha-Difluoromethylornithine HCl, His-Tag® Endostatin™ Protein, Fumagillin, Herbimycin A, 4-Hydroxyphenylretinamide, Juglone, Laminin, Laminin Hexapeptide, Laminin Pentapeptide, Lavendustin A, Medroxyprogesterone, Medroxyprogesterone Acetate, Minocycline, Minocycline HCl, Placental Ribonuclease Inhibitor, Suramin, Sodium Salt Suramin, Human Platelet Thrombospondin, Neutrophil Granulocyte, monoclonal antibodies directed against specific proangiogenic factors and/or their receptors (e.g. Avastin, Erbitux, Vectibix, Herceptin); small molecule tyrosine kinase inhibitors of multiple proangiogenic growth factor receptors (e.g. Tarceva, Nexavar, Sutent, Iressa); inhibitors of mTOR (mammalian target of rapamycin) (e.g. Torisel); interferon alpha, beta and gamma; IL-12; matrix metalloproteinases (MMP) inhibitors (e.g. COL3, Marimastat, Batimastat); EMD121974 (Cilengitide); Vitaxin; Squalamin; COX-2 inhibitors; PDGFR inhibitors (e.g., Gleevec); NM3 and 2-ME2.

As used herein, the term "COX-2 inhibitor" refers to a non-steroidal drug that relatively inhibits the enzyme COX-2 in preference to COX-1. Preferred examples of COX-2 inhibitors include, but are no limited to, celecoxib, parecoxib, rofecoxib, valdecoxib, meloxicam, and etoricoxib.

In some embodiments, the anti-angiogenesis agents is selected from the group consisting of TNP-470, Paclitaxel, monoclonal antibodies directed against specific proangiogenic factors and/or their receptors (e.g. Avastin, Erbitux, Vectibix, Herceptin); small molecule tyrosine kinase inhibitors of multiple proangiogenic growth factor receptors (e.g. Tarceva, Nexavar, Sutent, Iressa); inhibitors of mTOR (mammalian target of rapamycin) (e.g. Torisel); interferon alpha, beta and gamma; IL-12; matrix metalloproteinases (MMP) inhibitors (e.g. COL3, Marimastat, Batimastat); EMD121974 (Cilengitide); Vitaxin; Squalamin; COX-2 inhibitors; PDGFR inhibitors (e.g., Gleevec); NM3; and 2-ME2.

In some embodiments, the anti-angiogenesis agent is Paclitaxel.

The microtubule-interfering agent Paclitaxel is a drug commonly used for the treatment of advanced metastatic breast cancer. However, it is neurotoxic, it causes hematological toxicity and many breast tumors develop resistance thereto. It has been recently shown that Paclitaxel at ultra low doses inhibits angiogenesis. However, Paclitaxel is poorly soluble and the excipients Cremophor EL or ethanol used today to solubilize its commercial form, cause hypersensitivity reactions.

Alternatively, the therapeutically active agent can be an anti-cancer agent (anti-neoplastic agent) that acts via other mechanism of action (namely, not via inhibition of angiogenesis). Such agents include, but are not limited to, alkylating agents, antimetabolites and antitumor antibiotics, as these are known for any person skilled in the art.

The Linking Moiety:

Since the conjugates as described herein are aimed at releasing the therapeutically active agent at the diseased bodily site, in some embodiments, the therapeutically active agent is attached to the polymer via a biocleavable moiety. The biocleavable moiety can be a biocleavable bond or a biocleavable linking group.

In some embodiments, the therapeutically active agent is attached to the terminus backbone unit of the polymeric backbone directly via a bond, preferably via a biocleavable bond, and preferably via a hydrolytically-cleavable bond, as defined herein.

In some embodiments, the therapeutically active agent is linked to the end of the polymeric backbone (e.g., to a terminus backbone unit of the polymeric backbone) directly, or indirectly (e.g., via a spacer), through a linking moiety (also referred to herein as a linker, a linker group a linker moiety or a linking group), whereby, in some embodiments, the direct/indirect linkage is designed as being cleavable at conditions characterizing the desired bodily site, as detailed hereinbelow.

The linking moiety linking the therapeutically active agent to the polymer is also referred to herein as a first linking moiety, and, in the representative Formula I hereinbelow, is represented as $L_1$.

The linking moiety described herein refers to a chemical moiety that serves to couple the therapeutically active agent to the polymeric backbone while not adversely affecting the therapeutic effect of agent.

In some embodiments, the linking moiety is a biodegradable (or biocleavable) linking moiety.

The phrase "biodegradable linking moiety", as used herein, describes a linker that is capable of being degraded, or cleaved, when exposed to physiological conditions. Such physiological conditions can be, for example, an aqueous environment, pH, a certain enzyme, and the like.

Accordingly, according to some embodiments, the biodegradable linker is a hydrolytically-cleavable linking moiety, a pH-sensitive linker or an enzymatically-cleavable linker.

In some embodiments, the biodegradable linking moiety is a hydrolytically-cleavable linking moiety.

As used herein, the phrase "hydrolytically-cleavable linking moiety or bond" describes a linking moiety or bond that can be cleaved by hydrolysis in an aqueous environment such as a physiological medium. This phrase does not encompass linking moieties or bonds that can be cleaved at a certain pH or by enzymes in a physiological medium, but rather encompasses linking moieties or bonds that can be cleaved via hydrolysis once contacting an aqueous medium such as a physiological medium, at or about the physiological pH (e.g., pH 7).

A hydrolytically-cleavable linking moiety or bond is advantageous as it allows fast release of the therapeutically active agent, once the polymeric conjugate contacts a physiological, aqueous medium. In case of conjugates comprising a high load of bone-targeting moieties as described herein, a hydrolytically-cleavable linking moiety or bond is even more advantageous since the presence of the bone targeting moiety leads to fast accumulation at the extracellular bone matrix and slows the internalization of the polymeric conjugate into the cell. Thus, a linking moiety that allows releasing the therapeutically active agent at conditions present at the extracellular bone matrix, namely, via simple hydrolysis at the matrix's pH, would lead to fast and efficient release of the therapeutically active agent at the desired bodily site.

In some embodiments, the hydrolytically-cleavable moiety comprises or consists of one or more hydrolytically-cleavable bond(s). Examples of such hydrolytically-cleavable moieties include one or more hydrolytically-cleavable bond(s) such as, but not limited to, an ester bond, an imine bond, a hydrazone bond, a ketal bond, an acetal bond and a carbonate bond.

In some embodiments, the hydrolytically-cleavable moiety comprises a hydrolytically-cleavable bond such as an ester and thus can be derived, for example, from a carboxylic acid or an alcohol, which is attached to the end of the polymeric backbone (e.g., to the terminus backbone unit).

In some embodiments, the hydrolytically-cleavable moiety is formed upon coupling the therapeutically active agent to the end of the polymeric backbone (e.g., the terminus backbone unit of the polymer) and is defined by the functional groups which are present or generated in the therapeutically active agent and at the end of the polymeric backbone (e.g., within the terminus backbone unit.

For example, when a hydrolytically-cleavable moiety comprises an ester bond, such a moiety can be formed between a hydroxyl functional group that is present or generated (e.g., by means of a spacer or by chemical modification) in the therapeutically active agent and a carboxylic group that is present or is generated (e.g., by means of a linking moiety and/or a spacer and/or chemical modification) at the end of the polymeric backbone (e.g., within the terminus backbone unit of the polymeric backbone).

Alternatively, for example, when a hydrolytically-cleavable moiety comprises an ester bond, such a moiety can be formed between a carboxylate functional group that is present or generated (e.g., by means of a spacer or chemical modification) in the therapeutically active agent and a hydroxy group that is present or is generated (e.g., by means of a linking moiety and/or a spacer and/or a chemical modification) at the end of the polymeric backbone (e.g., within the terminus backbone unit of the polymeric backbone).

Further alternatively, for example, when a hydrolytically-cleavable moiety comprises an imine bond, such a moiety can be formed between an aldehyde functional group and an amine functional group, one present or generated (e.g., by means of a spacer) in the therapeutically active agent and one present or is generated (e.g., by means of a linking moiety and/or a spacer) in the terminus backbone unit of the polymeric backbone.

Similarly, a hydrazone can be formed from amide and hydrazine.

A person skilled in the art would readily recognize how to devise a conjugate in which the therapeutically active agent is attached to the end of the polymeric backbone (e.g., to the terminus backbone unit of the polymeric backbone) via a hydrolytically-cleavable moiety, based on the functional groups that are intrinsically present at the terminus of the polymer and in the therapeutically active agent.

In one example, a carboxylate is generated on a therapeutically active agent by attaching to a free hydroxyl group on the drug to a carboxylic acid, to thereby generate a hydrolytically-cleavable ester bond. The carboxylic acid, in these embodiments, represents a hydrolytically-cleavable linking moiety, and can be attached to the terminus backbone unit via and additional ester bond and/or any other bond, via a functional group at the other end thereof. Exemplary such bifunctional carboxylic acids include, but are not limited to, dicarboxylic acids such as succinic acid, malonic acid, oxalic acid, glutaric acid, adipic acid, sebacic acid, phthalic acid, and the like. Such an esterified bifunctional carboxylic acid is an exemplary hydrolytically-cleavable linking moiety.

A pH-sensitive linker comprises a chemical moiety that is cleaved or degraded only when subjected to a certain pH condition, such as acidic pH (e.g., lower than 7), neutral pH (6.5-7) or basic pH (higher than 7).

Such a linker may, for example, be designed to undergo hydrolysis under acidic or basic conditions, and thus, the conjugate remains intact and does not release the agents attached to the polymer in the body, until its reaches a physiological environment where a pH is either acidic or basic, respectively.

Exemplary pH-sensitive linking moieties include, but are not limited to, a hydrazone bond, ester (including orthoester) bond, amide bond of cis-aconytil residue, a trityl group, acetals, ketals, Gly-ester and a -[Gly-Phe-Gly]- (SEQ ID NO:1) moiety.

In some embodiments, the biodegradable linking moiety is an enzymatically-cleavable linking moiety.

Such a linker is typically designed so as to include a chemical moiety, typically, but not exclusively, an amino acid sequence, that is recognized by a pre-selected enzyme. Such an amino acid sequence is often referred to in the art as a "recognition motif". A conjugate comprising such a linker typically remains substantially intact in the absence of the pre-selected enzyme in its environment, and hence does not cleave or degrade so as to the release the therapeutically active agent attached thereto until contacted with the enzyme.

In some embodiments, the enzymatically-cleavable linker is cleaved by an enzyme which is expressed in tumor tissues. In some embodiments, the enzymatically-cleavable linker is cleaved by an enzyme which is overexpressed in tumor tissues. A conjugate comprising such a linker ensures, for example, that a substantial amount of the conjugated therapeutically active agent is released from the conjugate only at the tumor tissue, thus reducing the side effects associated with non-selective administration of the drug and further enhancing the concentration of the drug at the tumor site.

Suitable linkers include, but are not limited to, alkyl chains; alkyl chains optionally substituted with one or more substituents and in which one or more carbon atoms are optionally interrupted by a nitrogen, oxygen and/or sulfur heteroatom.

Other suitable linkers include amino acids and/or oligopeptides.

Such alkyl chains and/or oligopeptides can optionally be functionalized so as allow their covalent binding to the moieties linked thereby (e.g., the polymeric backbone and the therapeutically active agent). Such a functionalization may include incorporation or generation of reactive groups that participate in such covalent bindings, as detailed hereinunder.

In some embodiment, the linker is a biodegradable oligopeptide which contains, for example, from 2 to 10 amino acid residues.

In some embodiments the enzymatically-cleavable linker is cleavable by pre-selected cellular enzymes, for instance, those found in osteoblasts, osteoclasts, lysosomes of cancerous cells or proliferating endothelial cells.

Non-limiting examples of such enzymes include, but are not limited to, Cathepsin K, Cathepsin D, Cathepsin H, Cathepsin L, and legumain, Cathepsin B, MMP-2 and MMP-9.

Since the conjugates described herein can be designed so as to be targeted to bone minerals, and are hence not internalized into the cells, in some embodiments, the pre-selected enzyme is such that is present in the extracellular matrix, outside the cells. Exemplary such enzymes include, but are not limited to, Cathepsin K, Cathepsin D, Cathepsin H, Cathepsin L, MMP-2 and MMP-9.

Legumain and cathepsin B are expressed mainly in the lysosome (intracellularly), yet some amount is secreted to the extracellular matrix.

In some embodiments, the linker is cleavable by Cathepsin K.

Cathepsin K is a lysosomal cysteine protease involved in bone remodeling and resorption and is predominantly expressed in osteoclasts. Its expression is stimulated by inflammatory cytokines that are released after tissue injury and in bone neoplasms [Pan et al. 2006, *J Drug Target* 14:425-435; Husmann et al. 2008, *Mol Carcinog* 47: 66-73].

A non-limiting example of a linker having Cathepsin K cleavable sites is a linker which comprises the amino acid sequence -[Gly-Gly-Pro-Nle]- (SEQ ID NO:2).

Non-limiting examples of linkers having Cathepsin D cleavable sites are those which comprise or consist of the amino acid sequences -[Gly-Thr-Gln-Phe-Phe]- (SEQ ID NO:3) and -[Gly-Ser-Thr-Phe-Phe]- (SEQ ID NO:4).

A non-limiting example of a linker having Cathepsin H cleavable sites is a linker which comprises or consists of the amino acid sequence -[Leu-Gly]- (SEQ ID NO:5).

A non-limiting example of a linker having Cathepsin L cleavable sites is a linker which comprises or consists of the amino acid sequence -[Ala-Phe-Arg-Ser-Ala-Ala-Gln]- (SEQ ID NO:6).

A non-limiting example of a linker having legumain cleavable sites is a linker which comprises or consists of the amino acid sequence -[Ala-Ala-Asn]- (SEQ ID NO:7).

Non-limiting examples of linkers having MMP-2 and MMP-9 cleavable sites are those which comprise or consist of the amino acid sequences -[His-Pro-Val-Gly-Leu-Leu-Ala-Arg]- (SEQ ID NO:8), -[Pro-Val-Ser-Leu-Ser-Tyr]- (SEQ ID NO:9), and -[Gly-Pro-Val-Gly-Leu-Ile-Gly-Lys]- (SEQ ID NO:10).

Non-limiting examples of linkers having Cathepsin B cleavable sites are those which comprise or consist of the amino acid sequences -[Arg]-, -[Cit-Val]- (SEQ ID NO:11), -[Arg-Arg]- (SEQ ID NO:12), -[Phe-Lys]- (SEQ ID NO:13), [Gly-Phe-Leu-Gly] (SEQ ID NO:14), -[Gly-Phe-Ala-Leu]- (SEQ ID NO:15), -[Ala-Leu-Ala-Leu]-(SEQ ID NO:16), -[Gly-Leu-Gly]- (SEQ ID NO:17), -[Gly-Phe-Gly]- (SEQ ID NO:18), -[Gly-Phe-Leu-Gly-Phe-Lys]-(SEQ ID NO:19) and combinations thereof.

An oligopeptide linker which contains the pre-selected amino acid sequence (recognition motif) can also be constructed such that the recognition motif is repeated several times within the linker, to thereby enhance the selective release of the attached agent. Various recognition motifs of the same or different enzymes can also be incorporated within the linker. Similarly, the linker may comprise multiple pH sensitive bonds or moieties. Linkers comprising such multiple cleavable sites can enhance the selective release of the therapeutically active agent at the desired bodily site, thereby reducing adverse side effects, and further enhance the relative concentration of the released drug at the bodily site where it exhibits its activity.

In some embodiments the therapeutically active agent is linked to the polymeric backbone and/or to the linking via a spacer, as described herein.

In some embodiments, the therapeutically active agent is attached to the first linking moiety or to the polymeric backbone via a branching unit, as defined herein and is represented by the variable "B*" in Formula I hereinafter.

In these embodiments, the load of the therapeutically active agent can be increased as the branching unit allows attaching more than one mol of the therapeutically active agent (e.g., 2 or 3 mols) per mol of the polymer.

The branching unit can be attached to the polymeric backbone either directly or via a spacer as defined herein.

The branching unit can further be attached to the polymeric backbone via a linking moiety and/or a spacer, as described herein.

The branching unit can be attached to the polymeric backbone either directly or via a spacer, and the linking moiety can be attached to the branching unit, thus linking the therapeutically active agent to the polymer via the branching unit, as described hereinbelow for the bone targeting moiety.

The therapeutically active agent that is attached to each branch of the branching unit can be the same or different.

The Bone Targeting Moiety:

As used herein throughout, the phrase "bone targeting moiety" describes a moiety that is capable of preferentially accumulating in hard tissues (i.e. bone tissues) rather than any other organ or tissue, after administration in vivo.

In some embodiments, a bone targeting moiety is characterized by a strong affinity to bone minerals (e.g, to hydroxyapettite).

In some embodiments, the bone targeting moiety is a bisphosphonate.

Bisphosphonates (BPs) such as alendronate are compounds with a chemical structure similar to that of inorganic pyrophosphate (PPi), an endogenous regulator of bone mineralization. The pharmacokinetic profile of bisphosphonates, which exhibit a strong affinity to bone mineral under physiological conditions, their low toxicity and anti-angiogenic activity (typically exhibited at relatively high concentration thereof) are advantageous for targeting to tumors confined to bony tissues.

Accordingly, in some embodiments, the bone targeting moiety described herein is a compound which comprises at least two phosphonate (—P(=O)(OH)$_2$) groups, and optionally other functional groups.

Exemplary compounds have the following general formula:

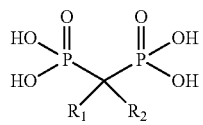

or a pharmaceutically acceptable salt thereof, as defined herein, wherein $R_1$ and $R_2$ are each independently selected from the group consisting of hydrogen, substituted or unsubstituted alkyl, substituted or unsubstituted cycloalkyl, substituted or unsubstituted aryl, substituted or unsubstituted heteroaryl, substituted or unsubstituted heteroalicyclic, halo, hydroxy, thiol, alkoxy, thioalkoxy, aryloxy, and thioaryloxy, as defined hereinbelow.

In some embodiments, at least one of $R_1$ and $R_2$ is an alkyl, cycloalkyl, aryl, heteroaryl or heteroalicyclic, optionally substituted as defined herein.

In some embodiments, the alkyl, cycloalkyl, aryl, heteroaryl or heteroalicyclic is substituted by a reactive group such as amine, hydroxy, thiol, halo, carboxylate, and the like, as defined herein, which enables its conjugation to compatible reactive groups (functional groups) of the branching unit.

In some embodiments, at least one of $R_1$ and $R_2$ is hydroxy and the other one is an alkyl, cycloalkyl, aryl, heteroaryl or heteroalicyclic, as described herein.

In some embodiments, $R_1$ is hydroxy and $R_2$ is an alkyl terminating with an amino group. The alkyl can have from 1 to 6 carbon atoms in its backbone chain.

In some embodiments, the bisphosphonate is an aminobisphosphonate, which comprises an amino group in one or both $R_1$ and $R_2$ substituents.

Exemplary bisphosphonate bone targeting moieties that are suitable for use in the context of embodiments of the invention include, but are not limited to, alendronate, cimadronate, clodronate, tiludronate, etidronate, ibandronate, neridronate, olpadronate, risedronate, piridronate, pamidronate and zoledronate.

In some embodiments the bone targeting moiety is alendronate (4-amino-1-hydroxybutylidene)bisphosphonic acid):

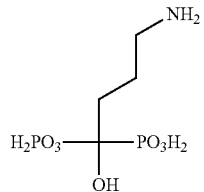

Herein, the terms "alendronate" and "bisphosphonate" encompass any pharmaceutically acceptable salts, solvates and/or hydrates thereof, as defined hereinafter.

As described herein, the molar ratio of the bone targeting moiety to the polymer is at least 2:1, and is determined by the nature of the branching unit and the number of functional groups in the branching unit to which the targeting moiety can be attached.

Highly-branched branching units, such as those arranged in a dendritic structure as described herein, allow the attachment of 3, 4 or more molecules of the targeting moiety to a single polymeric backbone, such that the mol ratio of the bone targeting moiety to the polymer is 3:1, 4:1 and even higher, namely, 6:1, 8:1, 9:1, 10:1, 16:1, and can be even higher.

Accordingly, the load of the bone targeting moiety, in terms of weight percents of the total weight of the conjugate, can be high.

In some embodiments, a load of the bone targeting moiety is at least 3 weight percent, or at least 5 weight percents or at least 7 weight percents, or at least 10 weight percents. For example, a load of alendronate as an exemplary bone targeting moiety can be 5, 6, 7, 8, 9, 10, 11 or 12 weight percent and even higher.

The high load of a bone targeting moiety can be efficiently utilized for delivering a therapeutically active agent to a bone tissue.

The bone targeting moiety can be attached to the branching unit directly, via a bond, or via a linking moiety ($L_2$ in Formula I) and/or a spacer. The linking moiety can be used to facilitate the attachment of the bone targeting moiety to the branching unit. Thus, for example, in cases where the branching unit has functional groups that are chemically incompatible with the functional groups of the bone targeting moiety, a linking moiety and/or a spacer can be attached to the branching unit or to the bone targeting moiety so as to enable attachment of the bone targeting moiety to the polymer via the branching unit.

Optionally, the branching unit is attached to the terminus backbone unit of the polymeric backbone via a linking moiety or a spacer, for the same reasons as applied herein for the branching unit.

The linkage of the bone targeting moiety to the branching unit and of the branching unit to the polymer, whether being a bond or via a linking moiety and/or a spacer, can be biocleavable or biostable (non-biocleavable).

By "biocleavable" it is meant that the bond or linking moiety can be cleaved under physiological conditions, for example, hydrolytically, enzymatically, or at a physiological pH, as is described in further detail hereinafter.

By "biostable" it is meant that the bond or linking moiety cannot be cleaved under physiological conditions.

In some embodiments, the bone targeting moiety is attached to the polymer via biostable linkages, that is, both the linkage between the bone targeting moiety and the branching unit is biostable and the linkage between the branching unit and the polymer is biostable. This may avoid release of the bone targeting moiety before it reaches its target, and thus improves the targeting of the conjugate and avoids adverse effects (e.g., cytotoxicity) which may be caused by free bone targeting moieties when present in non-diseased tissues or in tissues other than bone tissues.

Further optionally, the bone targeting moiety can be attached to the branching unit via a spacer. The spacer can be used to avoid spatial interactions and/or steric hindrance which can be imparted by attaching two or more targeting moieties to the branching units. The spacer may allow attachment of two or more bulky targeting moieties to the branching unit. Further optionally, the branching unit can be attached to the polymeric backbone via a spacer, as described herein.

The Branching Unit:

As discussed hereinabove, the bone targeting agent is attached to the polymeric backbone via a branching unit. The branching unit is utilized for generating more than one functional group (or reactive group) at the polymer's end, that can be used for attaching the bone targeting moiety to the polymer and thus is selected so as to provide a desired mol ratio of the bone targeting moiety and the polymer, which is 2:1 or more.

Herein, the phrase "branching unit" describes a chemical moiety which can be regarded as a spacer or a linking moiety for attaching one moiety to two or more other moieties via the same position of the first moiety. That is, the branching moiety is a chemical moiety that, when attached to a single position, group or atom of a substance, creates two or more functional groups that are linked to this single position, group or atom, and thus "branches" a single functionality into two or more functionalities.

In some embodiments, the branching unit is derived from a chemical moiety that has one functional group for attaching, directly or indirectly, a terminus backbone unit of the polymer, and two or more additional functionalities, each comprising a reactive group for attaching the bone targeting moiety.

Thus, in some embodiments, a branching unit is derived from a trifunctional moiety that comprises 3 or more functional groups, as described hereinabove.

It is to be noted that for any of the embodiments described herein for the conjugates, moieties, units and/or polymers, the moieties, units and/or polymers within the conjugate can be derived from the described conjugates, moieties, units and/or polymers, and that "derived from" is used to describe the moiety, unit or polymeric backbone after being conjugated to another moiety and/or unit, whereby upon conjugation, the functional moieties which were present in the polymer, unit or moiety, are already interacted with the conjugated unit, moiety or polymeric backbone.

In some embodiments, the branching unit is derived from a chemical moiety that comprises at least one trifunctional moiety. Such a trifunctional moiety comprises at least 3 functional groups, and optionally 4, 5, 6 or more functional groups, in which one functional group is utilized for attaching to the terminus backbone unit of the polymer and two or more other functional groups are utilized for attaching to the bone targeting moiety. The 3 or more functional groups can be the same or different. Exemplary such functional groups include, but are not limited to, amine, carboxylate, thiocarboxylate, hydroxy, thiol, carbamate, thiocarbamate, sulfonate, sulfinate, sulfonamide, phosphonate, phosphinate, phosphoryl, urea and thiourea. In some embodiments, each of the 3 functional groups is independently an amine, a hydroxyl, a thiol or a carboxylate, as there terms are defined herein.

Exemplary trifunctional moieties include, but are not limited to, glutamic acid, beta-glutamic acid, amino adipic acid aspartic acid, lysine, 3-hydroxy-2-amine propanol, and any other amino acid that has a carboxylate-containing side chain, or an amino-containing side-chain, or a hydroxyl-containing side chain, or a thiol-containing side-chain or a combination of two or more of the above-described functional moieties in addition to the intrinsic amine and carboxylate groups of an amino acid.

In some embodiments, any of the branching units as described herein comprises a trifunctional moiety as described herein, arranged in a dendritic structure.

By "dendritic structure" it is meant that a perfectly cascade-branched, highly defined, structure which generally comprises a core, a number of generations of ramifications (also known and referred to herein as "branches" or "branching moieties") and an external surface. The generations of ramifications are composed of repeating structural units, which radially extend outwardly from the core. The external surface of a dendritic structure of an Nth generation is, in general, composed of the terminal functional groups (also known and referred to herein as "end groups") of the Nth (final) generation. A first generation dendritic structure has one branching moiety and the number of end groups will depend on the number of ramifications of the branching moiety. A second generation dendritic structure has additional two branching moieties, and the number of end groups will depend on the number of ramifications of the branching moiety and will be raised accordingly.

Conjugates in which the branching unit is arranged in a dendritic structure can be represented by the general Formula I:

$$D-L_1-[B^*]-P-[B_1]_m^0-[B_2]_m^1-[B_3]_m^2 \ldots [Bg-L_2]_m^{g-1}-[T]_m^g \qquad \text{Formula I}$$

wherein:

D is a therapeutically active agent, as defined herein;

P is a polymer as defined herein, or a polymeric backbone derived from a polymer as defined herein;

T is a bone targeting moiety, as defined herein;

B* is a branching unit, as defined herein, through which the therapeutically active agent is attached to the polymeric backbone, or is absent;

$L_1$ is a first linking moiety, linking the therapeutically active agent to the terminus backbone unit of the polymer, and can optionally be absent, as further discussed herein;

$L_2$ is a second linking moiety, linking the bone targeting moiety to the other terminus backbone unit of said polymer, via the branching unit, or is absent;

$B_1, B_2, B_3 \ldots Bg$ are each independently a branching moiety, wherein $B_1, B_2, B_3 \ldots Bg$ together form a branching unit having a dendritic structure, as described herein;

m is an integer that equals 2, 3, 4, 5 or 6, representing the ramification number of the dendritic structure, and is preferably, 2, 3 or 4; and g is an integer that ranges from 1 to 20, representing the number of generations of the dendritic structure, and preferably ranges from 1 to 10, or from 1 to 6, or is 1, 2, 3 or 4.

In some embodiments, g is 2.

The dendritic structure is thus composed of a cascade of branching moieties, wherein the number of branching moieties in each generation equals $m^{g-1}$. Thus, for example, when g=1, the number of branching moieties is one ($m^0$), and the number of the bone targeting moieties attached to the polymer via the branching unit equals to the ramification number of branching moiety. When g=1, the branching unit consists of a single branching moiety. When m=2, there are 2 branching units attached to the polymeric backbone.

When g=2, the number of branching moieties is the second generation is ($m^1$), and the number of the bone targeting moieties attached to the polymer via the branching unit is a (mathematic) power of the ramification number of branching moiety. When g=2, the branching unit consists of $m^1+1$ branching moieties. When m=2, there are 4 branching units attached to the polymeric backbone.

The branching moieties composing the branching unit in a dendritic structure can be any of the moieties described herein as suitable for a branching unit. Two or more types of branching moieties can be used within a branching unit, although preferably, the same branching moieties compose the dendritic branching unit.

The Spacer:

The term "spacer" as used herein describes a chemical moiety that is covalently attached to, and interposed between, the polymeric backbone and the branching unit, the branching unit and the bone targeting moiety, the branching unit and a linking moiety or the polymeric backbone and a linking moiety, thereby forming a bridge-like structure between the spaced moieties.

The term "spacer" as used herein also describes such a chemical moiety that is covalently attached to, and interposed between, the polymeric backbone and the therapeutically active agent, the polymeric backbone and the linking moiety through which the therapeutically active agent is attached to the polymer, the linking moiety and the therapeutically active agent, or any of these moieties and a branching unit, if present at the end of the polymer where the therapeutically active agent is attached, thereby forming a bridge-like structure between the spaced moieties.

Suitable spacers include, but are not limited to, alkylene chains, optionally substituted by one or more substituents and which are optionally interrupted by one or more nitrogen, oxygen and/or sulfur heteroatom.

Other suitable spacers include amino acids and amino acid sequences, optionally functionalized with one or more reactive groups for being coupled to the polymeric backbone/bone targeting moiety/branching unit/linking moiety/therapeutically active agent.

In some embodiments, the spacer has the formula G-$(CH_2)$n-K, wherein n is an integer from 1 to 10; and G and K are each a reactive group such as, for example, NH, O, carboxylate, amide, carbonyl, S and the like.

In some embodiments, the spacer is an amino acid sequence, optionally an inert amino acid sequence (namely, does not affect the affinity or selectivity of the conjugate).

In some cases, a spacer is utilized for enabling a more efficient and simpler attachment of spaced moieties, in terms of steric considerations (renders the site of attachment less hindered) or chemical reactivity considerations (adds a compatible reactive group to the site of attachment). In some cases, the spacer may contribute to the performance of the resulting conjugate. For example, the spacer may render an enzymatically-cleavable linking moiety less sterically hindered and hence more susceptible to enzymatic interactions.

In some embodiments, the spacer is a degradable spacer, which is capable of undergoing degradation reactions so as to release the agent attached thereto. In some embodiments, the spacer is biodegradable, as defined herein.

The spacer can be, for example, a substituted or unsubstituted cycloalkyl group, a substituted or unsubstituted heteroalicyclic group, a substituted or unsubstituted aryl group and a substituted or unsubstituted heteroaryl group; wherein the substituents can be, for example, hydroxy, alkoxy, thiohydroxy, thioalkoxy, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and $NR_aR_b$ wherein $R_a$ and $R_b$ are each independently hydrogen, alkyl, cycloalkyl, aryl, carbonyl, sulfonyl, trihalomethylsulfonyl and, when combined, a five- or six-member heteroalicyclic ring, whereby the spacer may be linked to the therapeutically active agent/bone targeting moiety/linker/polymer either directly, through the cyclic group or alternatively, via one or more of the substituents.

In some embodiments, the spacer facilitates the attachment of the therapeutically active agent or the linking moiety to the polymeric backbone, or the attachment of the bone targeting moiety to the branching unit or of the branching unit to the polymeric backbone. This may be effected by imparting a reactive group to one or both moieties to be coupled to one another and/or by modifying the solubility of one of the moieties, so as to facilitate its reaction with another moiety.

For example, in some cases the polymer is a water-soluble polymer while the therapeutically active agent is hydrophobic, and hence has a limited solubility in aqueous solutions or in polar organic solvents. In such cases, a spacer can be attached to the therapeutically active agent so as to enhance the water solubility thereof and to facilitate the conjugation thereof to the polymer in an aqueous solution or a protic or polar organic solvent.

A spacer may also be used in order to attach other agents (e.g., a labeling agent, as described hereinbelow) to the conjugate.

The spacer may be varied in length and in composition, depending on steric consideration and may be used to space the therapeutically active agent and/or bone targeting moiety form the polymeric backbone.

Any of the above-described spacers and linking moieties can be utilized for any of the branching units described herein, having a dendritic structure or not.

Exemplary Polymeric Conjugates:

In some embodiments, the polymeric conjugate can be in a form of micelles, formed sue to the hydrophilic nature of bone targeting moieties (such as alendronate), an amphiphillic polymer and a hydrophobic nature which is common for anti-cancer and/or anti-angiogenesis agents, as discussed in further detail in the Examples section that follows.

As discussed hereinabove, the present inventors have conjugated alendronate to a PEG polymeric backbone together with Paclitaxel and the bone targeting capacity of the obtained polymeric conjugate was demonstrated by the enhanced binding of the conjugate to hydroxyapatite (as a modal mimicking bone tissue). The beneficial therapeutic activity of the conjugate in the treatment of a mouse model of bone cancer metastasis was also demonstrated.

According to some embodiments, the conjugate comprises any of the polymers described herein (or polymeric backbones derived therefrom), the bone targeting moiety is alendronate, and the therapeutically active agent is paclitaxel.

According to some embodiments, the conjugate comprises a polymeric backbones derived from poly(ethylene glycol), the bone targeting moiety is alendronate, and the therapeutically active agent is paclitaxel.

In some of these embodiments, the branching unit has a dendritic structure as defined herein and, in some of these embodiments, the branching unit comprises at least 3 beta-glutamic acid moieties arranged in a dendritic structure, as described herein.

In some of these embodiments, the paclitaxel is attached to the terminus backbone unit via a hydrolytically-cleavable linking moiety such as an ester-containing moiety (a carboxylate).

In some of these embodiments, the ester-containing moiety is derived from a bifunctional carboxylic acid such as succinic acid.

In some embodiments, the chemical structure has the structure:

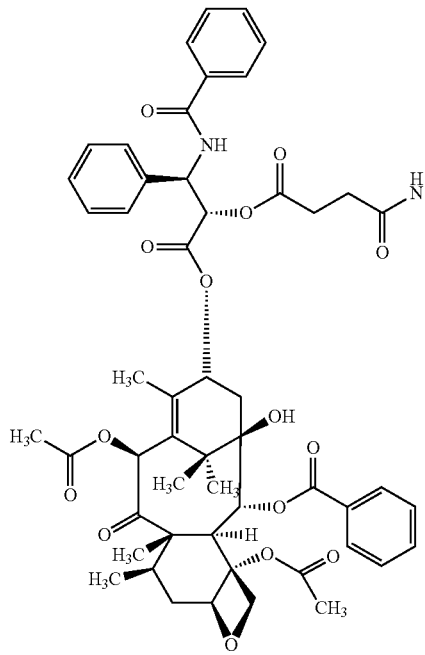
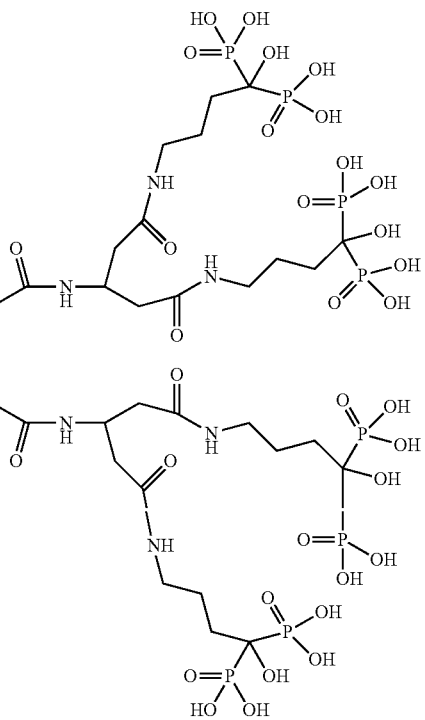

wherein n is an integer that ranges from 10 to 1000.

The chemical structure of an exemplary such conjugate is depicted in FIG. 1 (as Compound 3).

Labeled Conjugates:

Any of the conjugates as described herein may further comprise a labeling agent attached thereto. The labeling agent can be attached to any one of the linking moieties, spacers, branching moieties or units, as described herein.

In some embodiments, the labeling agent is attached to a spacer, as described herein, and the spacer bridges between two of the therapeutically active agent, the first linking moiety and terminus backbone unit the polymer.

In some embodiments, the labeling agent is attached to a spacer, as described herein, and the spacer bridges between two of the bone targeting moiety, the branching unit and terminus backbone unit the polymer.

The attachment of a labeling agent to the conjugate, enables utilizing these conjugates for monitoring bone related disease or disorders, for example, monitoring the therapeutic effect exhibited by the conjugate described herein.

As used herein, the phrase "labeling agent" describes a detectable moiety or a probe. Exemplary labeling agents which are suitable for use in the context of these embodiments include, but are not limited to, a fluorescent agent, a radioactive agent, a magnetic agent, a chromophore, a bioluminescent agent, a chemiluminescent agent, a phosphorescent agent and a heavy metal cluster.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}Tc$, $^{18}F$, $^{131}I$ and $^{125}I$.

The term "magnetic agent" describes a substance which is attracted to an externally applied magnetic field. These substances are commonly used as contrast media in order to improve the visibility of internal body structures in Magnetic resonance imaging (MRI). The most commonly used compounds for contrast enhancement are gadolinium-based. MRI contrast agents alter the relaxation times of tissues and body cavities where they are present, which depending on the image weighting can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process.

The term "chemiluminescent agent" describes a substance which emits light as the result of a chemical reaction.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

In some embodiments, the labeling agent is a fluorescent agent such as FITC. An exemplary FITC labeled-conjugate as described herein is depicted in FIG. 1 (FITC labeled-Compound 3).

As discussed hereinabove, the tumor vasculature possesses an enhanced capacity for the uptake of macromolecules and colloidal drug carriers having a high molecular weight and large hydrodynamic diameter due to the EPR effect. Therefore, a conjugate as described herein, having a large enough hydrodynamic diameter is beneficial. The term "large enough" is used herein to describe a conjugate having a hydrodynamic diameter which leads to an increase in the ratio of conjugate accumulated in the tumor tissue as compared to other tissues. The determination of the optimal ratio is well within the capability of those skilled in the art. For example, the ratio may be 1.1, 2, 3, 4, 5 etc. In some embodiments, the hydrodynamic diameter is in the range of from 15 nm to 300 nm. In some embodiments, the hydrodynamic diameter is in the range of from 50 nm to 250 nm. In some embodiments the hydrodynamic diameter is in the range of from 100 nm to 250 nm. In yet another embodiment the hydrodynamic diameter is in the range of 150 nm to 200 nm. The hydrodynamic diameter can be measured as described below under the Materials and Methods of the Example section which follows hereinbelow.

Chemical Forms of the Conjugates:

The conjugates described hereinabove may be administered or otherwise utilized either as is, or as a pharmaceutically acceptable salt, solvate, hydrate or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

The phrase "pharmaceutically acceptable salts" is meant to encompass salts of the moieties and/or conjugates which are prepared with relatively nontoxic acids or bases, depending on the particular substituents found on the compounds described herein. When conjugates of the present invention contain relatively acidic functionalities, base addition salts can be obtained by contacting the neutral (i.e., non-ionized) form of such conjugates with a sufficient amount of the desired base, either neat or in a suitable inert solvent. Examples of pharmaceutically acceptable base addition salts include sodium, potassium, calcium, ammonium, organic amino, or magnesium salt, or a similar salt. When conjugates of the present invention contain relatively basic functionalities, acid addition salts can be obtained by contacting the neutral form of such conjugates with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific conjugates of the present invention contain both basic and acidic functionalities that allow the conjugates to be converted into either base or acid addition salts.

The neutral forms of the conjugates are preferably regenerated by contacting the salt with a base or acid and isolating the parent conjugate in a conventional manner. The parent form of the conjugate differs from the various salt forms in certain physical properties, such as solubility in polar solvents, but otherwise the salts are equivalent to the parent form of the conjugate for the purposes of the present invention.

In an example, a pharmaceutically acceptable salt of alendronate is utilized. An exemplary such salt is sodium alendronate. An alendronate-containing conjugate can therefore comprise a sodium salt of alendronate.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

The conjugates described herein may possess asymmetric carbon atoms (optical centers) or double bonds; the racemates, enantiomers, diastereomers, geometric isomers and individual isomers are encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The conjugates described herein can exist in unsolvated forms as well as solvated forms, including hydrated forms. In general, the solvated forms are equivalent to unsolvated forms and are encompassed within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Certain conjugates of the present invention may exist in multiple crystalline or amorphous forms. In general, all physical forms are equivalent for the uses contemplated by the present invention and are intended to be within the scope of the present invention.

Uses:

As discussed hereinabove, the conjugates described herein comprise a bone targeting moiety which enables the targeting of the conjugate to bone and bone related (osteoid) structures. Due to the therapeutic activity of the conjugates, they can be efficiently used for treating bone related disease and disorders.

Hence, according to another aspect of some embodiments of the present invention there are provided methods of treating a bone related disease or disorder in a subject in need thereof. These methods are effected by administering to the subject a therapeutically effective amount of any of the conjugates described herein.

Accordingly, according to another aspect of some embodiments of the present invention there are provided uses of any of the conjugates described herein as a medicament. In some embodiments, the medicament is for treating a bone-related disease or disorder.

According to another aspect of some embodiments of the present invention, the conjugates described herein are identified for use in the treatment of a bone related disease or disorder.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The phrase a "bone related disease or disorder" describes a disease or disorder wherein bone formation, deposition, or resorption is abnormal, especially those characterized by excessive angiogenesis. The phrase "bone related disease or disorder" encompasses disease and disorders occurring in bodily sites other than bone which evolved from a bone related disease or disorder such as, for example, metastasis of bone cancer in another organ. Bone-related diseases and disorders include, but are not limited to, bone cancer and bone cancer metastases, osteopenia due to bone metastases, periodontal disease, periarticular erosions in rheumatoid arthritis, Paget's disease, malignant hypercalcemia, osteolytic lesions produced by bone metastasis, bone abnormalities caused by cancer therapeutics and hyperostosis.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. When the treatable disease is bone cancer, the term would encompass any inhibition of tumor growth or metastasis, or any attempt to inhibit, slow or abrogate tumor growth or metastasis.

It is noted herein that by targeting a therapeutically active agent via the methodologies described herein, the toxicity of the therapeutically active agent is substantially reduced, due to the conjugate selectivity towards bone tissues. Consequently, besides the use of the conjugates described herein in a clinically evident disease, optionally in combination with other drugs, these conjugates may potentially be used as a long term-prophylactic for individuals who are at risk for relapse due to residual dormant cancers.

The term "subject" (alternatively referred to herein as "patient") as used herein refers to an animal, preferably a mammal, most preferably a human, who has been the object of treatment, observation or experiment.

As demonstrated in the Examples section that follows, an exemplary conjugate, according to some embodiments described herein, inhibited angiogenesis as well as cell proliferation and therefore can be utilized for the treatment of bone related disease and disorders characterized by pathologically excessive angiogenesis wherein the inhibition of angiogenesis and/or cell proliferation is beneficial.

Hence, in some embodiments the bone related disease or disorder is associated with angiogenesis.

Tumor growth and metastasis are particularly dependent on the degree of angiogenesis. Tumor angiogenesis is the proliferation of a network of blood vessels that penetrate into cancerous tumors in order to supply nutrients and oxygen and remove waste products, thus leading to tumor growth. Tumor angiogenesis involves hormonal stimulation and activation of oncogenes, expression of angiogenic growth factors, extravasation of plasma protein, deposition of a provisional extracellular matrix (ECM), degradation of ECM, and migration, proliferation and elongation of endothelial capillaries. Inhibition of further vascular expansion has therefore been the focus of active research for cancer therapy.

Hence, in some embodiments the bone related disease or disorder is selected from the group consisting of bone cancer metastases and bone cancer.

The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor which is not self-limited in its growth, is capable of invading into adjacent tissues, and may be capable of spreading to distant tissues (metastasizing). The term "benign tumor" describes a tumor which is not malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

The term "bone cancer" describes tumors that arise from the tissues of the bone. The term "bone cancer", as used herein, further encompasses tumors in tissues located in proximity to bone structures and associated with bone such as cartilage, bone cavity and bone marrow. The term "Bone cancer" further encompasses cancer which evolved from bone cells (i.e. primary tumor) as well as cancer cells which have "breaken away", "leaked", or "spilled" from a primary tumor located in bone, entered the lymphatic and/or blood vessels, circulated through the lymphatic system and/or bloodstream, settled down and proliferated within normal tissues elsewhere in the body thereby creating a secondary tumor. For example, metastases originating from osteosarcoma can be frequently found in the lungs and in other organs. These lesions produce an osteoid and therefore can be targeted similarly with compounds with high affinity to bone mineral, hydroxyapatite, such as alendronate, and other bisphosphonates as well as oligoaspartates.

Bone cancer is found most often in the bones of the arms and legs, but it can occur in any bone.

Bone cancers are also known as sarcomas. There are several types of sarcomas of bone, depending upon the kind of bone tissue where the tumor developed. Exemplary types of bone cancers that are treatable according to embodiments of the invention include, but are not limited to, osteosarcoma, Ewing's sarcoma, chondrosarcoma, fibrosarcoma, malignant giant cell tumor, and chordoma.

Osteosarcoma is the most common type of primary bone cancer and classified as a malignant mesenchymal neoplasm in which the tumor directly produces defective osteoid (immature bone). It is a highly vascular and extremely destructive malignancy that most commonly arises in the metaphyseal ends of long bones. Several strategies were proposed, such as immune-based therapy, tumor-suppressor or suicide gene therapy, or anticancer drugs that are not commonly used in osteosarcoma [Quan et al. *Cancer Metastasis Rev* 2006; 10: 707-713]. However, still one-third of patients die from this devastating cancer, and for those with unresectable disease there are no curative systemic therapies.

The term "bone metastases" describes cancer evolving form a primary tumor located in bodily site other than bone but metastasizing to the bone (i.e. a secondary tumor). Cancers that commonly metastasize, or spread, to the bones include breast cancer, lung cancer, thyroid cancer, prostate cancer, some brain cancers and cancers of the kidney.

For example, prostate cancer is the most common cancer of males in industrialized countries and the second leading cause of male cancer mortality. Prostate cancer predominantly metastasizes to bone, but other organ sites are affected including the lung, liver, and adrenal gland. Bone metastases incidence in patients with advanced metastatic disease is approximately 70%. Bone metastases are associated with considerable skeletal morbidity, including severe bone pain, pathologic fracture, spinal cord or nerve root compressions, and hypercalcemia of malignancy.

As discussed hereinabove, the conjugates described herein may be further utilized for monitoring bone related disease or disorders. In such a case the conjugate further comprises a labeling agent, as defined herein for easy detection of the conjugate in the body of the patient, using well known imaging techniques. For example, in the case of the bone related disease or disorder being bone cancer the detection of the conjugate, as assessed by the level of labeling agent signal, can serve to detect bone cancer metastases in bodily sites other than bone.

Hence, according to another aspect of some embodiments of the present invention there are provided methods of monitoring a bone related disease or disorder in a subject. The method according to these embodiments of the invention is effected by administering to the subject any of the conjugates described herein, having a labeling agent attached to the polymer, as described herein, and employing an imaging technique for monitoring a distribution of the conjugate within the body or a portion thereof.

Accordingly, according to another aspect of some embodiments of the present invention there are provided uses of any of the conjugates described herein, having a labeling agent as described herein, as diagnostic agents and/or in the manufacture of a diagnostic agent for monitoring a bone related disease or disorder.

According to another aspect of some embodiments of the present invention, each of the conjugates described herein, which comprises a labeling agent, is identified for use as a diagnostic agent, for monitoring a bone related disease or disorder.

Suitable imaging techniques include but are not limited to positron emission tomography (PET), gamma-scintigraphy, magnetic resonance imaging (MRI), functional magnetic resonance imaging (FMRI), magnetoencephalography (MEG), single photon emission computerized tomography (SPECT) computed axial tomography (CAT) scans, ultrasound, fluoroscopy and conventional X-ray imaging. The choice of an appropriate imaging technique depends on the nature of the labeling agent, and is within the skill in the art. For example, if the labeling agent comprises Gd ions, then the appropriate imaging technique is MRI; if the labeling agent comprises radionuclides, an appropriate imaging technique is gamma-scintigraphy; if the labeling agent comprises an ultrasound agent, ultrasound is the appropriate imaging technique, etc.

According to another aspect of the present invention there is provided a pharmaceutical composition comprising, as an active ingredient, any of the conjugates described herein and a pharmaceutically acceptable carrier.

Accordingly, in any of the methods and uses described herein, any of the conjugates described herein can be provided to an individual either per se, or as part of a pharmaceutical composition where it is mixed with a pharmaceutically acceptable carrier.

As used herein a "pharmaceutical composition" refers to a preparation of one or more of the conjugates described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p.1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described hereinabove is packaged in a packaging material and identified in print, in or on the packaging material, for use in the treatment of a bone related disease or disorder, as described herein.

According to another embodiment of the present invention, the pharmaceutical composition is packaged in a packaging material and identified in print, in or on the packaging material, for use in monitoring a bone related disease or disorder, as described herein.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In any of the methods, uses and compositions described herein, the conjugates described herein can be utilized in combination with additional therapeutically active agents. Such additional agents include, as non-limiting examples, chemotherapeutic agents, anti-angiogensis agents, hormones, growth factors, antibiotics, anti-microbial agents, anti-depressants, immunostimulants, and any other agent that may enhance the therapeutic effect of the conjugate and/or the well-being of the treated subject.

Syntheses and Intermediates:

In the course of devising a synthetic pathway for preparing the conjugates as described herein, the present inventors have successfully prepared representative intermediate structures that are useful for preparing the conjugates as described herein and/or for evaluating the biological activity of the conjugates as described herein.

According to an aspect of some embodiments of the present invention there is provided a conjugate comprising a polymeric backbone having attached to an end thereof (e.g., to a terminus backbone unit thereof) a bisphosphonate moiety, said bisphosphonate being attached to said terminus backbone via a branching unit, wherein a mol ratio of said bisphosphonate to said polymer is at least 2:1.

Embodiments as described herein for the polymer, the branching unit and the bone targeting moiety in the context of bisphosphonates are all contemplated in the herein described embodiments of this aspect.

In some embodiments, the branching unit has a dendrite structure.

In some embodiments, such a conjugate can be represented by Formula II as follows:

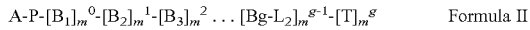

Formula II wherein:

P is said polymeric backbone;

T* is a bisphosphonate bone targeting moiety as described herein;

A is an end group of the polymeric backbone, and can be a functional group intrinsic to the polymer, per se, or protected, or any other functional group generated at the end of the polymer, as described hereinabove;

$L_2$ is a linking moiety, linking said targeting moiety to one end of the polymeric backbone (e.g., to a terminus backbone unit of the polymer) via the branching unit, as described herein, or is absent;

$B_1$, $B_2$, $B_3$ . . . Bg are each independently a branching moiety, wherein $B_1$, $B_2$, $B_3$ . . . Bg together form a branching unit having a dendritic structure, as described herein;

m is an integer that equals 2, 3, 4, 5 or 6, representing the ramification number of said dendritic structure; and g is an integer that ranges from 1 to 20, representing the number of generations of said dendritic structure.

In some embodiments, the polymer is a poly(alkylene glycol).

In some embodiments, the bisphosphonate is alendronate.

In some embodiments, the polymer is a poly(alkylene glycol), and the bisphosphonate is alendronate.

According to an aspect of some embodiments of the present invention there is provided a conjugate comprising a polymeric backbone having attached thereto a therapeutically active agent, the therapeutically active agent being attached to one end of the polymeric backbone (e.g., to a terminus backbone unit at one end of the polymer) wherein the polymer further comprises a reactive group attached to a another end of the polymeric backbone 9 e.g., to terminus backbone unit at another end of the polymer) via a branching unit, as described herein, wherein a mol ratio of said functional group to said polymer and is at least 2:1.

In some embodiments, the reactive group is useful for attaching a targeting moiety, e.g., a bone targeting moiety, to the conjugate.

Embodiments as described herein for the polymer, the branching unit, the linking moiety and the therapeutically active agent are all contemplated in the herein described embodiments of this aspect.

In some embodiments, the branching unit has a dendrite structure.

In some embodiments, such a conjugate can be represented by Formula III as follows:

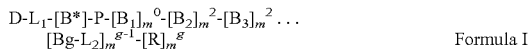

Formula I wherein:

D is a therapeutically active agent as described herein;

P is a polymeric backbone as described herein;

R is a reactive group;

B* is a branching unit or is absent;

$L_1$ is a linking moiety, linking the therapeutically active agent to the end of the polymeric backbone, as described herein;

$L_2$ is a second linking moiety, linking the reactive group to the other end of the polymeric backbone, via the branching unit, or is absent;

$B_1$, $B_2$, $B_3$ . . . Bg are each independently a branching moiety, wherein $B_1$, $B_2$, $B_3$ . . . Bg together form a branching moiety having a dendritic structure, as described herein;

m is an integer that equals 2, 3, 4, 5 or 6, representing the ramification number of the dendritic structure; and g is an integer that ranges from 1 to 20, representing the number of generations of the dendritic structure.

In some embodiments, the first linking moiety is a hydrolytically-cleavable moiety as described herein.

In some embodiments, the polymeric backbone is derived from a ply(alkylene glycol), as described herein, and in some embodiments, it is derived from PEG.

The reaction group can be, for example, hydroxy, amine, carboxylate, halide, sulfate, sulfonate, and the like.

In some embodiments, the reactive group is carboxylate.

According to an aspect of the some embodiments of the present invention there is provided a process of preparing a polymeric conjugate as described herein.

In some embodiments, the process is effected by reacting a conjugate comprising a polymeric backbone having a bone targeting moiety attached to one end thereof via a branching moiety, with a therapeutically active agent.

In some embodiments, the conjugate and the therapeutically active agent are selected so as to generate a hydrolytically-cleavable linking moiety, as described herein. In some of these embodiments, the process further comprises, prior to the reacting, attaching such a linking moiety to the therapeutically active agent, whereby the reacting in performed by forming a bond between the conjugate and the linking moiety.

Conditions, optional protecting groups, optional activating groups and the like, can be selected by one of skill in the art so as to efficiently perform the reaction while considering the chemical structures of the reactants.

In some embodiments, the reacting conjugate has general Formula III, as described herein.

Providing such a conjugate can be performed by sequentially and controllably growing at one end of a polymeric backbone (e.g., protected at the other end thereof) a dendritic branching unit, by sequential attachment of the branching moieties, as described herein.

An exemplary process as described herein is described in the Examples section that follows, and in FIG. 2.

In some embodiments, a process of preparing the polymeric conjugates as described herein is effected by reacting a conjugate of a polymeric backbone and a therapeutically active agent as described herein, which terminates by two or more reactive groups, with a bone targeting moiety or moieties.

General:

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be unsubstituted or substituted, as long as the substituent does not interfere with the performance and/or intended use of the compound. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be unsubstituted or substituted, as long as the substituent does not interfere with the performance and/or intended use of the compound. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be unsubstituted or substituted, as long as the substituent does not interfere with the performance and/or intended use of the compound. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, indole, indolenine, quinoline, isoquinoline and purine. The heteroaryl group may be unsubstituted or substituted, as long as the substituent does not interfere with the performance and/or intended use of the compound. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be unsubstituted or substituted, as long as the substituent does not interfere with the performance and/or intended use of the compound. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is defined as hereinabove.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

An "oxo" group refers to a =O group.

A "carboxylate" or "carboxyl" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

An "ester" refers to a C-carboxy group wherein R' is not hydrogen.

An ester bond refers to a —O—C(=O)— bond.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

A carbamate bond describes a —O—C(=O)—NR'— bond, where R' is as described herein.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'— bond, where R' is as described herein.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

An amide bond describes a —NR'—C(=O)— bond, where R' is as defined herein.

A "urea" group refers to an —N(R')—C(=O)—NR"R'" group, where each of R' and R" is as defined herein, and R'" is defined as R' and R" are defined herein.

A "nitro" group refers to an —$NO_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

A "phosphoric acid" is a phosphate group is which each of R is hydrogen.

The term "phosphinyl" describes a —PR'R" group, with each of R' and R" as defined hereinabove.

The term "thiourea" describes a —N(R')—C(=S)—NR"— group, with each of R' and R" as defined hereinabove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples which, together with the above descriptions, illustrate the invention in a non limiting fashion.

Example 1

Chemical Syntheses and Characterization

Materials and Experimental Methods

Materials:

All reactions requiring anhydrous conditions were performed under an Ar or $N_2$ atmosphere. Chemicals and solvents were either A.R. grade or purified by standard techniques.

Paclitaxel (PTX) was obtained from Indena (Milan, IT) or from Alcon Biosciences Ltd. (Mumbai, India; Petrus Chemicals and Materials Ltd., Israel).

Alendronate (ALN) was purchased from Alcon Biosciences Ltd. (Mumbai, India; Petrus Chemicals and Materials Ltd., Israel).

Boc-NH-PEG5 kDa-NHS and Lys(cFmoc)-OH was obtained from Iris Biotech GmbH (Marktredwitz, Germany).

N-Hydroxysuccinimide (NHS), N,N-Dicyclohexylcarbodiimmide (DCC), succinic anhydride, β-glutamic acid (β-Glu), silica gel ($SiO_2$), sodium sulfate anhydrous ($Na_2SO_4$), triethylamine (TEA), trifluoroacetic acid (TFA), 2,4,6-trinitrobenzenesulfonic acid (TNBS), dimethylsulfoxide-$d_6$ and $D_2O$ were purchased from Sigma-Aldrich.

Glycil-glycine (Gly-Gly) was obtained from Merck (Darmstadt, Germany).

All other chemical reagents, including salts and solvents were purchased from Sigma-Aldrich.

Instrumental Data:

Thin layer chromatography (TLC) was performed using silica gel plates Merck 60 $F_{254}$; compounds were visualized by irradiation with UV light and/or by treatment with a solution of phosphomolybdic acid (20% wt. in ethanol), followed by heating.

$^1$H NMR measurements were performed using Bruker AMX 200 or 400 instrument. The chemical shifts are expressed in δ relative to TMS (δ=0 ppm) and the coupling constants J in Hz. The spectra were recorded in $CDCl_3$, as a solvent at room temperature, unless otherwise indicated.

Determination of Free and Total PTX Contents in the Conjugates:

The amount of PTX in the conjugates was evaluated by reverse phase HPLC using an Agilent 300-Extend C18 (4.6× 250 mm; 5 μm) column, with the UV detector settled at 227 nm. The eluents A and B were $H_2O$ and $CH_3OH$, respectively. The elution was performed by the following gradient: from 5% B to 50% B in 5 minutes, from 50% B to 80% B in 14 minutes, from 80% B to 100% B in 5 minutes, and from 100% B to 5% B in 5 minutes, at a flow rate of 1 mL/minute.

The total drug content was evaluated by RP-HPLC following the release of PTX from the conjugates. 3 mg of conjugate were dissolved in 1 mL of MeOH. Following the addition of 2% (v/v) of NaOH 0.2 N, the solution was incubated at 50° C. for 2 hours. The drug was then extracted by ethyl acetate. The organic phase was evaporated and the residue was solubilized in methanol. The elution was performed as reported above. The amount of PTX was calculated using PTX calibration curve obtained using the same method. The standard error for this analysis, calculated using solutions of PTX at known concentrations, is ±1.89%.

Determination of ALN Content Bound to PEG:

The formation of chromophoric complex between ALN and $Fe^{3+}$ ions in perchloric acid solution was used to determine the ALN content by spectrophotometry [as described in Kuljanin et al. *J. Pharm. Biomed. Anal.* 2002, 28, 1215-1220]. Briefly, conjugates (2.5, 5 and 10 mg) were dissolved in a mixture of 0.1 mL of 4 mM $FeCl_3$ and 0.8 mL of 0.2 M perchloric acid ($HClO_4$). The content of ALN in the conjugates was determined against a calibration graph of serial dilutions of 0-3 mM ALN. Sample absorbance was measured spectrophotometrically at λ=300 nm.

Dynamic Light Scattering (DLS) of Conjugates:

The mean hydrodynamic diameter of the conjugates was evaluated using a real time particle analyzer (NanoSight LM20™). PTX-PEG and PTX-PEG-ALN (5 mg/mL) were injected into the chamber, allowed to equilibrate for 30 seconds and analyzed by a Nanoparticle Tracking Analysis (NTA) software.

Conjugates' Stability in Buffer Solution at Different pH Values and in Plasma:

Each conjugate (3 mg/mL) was incubated at 37° C. for 48 hours in PBS at pH 5 and 7.4 to evaluate the drug release. Samples of 50 μL were withdrawn at predetermined times and analyzed by RP-HPLC using the conditions reported above, evaluating the decrease of the conjugate peak in the chromatographic profile.

The tested conjugates were also incubated at 37° C. for 48 hours in mouse plasma, obtained after centrifugation of blood sample at 2000×g for 10 minutes. Samples of 60 μL were withdrawn at predetermined times and 60 μL of CH$_3$CN were added to achieve plasma protein precipitation. Samples were centrifuged at 15000×g and the supernatant was withdrawn and analyzed by RP-HPLC using the conditions reported above.

The stability of the conjugates was also evaluated by dynamic light scattering. Solution of each conjugate (7 mg/mL) in PBS pH 5 and 7.4 were prepared and immediately extruded with manual extruder (Liposofast Avestin) at 200 nm and analyzed using a light scattering instrument (Malvern Nano-S, Worcestershire, United Kingdom). The instrument was settled at 37° C., the detector position was at 173° and the analysis was performed every 20 minutes (the first measurement was performed after 5 minutes of equilibration) for 4 hours and, after storage in similar conditions, the sample was analyzed at 24 hours.

Chemical Syntheses

Synthesis of PEG-ALN, PEG-PTX and PTX-PEG-ALN Conjugates

The chemical structures of PEG-ALN (Compound 1) PEG-PTX (Compound 2) and PTX-PEG-ALN (Compound 3), exemplary conjugates according to some embodiments of the present invention, are depicted in FIGS. 1A, 1B and 1C, respectively, wherein X is —C(=O)—.

An exemplary synthetic pathway for preparing PTX-PEG-ALN (Compound 3) is depicted in FIG. 2.

The synthesis of PTX-PEG (Compound 2) was performed in three main steps: synthesis of SPTX, synthesis of PEG-dendrimer and binding of SPTX to PEG-dendrimer (see, FIG. 2).

The PEG-dendrimer was built at carboxylic activated terminus of commercial Boc-NH-PEG-NHS using β-Glutamic acid (βGlu) as symmetric bicarboxylic branching unit.

PEG-ALN was obtained by firstly linking the ALN targeting residues to the PEG dendrimer carboxylic group and then by removing the Boc protecting group.

The coupling of SPTX to PEG-ALN yielded PTX-PEG-ALN.

Preparation of 2'-succinyl-paclitaxel (SPTX)

To 1 gram (1.17 mmol) of paclitaxel, dissolved in 30 mL of anhydrous pyridine, 585 mg (5.85 mmol) of succinic anhydride were added. The reaction was stirred at room temperature for 48 hours. The SPTX was purified by chromatography on a SiO$_2$ column (30×2.5 cm) eluted with a chloroform-methanol mixture (97:3 to 90:10) and determined by TLC (Rf 0.5 in chloroform-methanol 90:10).

SPTX was characterized by $^1$H-NMR spectroscopy, showing the characteristic signals of PTX together with those of the succinic spacer, as follows.

$^1$H-NMR of SPTX (CDCl$_3$): δ=1.15 (s, 3H, C16), 1.24 (s, 3H, C17), 1.68 (s, 3H, C18), 1.79 (s, 3H, C19), 2.24 (s, 3H, C31), 2.38 (s, 3H, C29), 2.5-2.7 (m, 4H, —CH2-CH2- succinic spacer), 4.9 (d, 1H, C5), 5.66 (d, 1H, C2'), 6.27 (s, 1H, C10), 7.25 (s, 3'-Ph), 7.4 (m, 3'-NBz), 7.5 (m 2-OBz), 7.75 (d, 3'NBz), 8.1 (d, 2-OBz) ppm.

Preparation of Boc-NH-PEG-flGlu-(COOH)$_2$ (Compound 4)

Boc-NH-PEG-NHS (MW 4928 Da; 3.5 grams; 0.71 mmol) was added to β-glutamic acid (βGlu; 313 mg; 2.13 mmol), dissolved in 150 mL of 0.1 M borate buffer/CH$_3$CN (3:2) mixture having pH 8.0. The reaction mixture was let to proceed for 5 hours under stirring. The reaction mixture pH was thereafter adjusted to about 4.5 with 0.2N HCl and the excess of βGlu was removed by extractions with CHCl$_3$ (6×300 mL). The organic phase was dried over anhydrous Na$_2$SO$_4$, concentrated under vacuum and dropped into 1 L of cold diethyl ether under stirring. After 1 hour at −20° C., the precipitate was filtered and dried under vacuum, to thereby afford Compound 4 (3.345 grams, 95% yield). The absence of free βGlu in the conjugate was verified by TNBS test according to Snyder and Sabocinsky assay [*Anal. Biochem.* 1975, 64, 284-288].

Preparation of Boc-NH-PEG-flGlu-(NHS)$_2$ (Compound 5)

Compound 4 (3.33 grams; 0.67 mmol) was dissolved in 100 mL of anhydrous CH$_2$Cl$_2$, and NHS (469 mg; 4.07 mmol) and DCC (1.114 gram; 5.4 mmol) were added. The reaction mixture was stirred at room temperature overnight, and was thereafter filtered and dropped into 1 liter of cold diethyl ether. After 1 hour at −20° C., the precipitate was filtered and dried under vacuum to afford Compound 5 (3.1 mg, 89.5% yield). The degree of activation was 91%, determined on the basis of the amino group modification of an equimolar solution of Gly-Gly as reported elsewhere [see, Pasut et al., 2005, supra].

Preparation of Boc-NH-PEG-βGlu-(βGlu)$_2$-(COOH)$_4$ (Compound 6; PEG-dendrimer)

βGlu (532 mg; 3.6 mmol) was dissolved in 200 mL of 0.1 M borate buffer/CH$_3$CN (3:2) mixture at pH 8.0, and Compound 5 (3.09 mg; 0.6 mmol) was added to the solution. The reaction mixture was treated as described hereinabove for preparing Compound 4 and the product was similarly purified so as to afford Compound 6 (2.9 grams, 92% yield).

Preparation of Boc-NH-PEG-βGlu-(βGlu)$_2$-(NHS)$_4$ (Compound 7)

Compound 6 (1.7 gram; 0.32 mmol) was with NHS and DCC as described hereinabove for preparing Compound 5, so as to afford Compound 7 (1.52 gram, 89% yield). The degree of activation was 81%.

Preparation of Boc-NH-PEG-βGlu-(βGlu)$_2$-(ALN)$_4$ (Compound 8)

ALN (802 mg; 2.46 mmol) was dissolved in 0.1 M borate buffer at pH 8.0, Compound 7 (1.45 gram; 0.25 mmol) was added and the reaction mixture was stirred for 5 hours at room temperature. The product was purified as described hereinabove for Compound 4, to thereby afford Compound 8 (1.3 gram, 83% yield).

Preparation of PEG-ALN (Compound 1)

Compound 8 (1.2 gram) was dissolved in 4 mL of a mixture of CH$_2$CH$_2$/CF$_3$COOH/H$_2$O (55.4:45.4:0.1 volume ratio) and the reaction mixture was stirred at room temperature for 3 hours, and was thereafter evaporated to remove TFA and the solvents. The obtained oil was dissolved in CH$_2$Cl$_2$ and the solution was dropped into 400 mL of diethyl ether. The precipitate was filtered and dried under vacuum to afford the PEG-ALN conjugate Compound 1 (1.1 grams, 91% yield).

Preparation of $H_2N$-PEG-βGlu-(βGlu)$_2$-(COOH)$_4$
(Compound 9; PEG-dendron)

Compound 6 (1.2 gram) was dissolved in 4 mL of a mixture of $CH_2CH_2/CF_3COOH/H_2O$ (55.4:45.4:0.1 volume ratio) and the reaction mixture was stirred at room temperature for 3 hours to remove the protecting group t-Boc, and was thereafter evaporated to remove TFA and the solvents. The obtained oil was dissolved in $CH_2Cl_2$ and the solution was dropped into 400 mL of diethyl ether. The precipitate was filtered and dried under vacuum to afford Compound 9 (1.17 grams, 97% yield).

Preparation of Compound 2 (PEG-PTX)

SPTX (190 mg; 0.2 mmol) was dissolved in anhydrous DMF (5 mL), and a solution of HOBT (40.5 mg; 0.3 mmol), EDC (40.2 mg; 0.22 mmol) in anhydrous DMF (2 mL) was added. The reaction mixture was stirred for 5 hours at room temperature and then 530 mg of Compound 9, dissolved in 5 mL of DMF, were added and the obtained mixture was allowed to react 24 hours under stirring at room temperature. The reaction mixture was thereafter reduced to small volume (about 5 mL) under vacuum and the product was purified from excess of SPTX by gel-filtration chromatography using Sephadex LH-20 resin eluted with DMF. The fractions containing Compound 2 were collected in a round bottom flask and DMF was evaporated under vacuum. The residue was dissolved in 5 mL of anhydrous $CH_2Cl_2$ and the solution was dropped into 500 mL of cold diethyl ether under stirring. After 1 hour at −20° C., the precipitate was filtered and dried under vacuum, to thereby afford the PEG-PTX conjugate (Compound 2; 425 mg; 69.2% yield.

Preparation of Compound 3 (PTX-PEG-ALN)

SPTX (190 mg; 0.2 mmol) was dissolved in anhydrous DMF (5 mL), and a solution of HOBT (40.5 mg; 0.3 mmol) and EDC (40.2 mg; 0.22 mmol), in anhydrous DMF (2 mL), was added. The reaction mixture was stirred for 5 hours at room temperature and then 650 mg of Compound 1 (PEG-ALN), dissolved in 5 mL DMF, were added and the obtained mixture was allowed to react 24 hours under stirring at room temperature. The reaction mixture was reduced to small volume (about 5 mL) under vacuum and the product was purified from the excess SPTX by gel-filtration chromatography using Sephadex LH-20 resin eluted with DMF. The fractions containing Compound 3 were collected in a round bottom flask and DMF was evaporated under vacuum. The residue was dissolved in 5 mL of anhydrous $CH_2Cl_2$ and the solution was dropped into 500 mL of cold diethyl ether under stirring. After 1 hour at −20° C., the precipitate was filtered and dried under vacuum, to thereby afford the PTX-PEG-ALN conjugate (Compound 3; 550 grams; 74.7% yield).

Synthesis of FITC labeled PTX-PEG, PEG-ALN and PTX-PEG-ALN conjugates

The chemical structures of FITC labeled-PEG-ALN (FITC labeled-Compound 1) FITC labeled-PEG-PTX (FITC labeled-Compound 2) and FITC labeled-PTX-PEG-ALN (FITC labeled-Compound 3), exemplary FITC labeled-conjugates according to some embodiments of the present invention, are depicted in FIGS. 1A, 1B and 1C, respectively, wherein X is the structure stands for FITC coupled to a lysine residue.

An exemplary synthetic pathway for preparing PTX-PEG-ALN (FITC labeled-Compound 3) is depicted in FIG. 3.

The syntheses of FITC labeled-conjugates (FITC labeled-Compounds 1, 2 and 3) was performed by exploiting the same chemical strategy used for the preparation of non-labeled conjugates, as described hereinabove, and attachment of FITC was performed by incorporating a Lys residue and exploiting the ε amino group of Lys for coupling with FITC (see, FIG. 3).

Preparation of Boc-NH-PEG-L-Lys(εFmoc)-OH
(Compound 13)

L-Lys(εFmoc)-OH (313 mg; 0.67 mmol) was dissolved in 50 mL of $H_2O/CH_3CN$ (3:2) mixture having pH=8, Boc-NH-PEG-NHS (MW 4928 Da; 1.1 gram; 0.2 mmol) was added and the reaction mixture was let to proceed for 5 hours under stirring at room temperature. The pH was thereafter adjusted to about 4.5 by addition of 0.2N HCl and Compound 13 was purified from the excess of L-Lys(εFmoc)-OH by extractions with $CHCl_3$ (5×80 mL). The organic phase was dried over anhydrous $Na_2SO_4$, concentrated under vacuum and was precipitated from 500 mL of diethyl ether. The product was recovered by filtration and dried under vacuum to thereby afford the Boc-NH-PEG-L-Lys(εFmoc)-OH (Compound 13; 1.0 grams; 83.0% yield). The product was characterized by the Snaider Sobociski assay as described hereinabove, to verify the absence of free L-Lys(εFmoc)-OH.

$^1$H-NMR (d$_6$-DMSO): δ=1.3 (s, 9H, Boc), 3.4-3.6 (s, 422H, $CH_2$ PEG), 7.2-7.5 (m, 8H, Fmoc group), 7.7 (d, 4H, Fmoc group), 7.9 (d, 4H, Fmoc group) ppm.

Preparation of Boc-NH-PEG-L-Lys(εFmoc)-NHS
(Compound 14)

Compound 13 (800 mg) was activated by reacting it with NHS and DCC, as described hereinabove for Compounds 5 and 7, to afford Compound 14 (94% yield).

Preparation of Boc-NH-PEG-L-Lys(εFmoc)-βGlu-
(βGlu)$_2$-(COOH)$_4$ (Compound 15; FITC labeled-
PEG dendron)

Compound 14 was reacted with βGlu as described hereinabove for Compounds 4 and 6, to afford Compound 15 (89.1% yield).

Preparation of Boc-PEG-L-Lys(εNH$_2$)-βGlu-
(βGlu)$_2$-(COOH)$_4$ (Compound 16)

Compound 15 (530 mg) was dissolved in 10 mL of a mixture of DMF and 20% (v/v) piperidine, and the solution was stirred at room temperature for 15 minutes to remove the Fmoc protecting group. The reaction mixture was then evaporated to remove the solvent, the residue was dissolved in 5 mL of $CH_2Cl_2$ and the solution was dropped into 300 mL of diethyl ether. The precipitate was filtered and dried under vacuum to afford Compound 16 (92.7% yield).

Preparation of Boc-PEG-L-Lys(εFITC)-βGlu-
(βGlu)$_2$-(COOH)$_4$ (Compound 17)

FITC (38.9 mg) was dissolved in DMF (10 mL), and Compound 16 (470 mg) and Et$_3$N (11 μL) were added. The reaction mixture was stirred at room temperature for 5 hours and excess of FITC was thereafter removed by extensive dialysis vs. 0.1 M phosphate buffer pH=8.0 using a membrane with cut-off 3500 Da. The last step of dialysis was performed overnight with $H_2O$ mQ to eliminate the phosphate salts. The product was then lyophilized to thereby afford Compound 17 (86.4% yield). Compound 17 was analyzed by RP-HPLC to verify the absence of free FITC.

Preparation of Boc-PEG-L-Lys(εFITC)-βGlu-(βGlu)$_2$-(ALN)$_4$ (Compound 18)

Compound 17 (244 mg) was activated with NHS/DCC, as described hereinabove for Compound 7 and the NHS-activated product was thereafter coupled to ALN, as described hereinabove for Compound 8, to afford Compound 18 (79.2% yield).

Preparation of FITC labeled-PEG-ALN (FITC labeled-Compound 1)

The Boc protecting group was removed from Compound 18 by TFA hydrolysis procedure as described hereinabove for the preparation of Compound 1, to thereby afford FITC labeled-Compound 1 (90.4% yield).

Preparation of FITC labeled-PTX-PEG (FITC labeled-Compound 2)

Compound 17 was reacted to remove the Boc protecting group as described hereinabove for Compound 9, and the obtained product was reacted with SPTX, as described hereinabove for Compound 2, to thereby afford FITC labeled-Compound 2 (65.9% yield).

Preparation of FITC labeled-PTX-PEG-ALN (FITC labeled-Compound 3)

FITC-labeled Compound 1 was coupled to SPTX, as described hereinabove for Compound 3, to thereby afford FITC labeled-Compound 3 (62.8% yield).

Physicochemical Properties of the Conjugates

The content of ALN in the PTX-PEG-ALN (Compound 3) and PEG-ALN (Compound 1) non-labeled and labeled conjugates was determined spectrophotometrically via the chromophoric complex formed between ALN and $Fe^{3+}$ ions in perchloric acid, and against a calibration graph of ALN, as described in the Methods section hereinabove.

The content of free PTX in the PTX-PEG-ALN and PTX-PEG conjugates was determined directly by RP-HPLC analysis of the conjugates when dissolved in DMSO. Free PTX impurity in all conjugates was below 0.6% (w/w).

Determination of the total PTX amount in the conjugates was performed by RP-HPLC after hydrolysis of the conjugates to release the linked drug.

The content of FITC in the labeled conjugates was measured spectrophotometrically using c 64185 $M^{-1}$ $cm^{-1}$ in PBS Ph=8.

The hydrodynamic diameter and size distribution of PTX-PEG-ALN and of PTX-PEG conjugates were evaluated using laser light scattering microscopy with Nanoparticle Tracking Analysis (NTA) technology (NanoSight LM20™, Salisbury, UK). The obtained data is presented in FIGS. 4A and 4B. As shown therein, the mean hydrodynamic diameter of both PTX-PEG-ALN and PTX-PEG conjugates in PBS pH 7.4 was about 190 nm.

The physicochemical properties of PEG conjugates and the FITC labeled conjugates are presented in table 1.

TABLE 1

| Product | Molecular Weight | % PTX loading wt/wt | % ALN loading wt/wt | Micelles size (nm) |
|---|---|---|---|---|
| PEG | 4667 Da | — | — | — |
| PEG-ALN | 5913 Da | — | 11.9% | — |
| PTX-PEG | 5620 Da | 6% | — | 190 nm |
| PTX-PEG-ALN | 6850 Da | 4.68% | 11% | 200 nm |
| FITC-PEG-ALN | 6430 Da | — | 7.2% | — |
| FITC-PEG-PTX | 6137 Da | 4.26 | — | — |
| FITC-PEG-PTX-ALN | 7367 Da | 3.6% | 6.9% | — |

Evaluation of the Stability of the Conjugates at Different pH Values and at Plasma:

The stability of the exemplary PTX-PEG-ALN conjugate, Compound 3, was evaluated in buffer solutions at physiological pH (7.4), at lysosomal pH (5), and in mice plasma, upon incubation at 37° C. for 48 hours, and degradation of the conjugates was monitored by RP-HPLC. The obtained data is presented in FIG. 5A. At pH 7.4 and in plasma, about 50% of the PTX-PEG-ALN conjugate was degraded within the first 1 hour, and the remaining conjugate was degraded within 24 hours. Similar results were found with PTX-PEG.

The stability of the conjugates micelles at 37° C. during 48 hours was also monitored by dynamic light scattering, and the results are presented in FIG. 5B. As shown therein, the micelles stability was in line with the kinetic of PTX release. The micelles of the PTX-PEG-ALN and PTX-PEG conjugates preserved the same size for up to 24 hours when incubated at pH 5, whereas at pH 7.4 the same micelles were stable for 3 hours, after which the size of the samples starts to increase owing to the release of PTX from the conjugates. Th released PTX is insoluble in the aqueous buffer and precipitates, thus forming a suspension and destabilizing the system.

Example 2

In Vitro Studies

Materials and Experimental Methods

Dulbecco's modified Eagle's medium (DMEM), RPMI 1640, Fetal bovine serum (FBS), Penicillin, Streptomycin, Nystatin, L-glutamine, Hepes buffer, sodium pyruvate, and fibronectin were obtained from Biological Industries Ltd. (Kibbutz Beit Haemek, Israel).

EGM-2 medium was purchased from Cambrex (Walkersville, Md., U.S.A).

Matrigel® matrix was purchased from BD Biosciences, USA.

Peroxidase Block was purchased from Merck, Germany.

Human umbilical vein endothelial cells (HUVEC) were obtained from Cambrex (Walkersville, Md., U.S.A).

Hydroxyapatite Binding Assay:

PEG, PEG-ALN and PTX-PEG-ALN conjugates were dissolved in phosphate buffered saline (PBS), pH 7.4 (5 mg/mL). The conjugate solution (600 μL) was incubated with hydroxyapatite (HA) powder (30 mg), in 600 μL PBS, pH 7.4. $NH_2$-PEG-(COOH)$_4$ ($H_2N$-PEG-βGlu-(βGlu)$_2$-(COOH)$_4$; PEG-dendron, Compound 9, denoted as PEG) was used as control. Incubated samples were centrifuged at 7000 RPM for 3 minutes and a sample from the upper layer (100 μL) was collected after 0, 2, 5, 10 and 60 minutes. Fast protein liquid chromatography (FPLC, AKTA™ Purifier®, Amersham Biosciences) analysis using HiTrap™ desalting column (Amersham®) was used for detection of unbound conjugates in the samples (FPLC conditions: AKTA™ Purifier®, mobile phase 100% DDW, 2 mL/minute, X=215 nm). HA-binding kinetic analysis of the conjugates was performed using the Unicorn® AKTA™ software. Areas under the curve (AUC) were calculated from chromatographs at each time point. AUC of each HA-incubated conjugate chromatogram was normalized to percent AUC of conjugate sample in the absence of HA.

Cell Culture:

PC3 human prostate adenocarcinoma MDA-MB-231 and MDA-MB-231 cells were cultured in DMEM supplemented with 10% Fetal Bovine Serum (FBS), 100 µg/mL Penicillin, 100 U/mL Streptomycin, 12.5 U/mL Nystatin and 2 mM L-glutamine.

4T1 cells were cultured in RPMI 1640 supplemented with 10% FBS, 100 µg/mL Penicillin, 100 U/mL Streptomycin, 12.5 U/mL Nystatin, 2 mM L-glutamine, 10 mM Hepes buffer, and 1 mM sodium pyruvate.

Human umbilical vein endothelial cells (HUVEC) were grown according to the manufacturer's protocol in EGM-2 medium (Cambrex).

Cells were grown at 37° C.; 5% $CO_2$.

Cell Viability Assays:

PC3 cells were plated onto 96 well plate ($5 \times 10^3$ cells/well) in DMEM supplemented with 5% FBS and incubated for 24 h (37° C.; 5% $CO_2$). Following 24 hours of incubation, medium was replaced with DMEM containing 10% FBS. Cells were exposed to the combination of PTX and ALN, each drug alone, and with PEG, PEG-ALN, PEG-PTX, PTX-PEG-ALN conjugates at serial concentrations for 72 hours. Following incubation, PC3 cells were counted by MTT.

HUVECs were plated onto 24-well plate ($1.5 \times 10^4$ cells/well) in growth factors reduced media, (EBM-2, Cambrex, USA) supplemented with 5% FBS. Following 24 hours of incubation (37° C.; 5% $CO_2$), medium was replaced with EGM-2 (Cambrex, USA). 4T1 and MDA-MB-231 cells were plated onto 96 well plate ($5 \times 10^3$ cells/well) in DMEM supplemented with 5% FBS and incubated for 24 hours (37° C.; 5% $CO_2$). The medium was thereafter replaced with DMEM containing 10% FBS and the cells were challenged with a combination of free PTX and ALN, with each free drug alone, and with PEG, and the exemplary PEG-ALN, PTX-PEG, PTX-PEG-ALN conjugates, at serial concentrations, for up to 72 hours. Following incubation, HUVEC were counted by Coulter Counter.

4T1 and MDA-MB-231 cells viability was measured by Thiazolyl Blue Tetrazolium Blue (MTT) (Sigma-Aldrich, Israel) as follows: a 30 µl solution of 2 mg/mL MTT was added to wells containing cells grown at 100 µl medium. Following 5 hours incubation, the medium was replaced with dimethyl sulfoxide (DMSO) until blue color was developed. Viability was measured spectrophotometrically at 560 nm.

Migration Assay:

Cell migration assay was performed using modified 8 µm Boyden chambers Transwells® (Costar Inc., USA) coated with 10 µg/mL fibronectin (Biological industries, Beit Haemek, Israel). PC3 ($15 \times 10^4$ cells/100 µL) were challenged with a combination of free PTX (10 nM) and ALN (46 nM), each free drug alone, and with PEG, PEG-ALN, PTX-PEG, PTX-PEG-ALN conjugates, at equivalent PTX and ALN concentrations, and were added to the upper chamber of the transwells for 2 hours incubation prior to migration towards DMEM containing 10% FBS. Following incubation, cells were allowed to migrate to the underside of the chamber for 4 hours in the presence or absence of 10% FBS in the lower chamber. Cells were then fixed and stained (Hema 3 Stain System; Fisher Diagnostics, USA). The stained migrated cells were imaged using Nikon TE2000E inverted microscope integrated with Nikon DS5 cooled CCD camera by 10× objective, brightfield illumination. Migrated cells from the captured images per membrane were counted using NIH image software. Migration was normalized to percent migration, with 100% representing migration to medium containing FBS.

Capillary-Like Tube Formation Assay:

The surface of 24-well plates was coated with Matrigel® matrix (50 µL/well) (BD Biosciences, USA) on ice and polymerization was thereafter effected at 37° C. for 30 minutes. HUVEC ($3 \times 10^4$) were challenged with a combination of free PTX (5 nM) and ALN (23 nM), with each free drug alone, and with PEG, PEG-ALN, PTX-PEG and PTX-PEG-ALN conjugates, at equivalent concentrations, and were thereafter seeded on coated plates in the presence of complete EGM-2 medium. After 8 hours of incubation (37° C.; 5% $CO_2$), wells were imaged using Nikon TE2000E inverted microscope integrated with Nikon DS5 cooled CCD camera by 4× objective, brightfield technique.

Red Blood Cells (RBC) Lysis Assay:

Rat RBC solution (2% w/w) was incubated with serial dilutions of a combination of free PTX and free ALN, PEG, and a PTX-PEG-ALN conjugate as described herein at equivalent PTX and ALN concentrations, for 1 hour at 37° C. Negative controls were PBS and Dextran (MW of about 70000 Da) while positive controls were 1% w/v solution of Triton X100 (100% lysis) and poly(ethylenimine) (PEI). Following centrifugation, the supernatant was drawn off and its absorbance measured at 550 nm using a microplate reader (Genios, TECAN). The results were expressed as percent of hemoglobin released relative to the positive control (Triton X100).

Statistical Methods:

In vitro data is expressed as mean±standard deviation (s.d.). Statistical significance was determined using an unpaired t-test. $P<0.05$ was considered statistically significant. All statistical tests were two-sided.

Results

Binding of the Conjugates to Hydroxyapatite (HA):

The bisphosphonate ALN, known as bone targeting moiety with strong bone affinity, was chosen as the bone targeting moiety. The binding capacity of the exemplary ALN-containing conjugates to bone mineral was evaluated. Hydroxyapatite was used as a model mimicking bone tissue. An in vitro HA binding assay and FPLC analysis using HiTrap™ desalting column was performed, as described hereinabove. As shown in FIG. 6, following 5 minutes incubation, 80% or 90% of PTX-PEG-ALN or PEG-ALN conjugates, respectively, were bound to HA and reached a plateau, indicating the high binding capacity of the conjugates to bone minerals.

Biocompatibility of PTX-PEG-ALN Conjugate:

The biocompatibility of PTX-PEG-ALN was evaluated using rat red blood cell (RBC) hemolysis assay. Rat RBC solution was incubated with serial concentrations of a combination of PTX and ALN, PEG, and the PTX-PEG-ALN conjugate at equivalent PTX and ALN concentrations, a PTX vehicle (1:1:8 Ethanol:Cremophor EL:Saline), and polyethylene imine (PEI) which served as control for hemolysis. The obtained data is presented in FIG. 7 and shows that the PTX-PEG-ALN conjugate (black squares) did not exhibit detectable RBC hemolysis at all tested concentrations up to 5 mg/mL (the estimated blood concentration after in vivo administrations is about 0.5 mg/mL). PTX vehicle cytotoxicity is known on normal non-proliferating cells, and indeed, a RBC hemolysis of about 8% was observed in RBCs incubated with PTX vehicle (black diamonds). About 5% hemolysis was observed in RBCs incubated with the combination of PTX plus ALN as free drugs (blank squares) at the highest equivalent to the conjugate concentration of 5 mg/mL. This hemolysis observed is probably caused by the Cremophor EL vehicle in which these drugs were dissolved.

Anti-Proliferative Effect of PC3 Cells:

The taxane PTX is a potent cytotoxic agent approved as first line of therapy for metastatic breast cancer, and it is being tested in the clinic in combination with other chemotherapeutic agents for the treatment of metastatic prostate cancer. To evaluate whether PTX retained its cytotoxic activity following conjugation with PEG polymer, a proliferation assay of PC3 human prostate adenocarcinoma cells was performed. The obtained data is presented in FIGS. 8A and 8B. PEG-β-Glutamic acid Dendron (denoted as PEG) served as control and was found to be non-toxic at any of the concentrations tested. The proliferation of PC3 cells was similarly inhibited by PTX-PEG and PTX-PEG-ALN conjugates, by free PTX alone and by a combination of free PTX and free ALN, all exhibiting an $IC_{50}$ of 25-60 nM, and indicating the PTX maintains its potent cytotoxicity when conjugates to PEG.

ALN alone was found to be toxic only at the highest concentration tested of 10 µM, however ALN bound to PEG at equivalent concentration was not toxic at any of the concentrations tested.

Effect on the Migration of PC3 Human Prostate Adenocarcinoma Cells:

The effect of the exemplary PTX-PEG, PEG-ALN and PTX-PEG-ALN conjugates on the ability of PC3 cells to migrate towards FBS was evaluated compared to the free drugs alone, at equivalent concentrations, and to PEG-β-Glutamic acid dendron, denoted as PEG. The results are presented in FIG. 9 and show that migration of PC3 incubated with both PTX-PEG and PTX-PEG-ALN conjugates and the combination of free PTX plus ALN towards PBS was similarly inhibited by about 70%.

Anti-Proliferative Effect of Murine 4T1 and Human MDA-MB-231 Adenocarcinoma of the Mammary Cell Lines:

To evaluate whether PTX and ALN retained their cytotoxic activity following conjugation with PEG polymer, a proliferation assay of 4T1 and MDA-MB-231 cells was performed. The results are presented in FIG. 10A (for 4T1 cells) and FIG. 10B (MDA-MB-231 cells). As shown in FIG. 10A, proliferation of 4T1 cells was inhibited in a similar manner by all PTX-containing formulations, exhibiting an $IC_{50}$ of about 10 nM, and in a similar manner also for a combination of PTX and ALN as free drugs and for PTX-PEG-ALN conjugate, exhibiting an $IC_{50}$ of about 20 nM.

As shown in FIG. 10B, the proliferation of MDA-MB-231 cells was also inhibited by all PTX-containing formulations, exhibiting an $IC_{50}$ of about 1 nM, and in a similar manner also for a combination of PTX and ALN as free drugs and for PTX-PEG-ALN conjugate, exhibiting an $IC_{50}$ of about 10 nM.

The PEG-β-Glutamic acid dendron, denoted as PEG, served as control and was non-toxic at all the concentrations tested. ALN alone was found to be toxic only at the highest concentration tested of 10 µM, however ALN bound to PEG at equivalent concentration was not toxic at all the concentrations tested.

Anti-Angiogenic Properties:

To assess whether similarly to PTX, the conjugates described herein possess anti-angiogenic properties, endothelial cell proliferation, capillary-like tube formation and migration assays were carried out on human umbilical vein endothelial cells (HUVEC). FIG. 11A presents the effect of various concentrations of a combination of free PTX plus ALN (blank squares), PTX (blank triangles), ALN (blank circles), and equivalent concentrations of PEG (black diamonds), PTX-PEG-ALN (black squares), PTX-PEG (black triangles) and PEG-ALN (black circles) conjugates on the proliferation of HUVEC. X-axis is presented at a logarithmic scale. As shown in FIG. 11A, the proliferation of HUVEC was inhibited similarly by all PTX-containing formulations, exhibiting an $IC_{50}$ of about 2 nM, and in a similar manner also for a combination of PTX and ALN as free drugs and for PTX-PEG-ALN conjugate, exhibiting an $IC_{50}$ of about 4 nM.

FIG. 11B presents the effect of a combination of PTX and ALN as free drugs, PTX and ALN each alone, and equivalent concentrations of PEG, PTX-PEG-ALN, PTX-PEG and PEG-ALN conjugates on the ability of HUVEC to migrate towards VEGF. As shown in FIG. 11B, the migration of HUVEC incubated with both PTX-PEG and PTX-PEG-ALN conjugates and the combination of free PTX and ALN towards VEGF was inhibited by about 80%.

Having shown that free and conjugated PTX and ALN possess anti-angiogenic potential by inhibiting the proliferation and migration of HUVEC, the effect of the conjugates on the ability of HUVEC to form capillary-like tube structures on Matrigel® was measured as being indicative of an additional crucial step in the angiogenic cascade of events.

FIG. 12A presents representative images of capillary-like tube structures of HUVEC seeded on Matrigel® following the indicated treatment (scale bar represents 100 µm), demonstrating the inhibition of capillary-like tube formation by all PTX-containing formulations (with and without ALN).

In terms of capillary length, as shown in FIG. 12B, the combination of PTX and ALN as free drugs inhibited the formation of tubular structures of HUVEC by about %. Both PTX-PEG and PTX-PEG-ALN conjugates at PTX-equivalent concentrations inhibited the formation of the tubular structures of HUVEC by about 50%.

The concentrations of treatments used in both migration and capillary-like tube formation assays on HUVEC were tested and found as non-cytotoxic at the indicated incubation times, but rather specifically inhibited the ability to migrate and form capillary-like tubes.

Overall, the in vitro studies conducted showed that PTX, when bound with PEG, exhibited similar cytotoxicity to various cell lines, compared with free PTX, suggesting that PTX can be released from the conjugates and achieve similar tumor cells killing efficacy. Inhibition of proliferation, capillary-like tube formation, and migration of endothelial cells revealed that both PTX-PEG and PTX-PEG-ALN conjugates possesses anti-angiogenic properties and are as potent as the free drugs at equivalent concentrations. The improved binding capacity to HA demonstrated the combined targeting effect exhibited by ALN-containing conjugates.

Example 3

In Vivo Studies

Materials and Experimental Methods

Materials:

All monoclonal antibodies were purchased from BD Biosciences and used for flow cytometry analysis in accordance with the manufacturer's protocols.

Primary rat anti-murine CD34 antibody (MEC 14.7) was from Abcam, (Cambridge, Mass.). Rabbit anti-rat antibody, anti-rabbit horseradish peroxidase-conjugated antibody (ABC detection kit) and ImmPACT™ DAB diluent kit were from Vector Laboratories (Burlingame, Calif., USA).

pEGFPLuc plasmid was from Clontech (Mountain View, Calif., USA). Nuclear staining was from Procount, BD Pharmingen (San Jose, Calif., USA).

7-aminoactinomycin D (7AAD) was from Chemicon (Billerica, Mass.).

Dextran (MW of about 70000) and all other chemical reagents, including salts and solvents were purchased from Sigma-Aldrich, Israel.

PC3 human prostate adenocarcinoma, MDA-MB-231 human mammary adenocarcinoma and 4T1 murine mammary adenocancinoma cell lines were purchased from the American Type Culture Collection (ATCC).

Balb/C mice were obtained from Harlan.

SCID mice were obtained from Harlan.

Human embryonic kidney 293T (HEK 293T) cells were obtained from ATCC.

All other reagents and solvents were obtained from known vendors.

Pharmacokinetic Studies in Mice:

Pharmacokinetics of PTX, PTX-PEG and PTX-PEG-ALN were determined in 30 female Balb/C mice (23-25 grams). The mice were randomly divided in three groups of 10 animals. 150 μL of PTX in 1:1:8 Ethanol:Cremophor EL:Saline, PTX-PEG conjugate as described herein in PBS pH 6 or PTX-PEG-ALN conjugate as described herein in PBS pH 6 (dose: 10 mg/Kg PTX equiv.) were administered via tail vein to mice anaesthetized with 5% isoflurane gas (mixed with $O_2$ in enclosed cages). At predetermined times, two blood samples (150 μL) were withdrawn from the retro-orbital plexus/sinus of two animals, with a heparinized capillary, and then centrifuged at 1,500 g for 15 minutes. To 50 μL of plasma, 350 μL of $CH_3CN$ was added for protein precipitation and the resulting mixture was centrifuged at 20,000 g for 5 minutes. A 300 μL aliquot of the supernatant was collected and freeze-dried. The residue was dissolved in 50 μL of $CH_3OH$ and analyzed by RP-HPLC under the condition reported hereinabove. For PTX-PEG and PTX-PEG-ALN conjugates, the residues after freeze-drying were also hydrolyzed by incubation with a solution of 2% NaOH 2N as reported above.

Generation of mCherry-Infected Human MDA-MB-231 and Murine 4T1 Mammary Adenocarcinoma Cell Lines:

mCherry was subcloned from pART7-mCherry (provided by A. Avni from Tel Aviv University), into pQCXIP (Clontech). Human embryonic kidney 293T (HEK 293T) cells were co-transfected with pQC-mCherry and the compatible packaging plasmids (pMD.G.VSVG and pGag-pol.gpt). Forty eight (48) hours following transfection, the pQC-mCherry retroviral particles containing supernatant was collected. 4T1 and MDA-MB-231 cells were infected with the retroviral particles media, and 48 hours following the infection, mCherry positive cells were selected by puromycin resistance.

Evaluation of Antitumor Activity of PTX-PEG-ALN Conjugate:

A syngeneic mouse model of mammary adenocarcinoma was established by injecting Balb/c female mice with 100 μl of $4 \times 10^5$ mCherry-labeled 4T1 cells intra-tibia. Therapy was initiated one day following tumor cells inoculation. Mice were randomly divided into 9 groups (n=6 mice/group) and intravenously (i.v.) injected with 100 μl PTX (15 mg/kg), ALN (35 mg/kg), a combination of PTX and ALN as free drugs, PEG, and the PTX-PEG, PEG-ALN, or PTX-PEG-ALN conjugates at equivalent concentrations. Mice injected intravenously with commercial the PTX vehicle 1:1:8 Ethanol:Cremophor EL:Saline or saline were used as controls.

A xenograft mouse model was established by injecting female SCID mice with 100 μl of $1 \times 10^5$ mCherry-labeled MDA-MB-231 cells intra-tibia.

Therapy was initiated 10 days following tumor inoculation, when most mice had fluorescent signals indicating tumors uptake. Mice were divided into 5 groups (n=6 mice/group) and the mean fluorescence intensity was approximately equivalent for all groups. These groups were randomly assigned and received intravenuous (i.v.) injections of 100 μl PTX (15 mg/kg) plus ALN (35 mg/kg), PTX (7.5 mg/kg) plus ALN (17.5 mg/kg), PTX-PEG-ALN conjugate at equivalent concentration, and controls of PTX-vehicle, or saline. All treatments for both mouse models were injected i.v. via the tail vain, every other day, 5 injections. Tumor progression was monitored by CRI™ Maestro non-invasive intravital imaging system. At termination, tibias were removed and analyzed, as described hereinbelow. Data is expressed as mean±SEM.

Body Distribution of FITC Labeled PEG, PTX-PEG, PEG-ALN and PTX-PEG-ALN Conjugates:

SCID mice bearing MDA-MB-231 tumors in the tibia were injected i.v. (intravenously) with FITC-labeled PEG, and the FITC-labeled PTX-PEG, PEG-ALN and PTX-PEG-ALN conjugates. Accumulation of the conjugates in the tumor was assessed at different time points (0, 2, 4, 6, and 8 hours) by measuring fluorescence intensity signal. At termination (after 8 hours), tumors, organs and bones were excised and imaged. Organs were imaged using non-invasive imaging system (CRI Maestro™) Fluorescence was determined using defined regions of interest (ROI) measurements on tumors and other tissues. Time dependent tumor contrast profile was determined by the ratio between fluorescence intensities of tumors and those of normal skin. Data were expressed as mean±standard deviation (s.d.) (n=3).

Measurement of Circulating Endothelial Cells (CEC) and Circulating Endothelial Progenitor (CEP) by Flow Cytometry:

Blood was obtained from anaesthetized mice by retro-orbital sinus bleeding. CEC and CEP were quantitated using flow cytometry, as described in Shaked et al. [in *Cancer Cell* 2005; 7: 101-111]. Briefly, 24 hours after treatment, blood was collected in tubes containing EDTA to avoid clotting. Monoclonal antibodies were used to detect CEC and CEP population with the following antigenic phenotypes: CD13+/VEGFR2+/CD45−/dim. CEP population was also CD117+. Nuclear staining was used in some experiments to exclude platelets or cellular debris. 7-Aminoactinomycin D (7AAD) was used to distinguish apoptotic and dead cells from viable cells. After red cell lysis, cell suspensions were analyzed and at least 200,000 cells per sample were acquired. Analyses were considered informative when an adequate number of events (i.e. >50, typically 50-150) was collected in the CEC and CEP enumeration gate in untreated control animals.

Percentages of stained cells were determined and compared with appropriate negative controls. Positive staining was defined as being greater than non-specific background staining.

Flow cytometry studies were performed on CyanADP flow cytometer (Beckman Coulter) and analyzed with Summit (Beckman Coulter) software. Data is expressed as mean±standard error of the mean (SEM).

White Blood Cell (WBC) Counts:

Blood was obtained from anaesthetized mice by retro-orbital sinus bleeding. Twenty four hours after treatment, blood was collected in tubes containing 0.1 M EDTA to avoid clotting. Samples were counted no longer than five minutes after blood was drawn from mice. Ten µl of blood samples were mixed with 90 µl of track solution (1% acetic acid in DDW), and cells were counted by a Z1 Coulter® Particle Counter (Beckman Coulter™). Data is expressed as mean±s.e.m.

Immunohistochemistry:

Immunohistochemistry of tumors in the tibia was performed using samples fixed with 4% paraformaldehyde, following decalcification in EDTA and paraffin embedding by the standard procedure. Paraffin sections of 4 µm were deparaffinized, rehydrated, and stained by hematoxylin and eosin (H&E). For CD34 staining, slides were deparaffinized and pre-treated with 10 mM citrate buffer, pH=6.0, for 20 minutes in a steam pressure cooker (Decloaking Chamber, BioCare Medical, Walnut Creek, Calif.).

All further steps were performed at room temperature in a hydrated chamber. Slides were covered with Peroxidase Block (Merck, Germany) for 10 minutes to quench endogenous peroxidase activity, followed by incubation with 2% of horse serum in 50 mM Tris-HCl, pH 7.4, for 30 minutes to block non-specific binding sites. Primary rat anti-murine CD34 antibody (MEC 14.7 1:50 dilution; Abcam, Cambridge, Mass.) was applied in 1% rabbit serum albumin in Tris-HCl, pH 7.4 at 4° overnight. Slides were washed in 50 mM TrisHCl, pH 7.4 and rabbit anti-rat antibody (1:750 dilution; Vector Laboratories, Calif., USA) was applied for 30 minutes. Following further washing, immunoperoxidase staining was developed using HistoMark TrueBlue peroxidase system (KPL, USA) per the manufacturer instructions and counterstained with safranin. Microvessel density (MVD) was calculated as previously described [Weidner et al., *N Engl J Med* 1991; 324: 1-8].

Statistics:

In vivo data is expressed as mean±s.e.m. Statistical significance was determined using an unpaired t-test. P<0.05 was considered statistically significant. All statistical tests were two-sided.

Results

Pharmacokinetic Studies:

Pharmacokinetics of PTX dissolved in 1:1:8 Ethanol:Cremophor EL:Saline, and of the exemplary conjugates PTX-PEG and PTX-PEG-ALN were determined in mice. The serum levels of PTX were evaluated by RP-HPLC and the obtained data are presented in FIG. 14. As shown in FIG. 14, after administration of free PTX, high levels of the drug were recorded, however at 5 minutes post-injection, the PTX concentration decreased dramatically, and it was not detectable at 60 minutes. On the contrary, the two conjugates showed a marked half-life prolongation, with detectable levels of PTX after 3 hours for PTX-PEG and after 24 hours for PTX-PEG-ALN. In particular, elimination half-lives ($T_{1/2\beta}$) were 15.1 minutes, 77.9 minutes and 85.5 minutes for PTX, PTX-PEG and PTX-PEG-ALN, respectively.

Table 2 below summarizes the pharmacokinetic parameters obtained in these studies, and clearly demonstrate the prolonged blood circulation of both the PTX-PEG and PTX-PEG-ALN conjugate.

TABLE 2

| Parameter | PTX | PTX-PEG | PTX-PEG-ALN |
|---|---|---|---|
| $T_{1/2}\alpha$ | 1.3 ± 0.3 | 7.5 ± 0.6 | 18.9 ± 0.8 |
| $T_{1/2}\beta$ | 15.1 ± 4.8 | 77.9 ± 4.0 | 85.5 ± 19.8 |
| $AUC^{0-\infty}$ (µL min/mL) | 31.2 ± 9.2 | 407.3 ± 70.7 | 948.4 ± 119.2 |
| Clearance (mL/min) | 7.4 ± 1.5 | 0.56 ± 0.08 | 0.24 ± 0.03 |
| Vd (mL) | 160.9 ± 2.1 | 63.4 ± 6.2 | 29.9 ± 5.5 |

As shown in Table 2, the elimination half-lives ($T_{1/2\beta}$) of PTX-PEG and PTX-PEG-ALN were 77.9 minutes and 85.5 minutes, respectively, which is a marked prolongation with respect to the 15.1 minutes of free PTX. Consequently, also the area under the curve (AUC) of PTX-PEG and PTX-PEG-ALN was increased resulting in 13-fold and 30-fold larger values than the AUC value of free PTX, respectively.

In Vivo Tumor Accumulation and Body Distribution:

Non-invasive fluorescence imaging technology was utilized to monitor the real-time distribution, and tumor accumulation of FITC-labeled PEG, PTX-PEG, PEG-ALN and PTX-PEG-ALN conjugates. Mice bearing MDA-MB-231-mCherry breast cancer tumors in the tibia were injected i.v. with FITC-labeled conjugates. Immediately following administration of the conjugates, mice became entirely fluorescent. A semi-quantitative time-dependent tumor/background contrast profile was derived from the average fluorescence intensities of equal areas within tumor and normal skin regions and is presented in FIG. 13A. As shown therein, the tested FITC-labeled conjugates accumulated gradually and preferentially at tumor sites. At 8 hours post injection, tumors and major organs were excised for ex vivo imaging to determine tissue distribution, as presented in FIG. 13B. As shown therein, for all of they tested conjugates, apart for tumors, uptake was predominant in kidney tissues due to renal excretion. Preferred accumulation in bones was observed in the PEG-ALN and PTX-PEG-ALN conjugates, indicating that ALN retained its binding capacity to bone mineral.

Anti-Tumor Efficacy and Toxicity on Syngeneic 4T1-mCherry Murine Mammary Adenocarcinoma in the Tibia:

The antitumor effect of PTX-PEG-ALN conjugate following intravenous injection was evaluated on syngeneic mCherry-labeled 4T1 murine mammary adenocarcinomas in the tibia. Mice were treated with MTD of PTX and equivalent concentrations of the conjugates. Tumor growth was monitored non-invasively using fluorescence imaging system (CRI™ Maestro).

As presented in FIGS. 15A-D, a significant tumor growth inhibition was recorded in mice treated with both PTX-PEG and PTX-PEG-ALN conjugates. On day 15, when mice were euthanized, PTX-PEG-ALN and PTX-PEG conjugates inhibited tumor growth by 48% and 37%, respectively, as compared with saline treated mice (see, FIG. 15A). Treatment with ALN was very toxic and caused severe body weight loss and mortality within 2 injections both in free ALN-treated mice and in mice treated with the combination of free ALN plus PTX (see, FIG. 15C). Therefore, in these groups, tumor progression could not be determined. In contrast to free ALN, mice treated with PEG-ALN conjugate did not lose weight. Further body weight loss was not recorded in any of the other treatment groups (see, FIG. 15C).

Figure 15A:
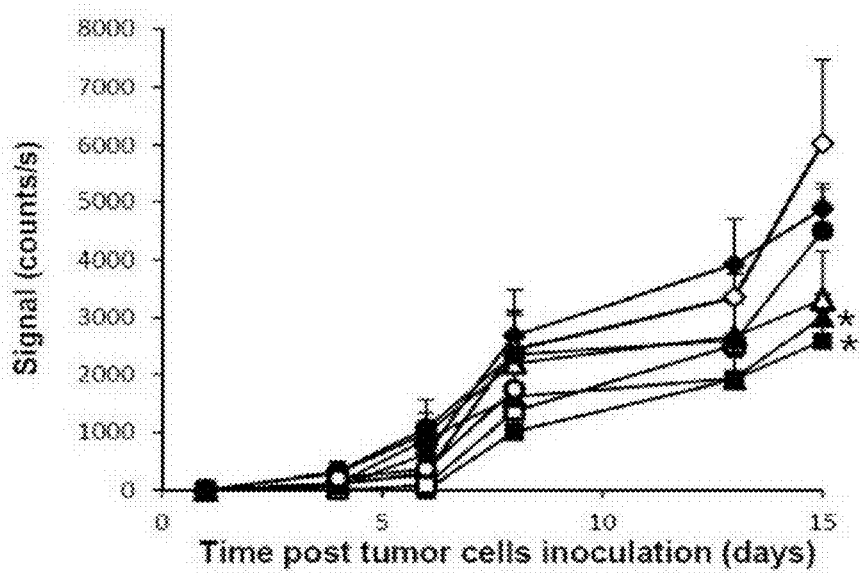
Figure 15B:
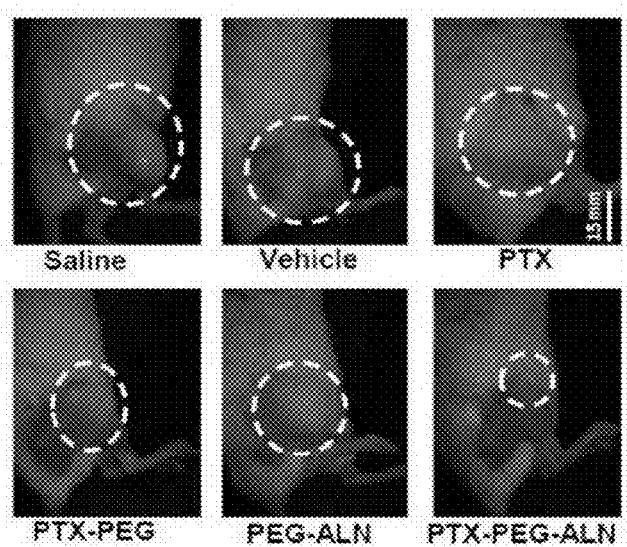
Figure 15C:
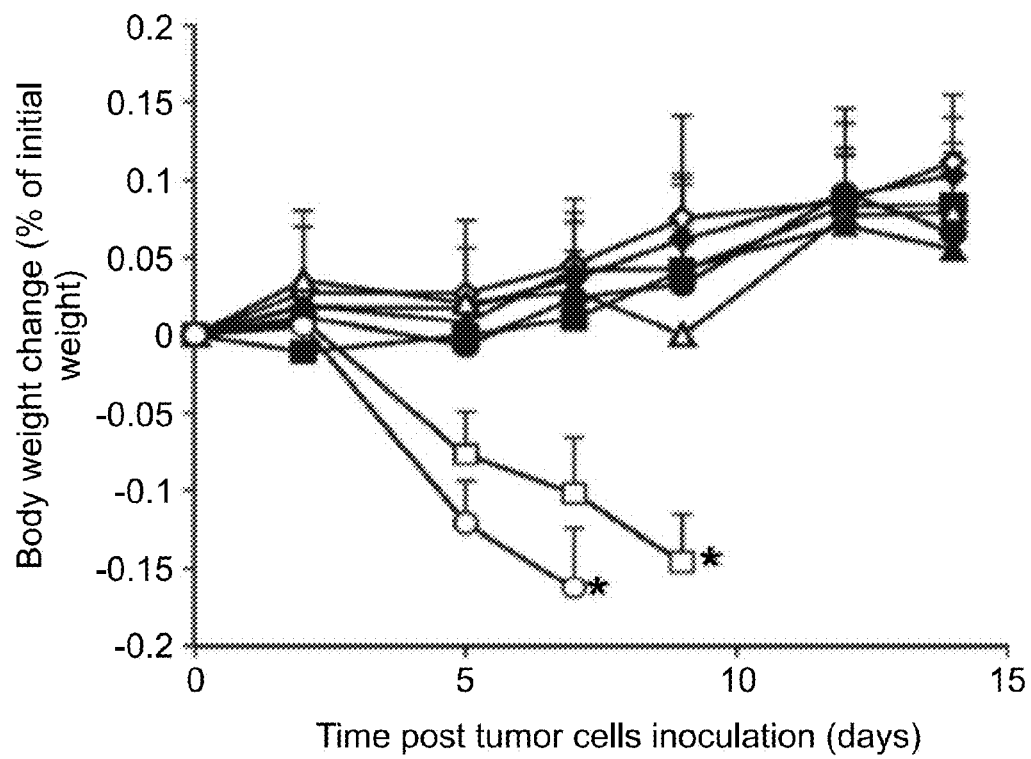
Figure 15D:
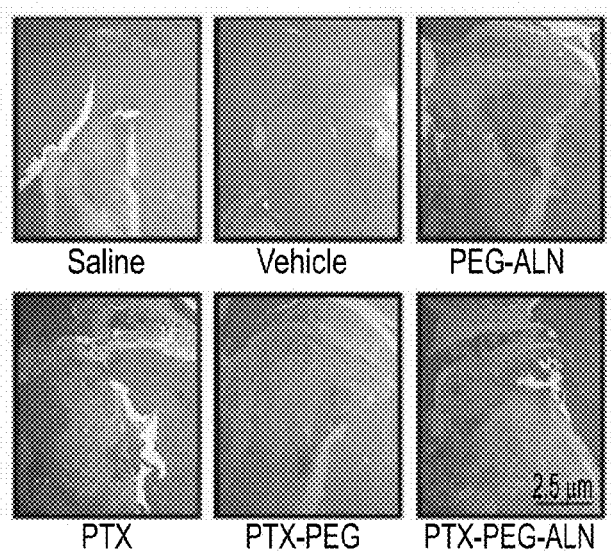

Representative histology sections of H & E staining through the tibia demonstrated that most of the PEG conjugates treated-mice had intact cortical and trabecular bone (FIG. 15D). However, in the control groups and in mice treated with PTX, tumor filled the bone marrow space and destroyed both trabecular and cortical bone. Increased percent necrosis was observed in control groups of mice due to the larger size of tumors incorporating a necrotic hypoxic core, as compared with smaller tumors and decreased percent necrosis observed in all treated groups of mice.

As shown in FIG. 16A, WBC counts in mice treated with the tested conjugates or with PTX-vehicle were all at the normal range and similar to those of control mice injected with saline. Only in mice treated with free PTX, a significant decrease in the WBC counts was recorded. Due to the severe toxicity effect of free ALN and the combination of free ALN and PTX, that caused mortality prior to day 11, no data concerning the WBC counts could be obtained from these mice groups.

Immunohistochemical analysis of paraffin-embedded sections of CD34 staining is presented in FIG. 16B and show a significant reduction, of about 50%, in micro-vessel density (MVD) in mice treated with PTX, PTX-PEG, and PTX-PEG-ALN there was PTX-PEG-ALN conjugate, as compared to the saline-treated control group.

Following the in vitro results demonstrating the anti-angiogenic activity of the conjugates described herein, the effect of various treatments on CEC and CEP populations in blood circulation in mice bearing the 4T1-mCherry adenocarcinomas in the tibia was tested.

Viable CEP have been shown to correlate with angiogenesis. A substantial increase in the number of viable CEP was observed in peripheral blood of mice 24 hours after they were treated with paclitaxel chemotherapy. Such cells were found in large numbers in treated tumor sites, and thus may account for the induction in angiogenesis and tumor re-growth following therapy. In addition, apoptotic CEC are likely to represent an indirect marker of vessel damage and/or turnover and remodeling.

Using multi-parametric flow cytometry, both apoptotic CEC and viable CEP populations were analyzed, and the obtained data is presented in FIGS. 17A and 17B. As shown in FIG. 17A, in all treatments there was no difference in apoptotic CEC counts in the blood. However, in mice treated with PTX-PEG-ALN conjugate there was a significant increase in the apoptotic CEC counts in the blood. As shown in FIG. 17B, an increase in viable CEP following PTX therapy, as opposed to PTX-PEG-ALN or PTX-PEG therapy was observed. These results provide further support for the anti-angiogenic activity exhibited by the PTX-PEG-ALN conjuagues as described herein.

Anti-Tumor Efficacy and Toxicity on a Xenograft Model of MDA-MB-231-mCherry Mammary Adenocarcinoma in the Tibia:

The antitumor effect of exemplary conjugates as described herein, following intravenous injection was also evaluated on a xenograft mouse model of mCherry-labeled MDA-MB-231 mammary adenocarcinomas in the tibia. The results are presented in FIGS. 18A-D and show that mice treated with the PTX-PEG-ALN conjugate exhibited superior antitumor efficacy, 50% inhibition in tumor growth, as compared to saline control mice (see, FIG. 18A).

As shown in FIG. 18B, the PTX-PEG-ALN conjugate did not induce body weight loss. However, combination of MTD (minimal therapeutic dose) of free PTX and ALN was very toxic and induced mortality within one treatment. Treatment with half dose of the combination of free PTX and ALN was also very toxic and caused severe body weight loss that almost reached 20% decrease, but was recovered after treatment withdrawal (FIG. 18B).

Figure 18C:
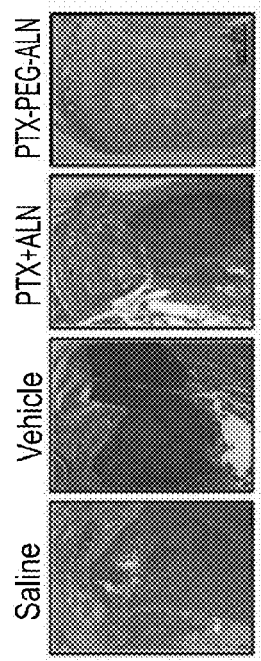

As shown in FIG. 18C, representative H&E staining of paraffin-embedded sections of MDA-MB-231-mCherry tumors in the tibia demonstrated similarly to the H&E from mCherry-4T1 tumors that in control mice, tumor filled the bone marrow, destroyed bone, and penetrated into soft tissues and the proximal joint. In contrast, mice treated with PTX-PEG-ALN conjugate had intact cortical and trabecular bone. In control mice, the tumor diffusely invaded bone marrow with destruction of bone trabeculae. When treated with the herein disclosed conjugate, the bones looked normal with slight irregularity of the trabecular outlines.

As shown in FIG. 18D, an overall increased percent necrosis due to larger size of tumors with hypoxic core was observed in control groups of mice, as compared with smaller tumors and decreased overall percent necrosis observed in mice treated with PTX-PEG-ALN conjugate. On the contrary, a significant necrotic core in the ossea medulla was observed only in mice treated with the conjugate, whereas in control mice tumor within the ossea medulla was viable with no necrosis observed.

WBC counts of mice treated with the conjugate or combination of the free drugs were comparable to control mice treated with saline or PTX-vehicle (see, FIG. 19A).

As shown in FIG. 19B, immunohistochemical analysis of paraffin-embedded sections of CD34 staining revealed that in mice treated with the combination of free PTX plus ALN, and the PTX-PEG-ALN conjugate, there was a significant reduction in the micro-vessel density (MVD) of about 73% and 54% in PTX-PEG-ALN conjugate and the combination of free PTX plus ALN, respectively.

FIGS. 20A and 20B present the effect of the various treatments on the blood levels of CEC and CEP in this mice model. It is shown therein that, as opposed to the 4T1, in MDA-MB-231 mouse model, there was a substantial increase in apoptotic CEC only in the PTX-vehicle-treated group, when compared to the other groups (see, FIG. 20A). In addition, similar to 4T1 tumor model, in MDA-MB-231 tumors, a decrease in viable CEP following therapy with the PTX-PEG-ALN conjugate, as opposed to the other treatments, was observed, suggesting that the conjugate possesses anti-angiogenic effect (see, FIG. 20B).

In summary, the data obtained in the in vivo studies conducted show that an exemplary conjugate according to some embodiments of the present invention, the PTX-PEG-ALN conjugate as described herein, showed substantial antitumor effects in both murine syngeneic and human xenograft mouse models. The superiority of the conjugate is evident in its safety compared to the free drugs. In both mouse models treatment with the combination of free PTX plus ALN caused mortality within the first injection. Even treatment with free PTX plus ALN at half-dose was very toxic and caused a reduction of 20% in body weight, whereas treatment with the PTX-PEG-ALN conjugate did not. Also, in contrast to free ALN, mice treated with PEG-ALN conjugate did not lose weight, suggesting that the conjugation with PEG increased the safety of ALN without hindering its bone-targeting affinity. Without being bound by any particular theory, it is assumed that while free ALN diffuses through the blood vessels and affects normal healthy tissues besides the bones, and causes toxicity, the conjugate is targeted only to the bones.

WBC levels in mice treated with the exemplary PTX-PEG-ALN conjugate were comparable to those in control mice, whereas mice treated with free PTX, displayed a significant decrease in WBC levels. These results indicate that the conjugation of PTX with PEG and ALN decreases the toxic effect of PTX on the bone marrow.

H&E staining for both 4T1-mCherry and mCherry-MDA-MB-231 models showed intact bone in mice treated with the exemplary PTX-PEG-ALN conjugate. However, in control mice, bones were destroyed, and tumor penetrated into the proximal soft tissues and the proximal joint. Although overall percent necrosis was increased in control treated mice, as compared to mice treated with the exemplary PTX-PEG-ALN conjugate, a specific larger necrotic area was observed in the ossea medulla of conjugate-treated mice. These findings suggest that the exemplary PTX-PEG-ALN conjugate, as designed, is targeted into bone, and is active in the bones. H&E staining of PEG-ALN-treated mice showed more preserved bones, as compared with saline-treated control mice.

Immunohistochemical CD34 staining carried out on 4T1 and MDA-MB-231 tumor sections showed that PTX-PEG-ALN conjugate is directed against tumor endothelial cells and inhibits angiogenesis, suggesting that the antitumor effect caused by the conjugates as described herein is mediated by impairing the blood supply to the tumor. These data is in corroboration with the in vitro anti-angiogenic activity presented by exemplary conjugates and the in vivo evaluation of the angiogenic cellular markers, apoptotic CEC, and viable CEP.

Overall, these studies demonstrate the superior efficacy and reduced toxicity exhibited by the conjugates as described herein, particularly as compared to free PTX.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:
1. A conjugate having the structure:
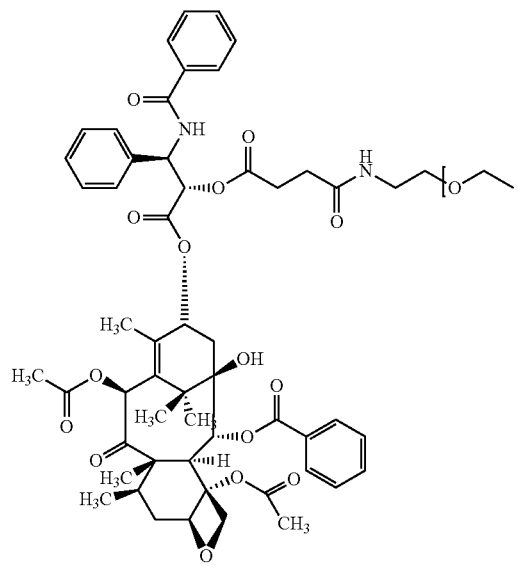
-continued
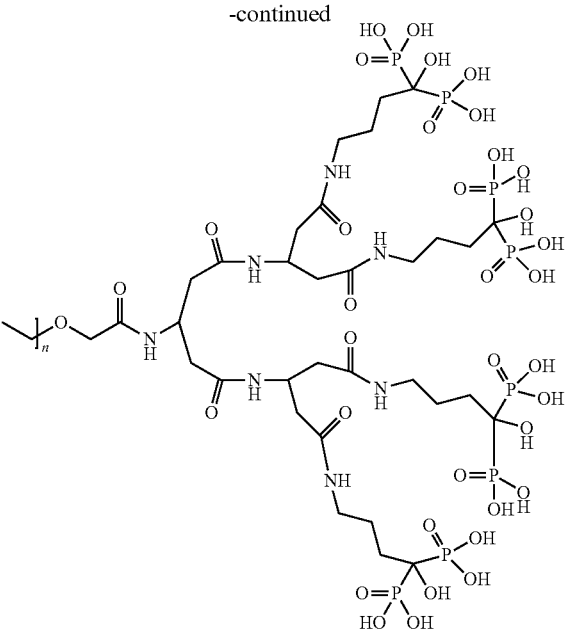
wherein n is an integer that ranges from 10 to 1000.
2. A conjugate having the structure:
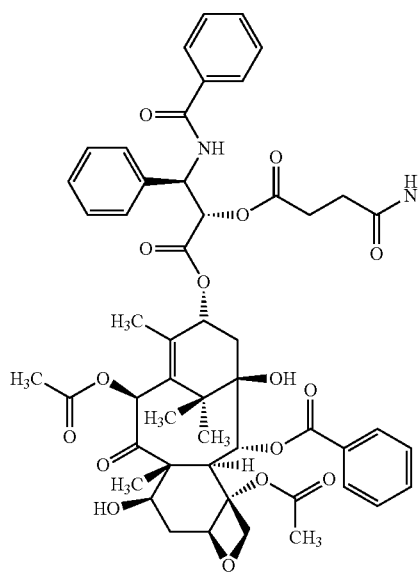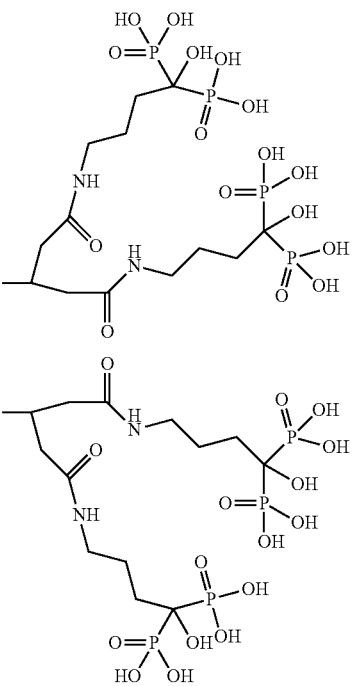

wherein n is an integer that ranges from 10 to 1000, wherein X is a lysine residue coupled to a labeling agent.

3. A pharmaceutical composition comprising, as an active ingredient, the conjugate of claim 1 and a pharmaceutically acceptable carrier.

4. The pharmaceutical composition of claim 3, being packaged in a packaging material and identified in print, in or on said packaging material, for use in the treatment of a bone related disease or disorder.

5. A pharmaceutical composition comprising, as an active ingredient, the conjugate of claim 2 and a pharmaceutically acceptable carrier.

6. A method of treating a bone related disease or disorder in a subject in need thereof, the method comprising administering to the subject a therapeutically effective amount of the conjugate of claim 1.

7. A method of monitoring a bone related disease or disorder in a subject, the method comprising:
- administering to the subject the conjugate of claim 2; and
- employing an imaging technique for monitoring a distribution of the conjugate within the body or a portion thereof.

8. The pharmaceutical composition of claim 5, being packaged in a packaging material and identified in print, in or on said packaging material, for use in monitoring a bone related disease or disorder.

* * * * *